United States Patent
Fleetham et al.

(10) Patent No.: US 11,889,708 B2
(45) Date of Patent: Jan. 30, 2024

(54) ORGANIC ELECTROLUMINESCENT MATERIALS AND DEVICES

(71) Applicant: Universal Display Corporation, Ewing, NJ (US)

(72) Inventors: Tyler Fleetham, Newtown, PA (US); Nicholas J. Thompson, New Hope, PA (US); Peter Wolohan, Princeton Junction, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 193 days.

(21) Appl. No.: 17/086,989

(22) Filed: Nov. 2, 2020

(65) Prior Publication Data
US 2021/0151692 A1    May 20, 2021

Related U.S. Application Data

(63) Continuation-in-part of application No. 16/683,507, filed on Nov. 14, 2019.

(51) Int. Cl.
*H10K 85/60* (2023.01)
*C09K 11/02* (2006.01)
*C07D 209/86* (2006.01)
*H10K 50/11* (2023.01)
*H10K 101/10* (2023.01)

(52) U.S. Cl.
CPC ....... *H10K 85/6572* (2023.02); *C07D 209/86* (2013.01); *C09K 11/025* (2013.01); *H10K 50/11* (2023.02); *H10K 2101/10* (2023.02)

(58) Field of Classification Search
CPC ............ H01L 51/0072; H01L 51/0067; H01L 51/5012; H01L 51/5016; H01L 2251/5384; C07D 403/14; C07D 487/04; C09K 11/02; C09K 11/06; C09K 2211/1007; C09K 2211/1018; C09K 2211/1029; C09K 2211/1044; C09K 2211/185
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |

(Continued)

FOREIGN PATENT DOCUMENTS

| | | |
|---|---|---|
| CN | 108285452 | 7/2018 |
| EP | 0650955 | 5/1995 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Shane Fang
(74) *Attorney, Agent, or Firm* — DUANE MORRIS LLP

(57) ABSTRACT

Provided are ortho-substituted biphenyl compounds with one or more bicarbazole linkages. Also provided are formulations comprising these ortho-substituted biphenyl compounds. Further provided are OLEDs and related consumer products that utilize these ortho-substituted biphenyl compounds.

18 Claims, 2 Drawing Sheets

(56) References Cited

U.S. PATENT DOCUMENTS

| | | |
|---|---|---|
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 10,263,196 B2 | 4/2019 | Danz et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0127823 A1 | 6/2005 | Iwakuma |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2017/0069853 A1* | 3/2017 | Kim ................. H01L 51/0071 |
| 2018/0334462 A1 | 11/2018 | Dyatkin |
| 2019/0341557 A1 | 11/2019 | Lin |
| 2021/0066613 A1 | 3/2021 | Cheng |

FOREIGN PATENT DOCUMENTS

| | | |
|---|---|---|
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 4552382 | 9/2010 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

(56) References Cited

OTHER PUBLICATIONS

Hamada, Yuji et al., "High Luminance in Organic Electroluminescent Devices with Bis(10-hydroxybenzo[h]quinolinato) beryllium as an Emitter, " Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based On Silole Derivatives And Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes Of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

CROSS-REFERENCE TO RELATED APPLICATIONS

This application is a continuation-in-part of U.S. patent application Ser. No. 16/683,507, filed Nov. 14, 2019, and also claims priority under 35 U.S.C. § 119(e) to U.S. Provisional Application No. 63/017,220, filed on Apr. 29, 2020, the entire contents of which are incorporated herein by reference.

FIELD

The present disclosure generally relates to organometallic compounds and formulations and their various uses including as hosts or emitters in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

Provided are ortho-substituted biphenyl compounds with one or more bicarbazole linkages. The ortho-substituted biphenyls provide a twisted molecular geometry which can increase the triplet energy of the molecule and the bicarbazole moiety provides a good charge transport moiety. These compounds can be used as hosts in phosphorescent devices to enable higher efficiency and longer lifetimes compared to related compounds without twisted geometries or the bicarbazole linkages.

In one aspect, the present disclosure provides a compound comprising a structure of Formula I

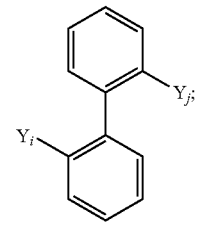

wherein:

$Y_i$ is

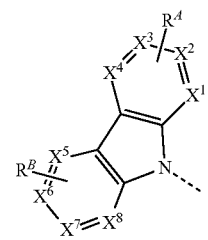

and $Y_j$ is

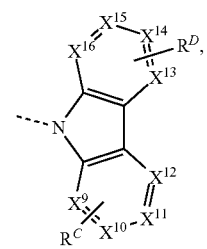

$R^A$, $R^B$, $R^C$, and $R^D$ each independently represents zero, mono, di-substitution or the maximum allowable number of substitutions;

each $R^A$, $R^B$, $R^C$, and $R^D$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

at least one of $R^A$, $R^B$, $R^C$, and $R^D$ comprises a carbazole moiety;

$X^1$-$X^{16}$ is independently C or N; and any two substituents can be joined or fused together to form a ring.

In another aspect, the present disclosure provides a formulation of the compound of the present disclosure.

In yet another aspect, the present disclosure provides an OLED having an organic layer comprising the compound of the present disclosure.

In yet another aspect, the present disclosure provides a consumer product comprising an OLED with an organic layer comprising a compound comprising a structure of Formula I as described herein.

DETAILED DESCRIPTION

A. Terminology

Figure 1:
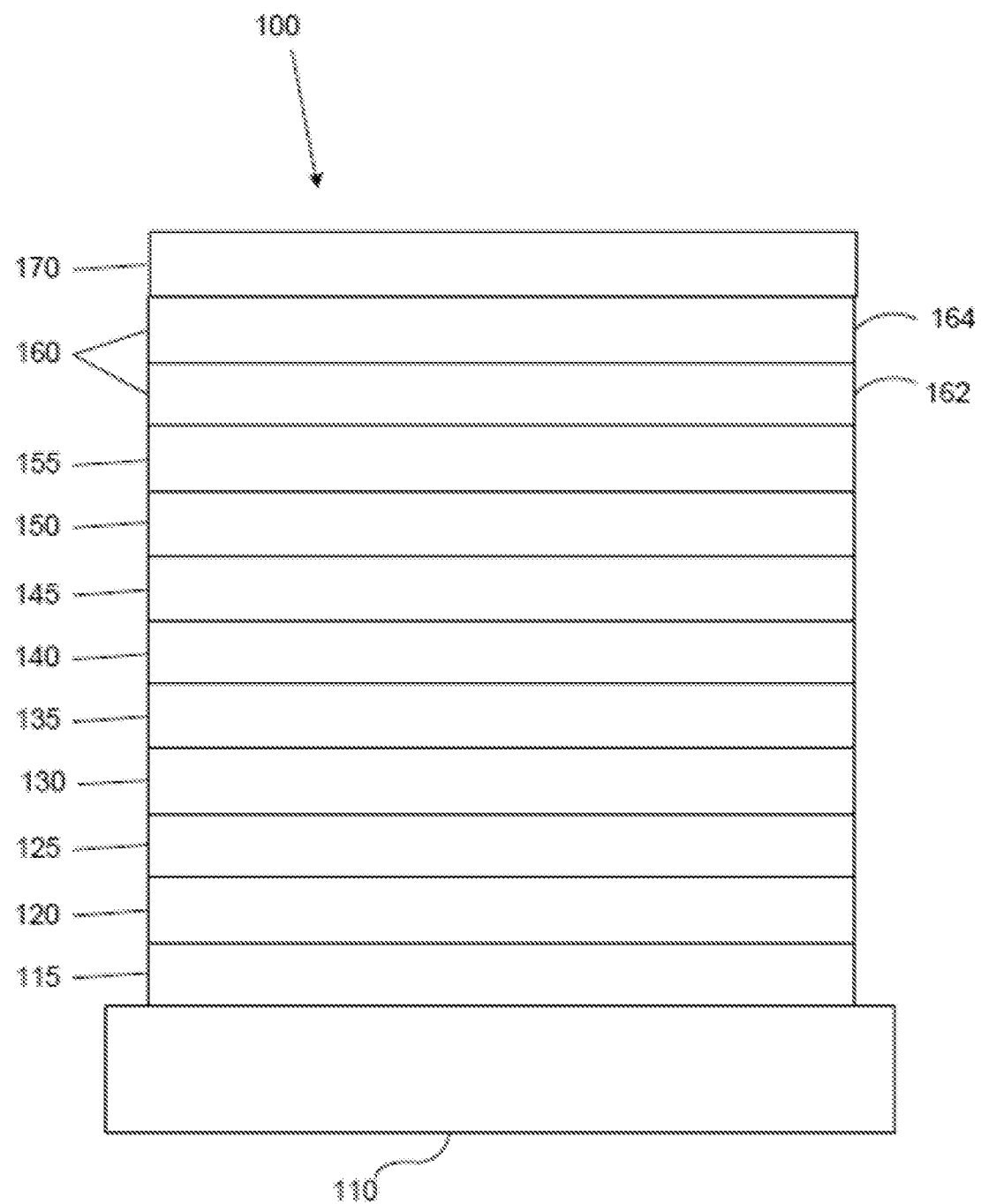
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —$OR_s$ radical.

The terms "sulfanyl" or "thio-ether" are used interchangeably and refer to a —$SR_s$ radical.

The term "sulfinyl" refers to a —S(O)—$R_s$ radical.

The term "sulfonyl" refers to a —$SO_2$—$R_s$ radical.

The term "phosphino" refers to a —$P(R_s)_3$ radical, wherein each $R_s$ can be same or different.

The term "silyl" refers to a —$Si(R_s)_3$ radical, wherein each $R_s$ can be same or different.

The term "boryl" refers to a —$B(R_s)_2$ radical or its Lewis adduct —$B(R_s)_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom.

Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, boryl, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, boryl, and combinations thereof.

In some instances, the more preferred general substituents are selected from the group consisting of deuterium, fluorine, alkyl, cycloalkyl, alkoxy, aryloxy, amino, silyl, boryl, aryl, heteroaryl, sulfanyl, and combinations thereof.

In yet other instances, the most preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed. (Reviews)* 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The Compounds of the Present Disclosure

In one aspect, the present disclosure provides a compound comprising a structure of Formula I

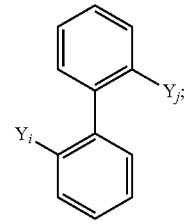

wherein: $Y_i$ is

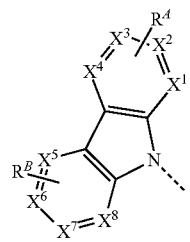

and $Y_j$ is

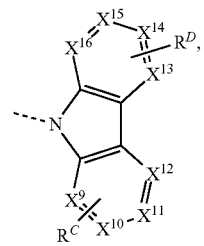

wherein:
$R^A$, $R^B$, $R^C$, and $R^D$ each independently represents zero, mono, di-substitution or the maximum allowable substitution;
each $R^A$, $R^B$, $R^c$, and $R^D$ is independently a hydrogen or a substituent selected from the group consisting of the general substituents defined herein;
at least one of $R^A$, $R^B$, $R^C$, and $R^D$ comprises a carbazole moiety;
each of $X^1$-$X^{16}$ is independently C or N; and
any two substituents can be joined or fused together to form a ring.

In one aspect, each $R^A$, $R^B$, $R^C$, and $R^D$ is independently a hydrogen or a substituent selected from the group consisting of the preferred general substituents defined above.

In one aspect, each $R^A$, $R^B$, $R^C$, and $R^D$ is independently a hydrogen or deuterium.

In one aspect, at least one of $R^A$, $R^B$, $R^C$, and $R^D$ comprises a carbazole group.

In one aspect, two of $R^A$, $R^B$, $R^c$, and $R^D$ are joined together to form a fused 5-membered or 6-membered carbocyclic or heterocyclic ring.

In one aspect, at least one of $X^1$-$X^{16}$ is N.

In one aspect, $X^1$-$X^{16}$ are C.

In one aspect, $Y_i$ is selected from the group consisting of:

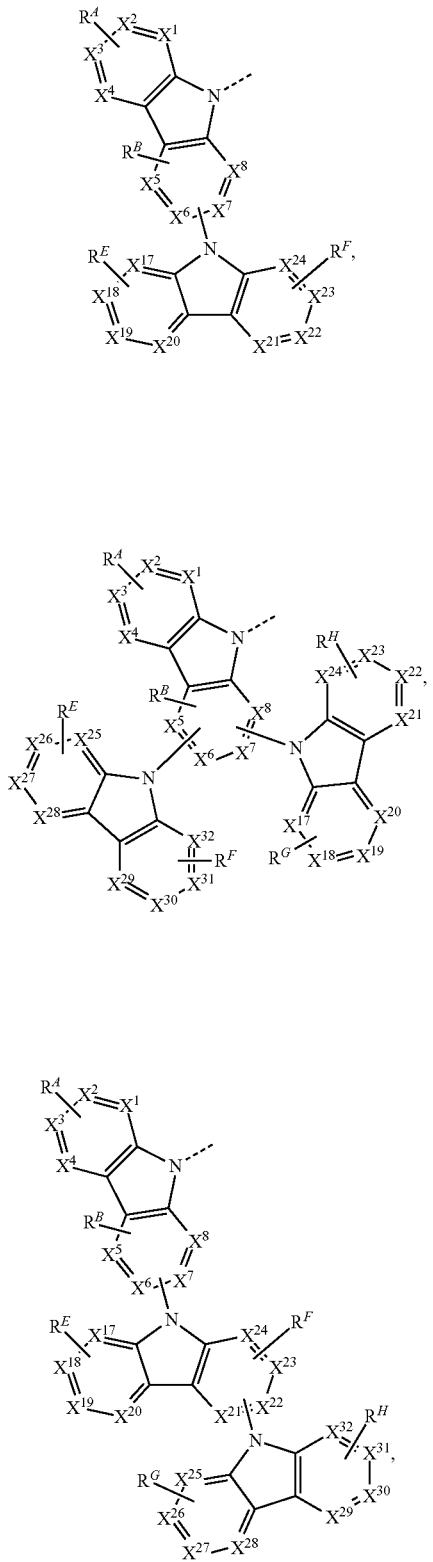

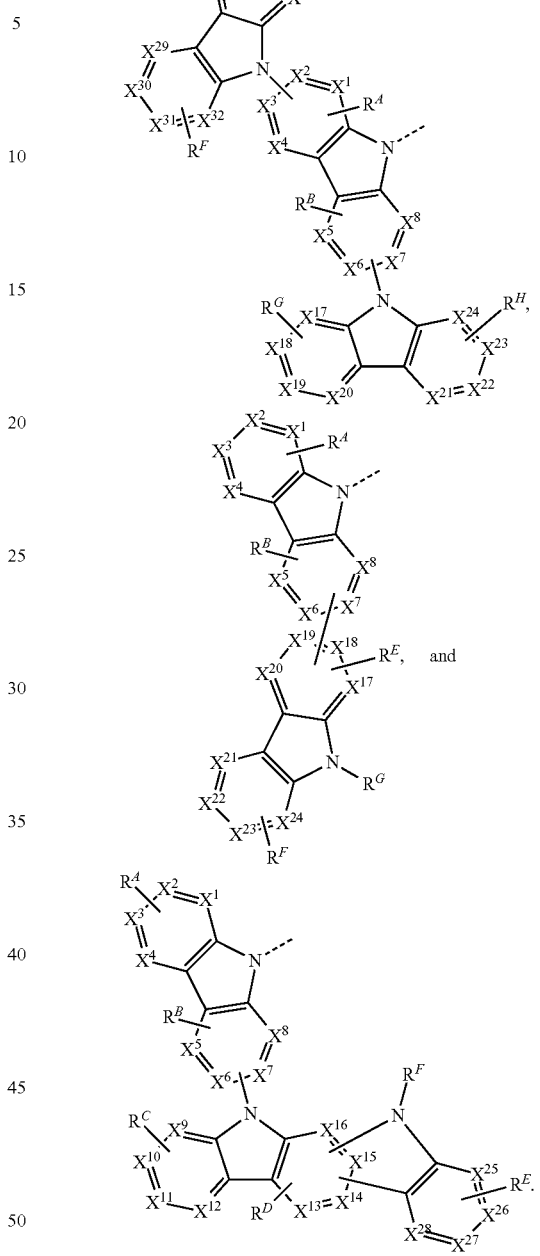

wherein $X^{17}$-$X^{32}$ are each independently C or N;

$R^E$, $R^F$, $R^G$, and $R^H$ each independently represents zero, mono, di-substitution or the maximum allowable substitution;

each $R^E$, $R^F$, $R^G$, and $R^H$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and any two $R^E$, $R^F$, $R^G$, and $R^H$ can be joined or fused together to form a ring.

In one aspect, $Y_i$ is selected from the group consisting of $Y_1$-$Y_{36}$, and $Y_j$ is selected from the group consisting of $Y_1$-$Y_{43}$, wherein $Y_1$-$Y_{43}$ have the following structures:
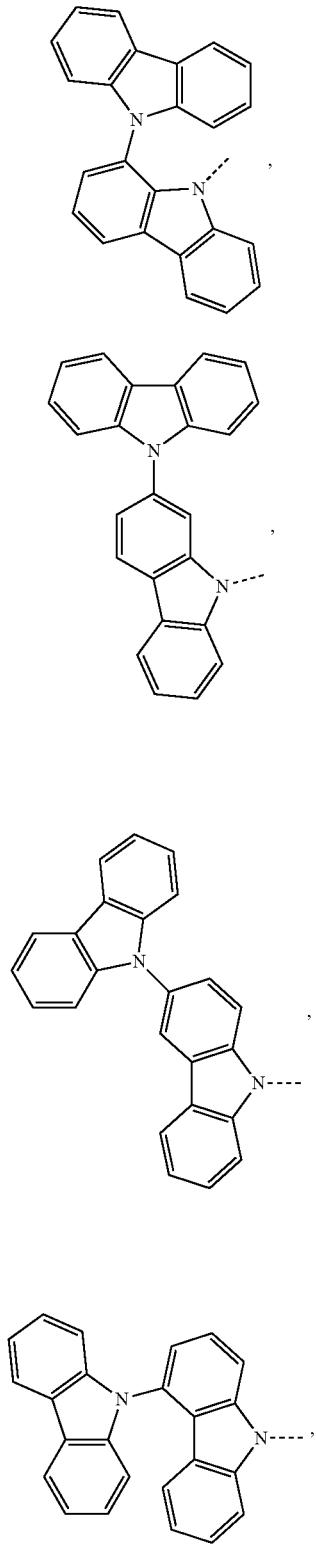
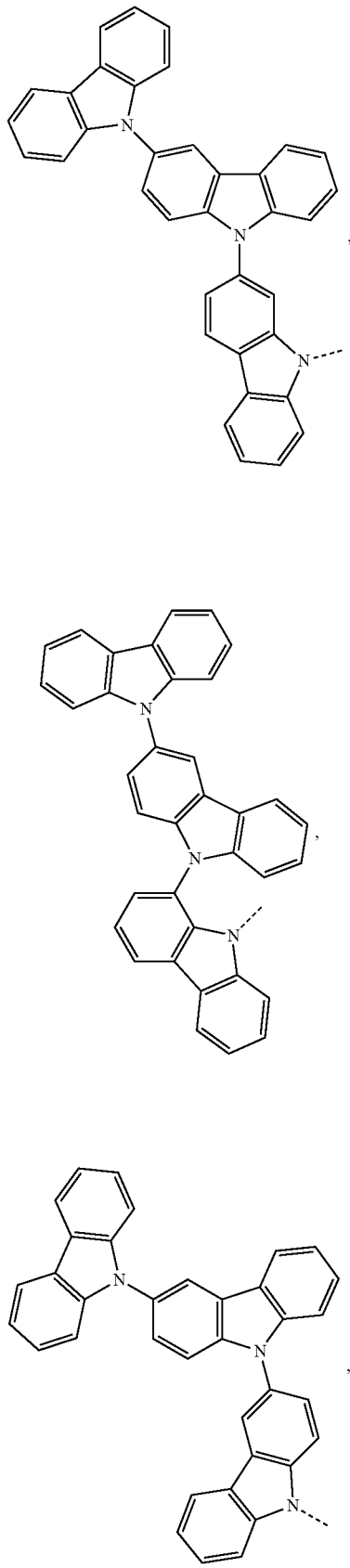

-continued
Y8
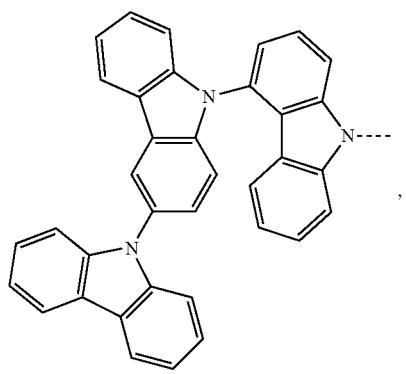
Y9
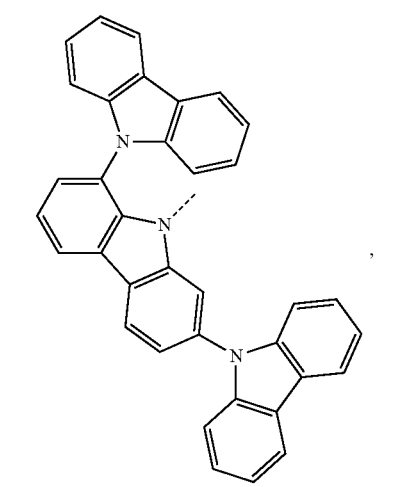
Y10
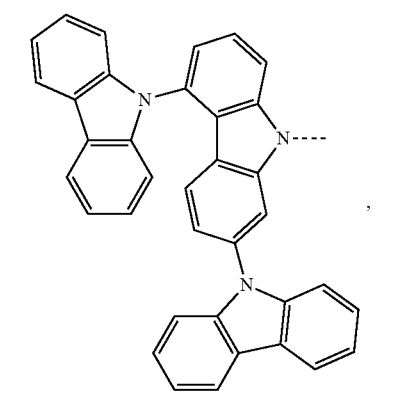
Y11
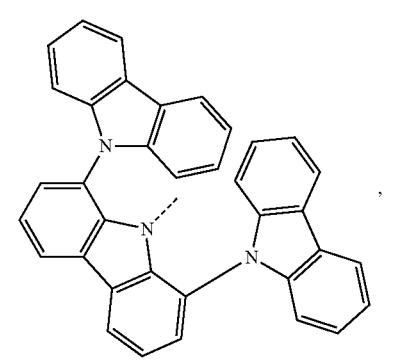
Y12
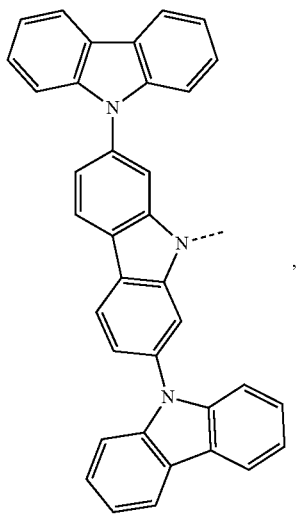
Y13
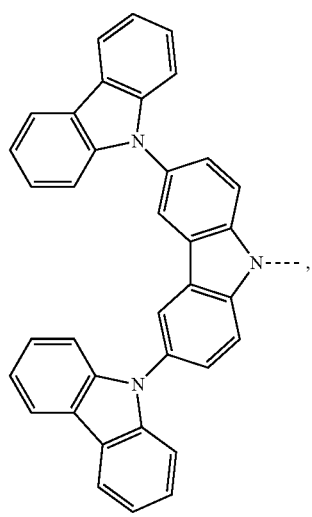
Y14
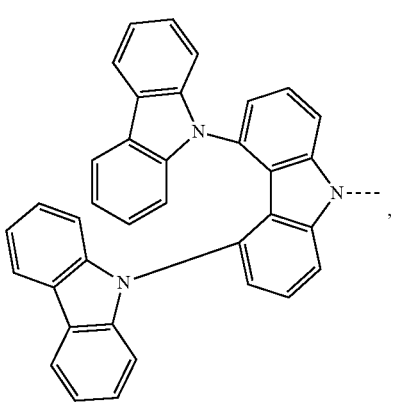

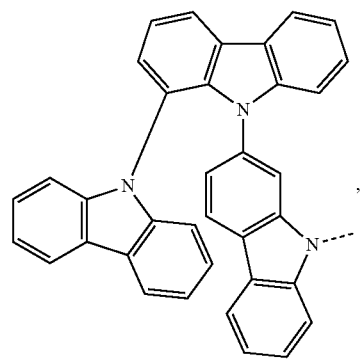 Y15
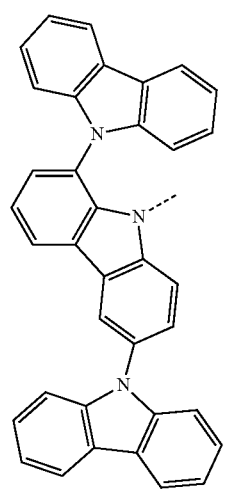 Y16
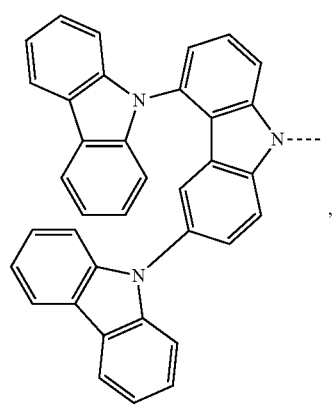 Y17
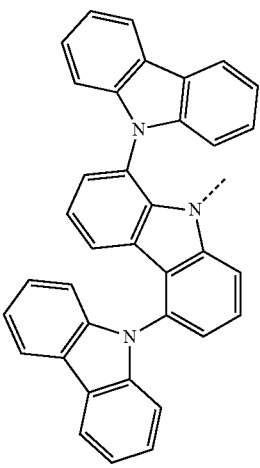 Y18
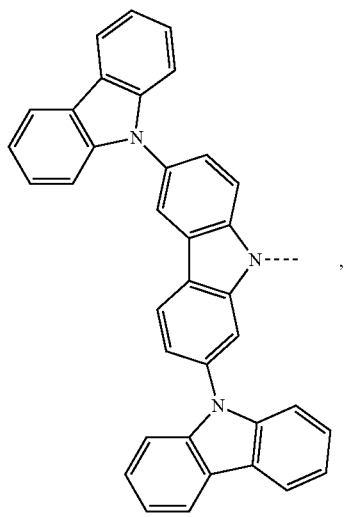 Y19
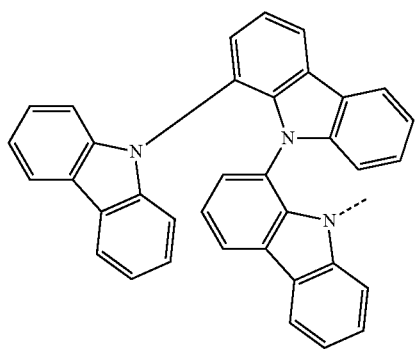 Y20

Y21
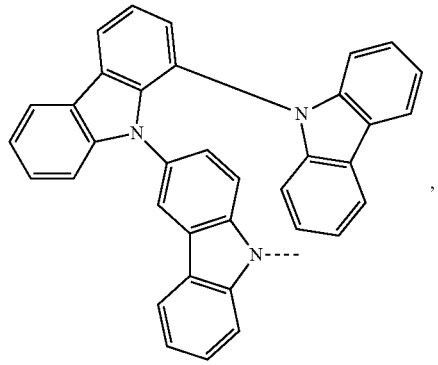
Y22
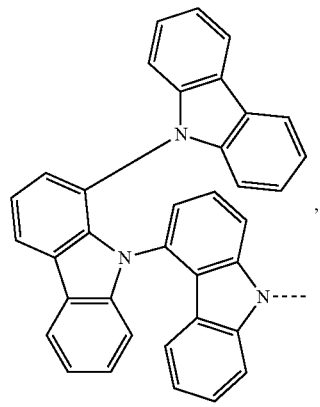
Y23
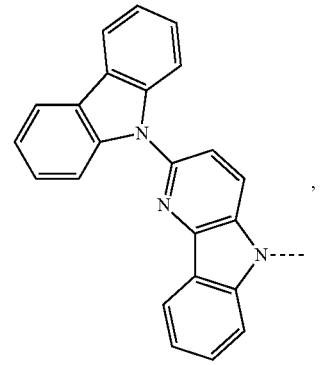
Y24
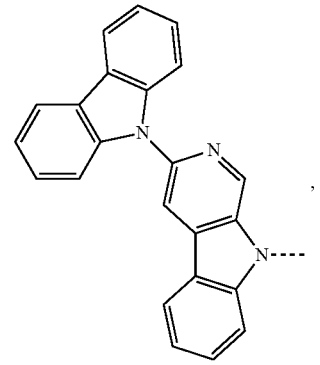
Y25
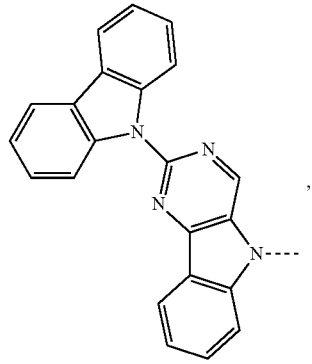
Y26
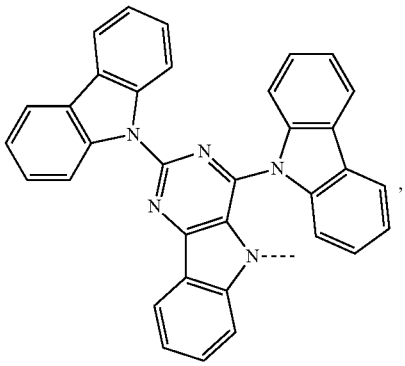
Y27
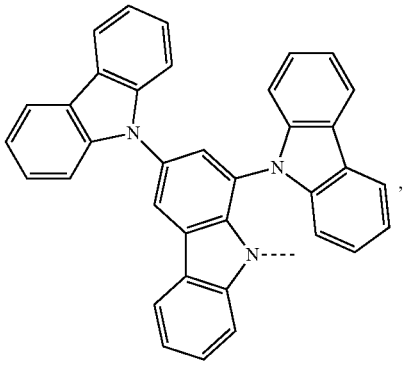
Y28
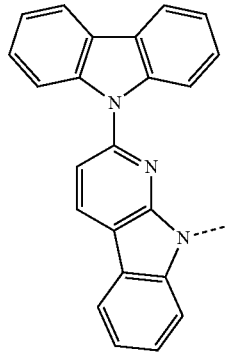

Y29
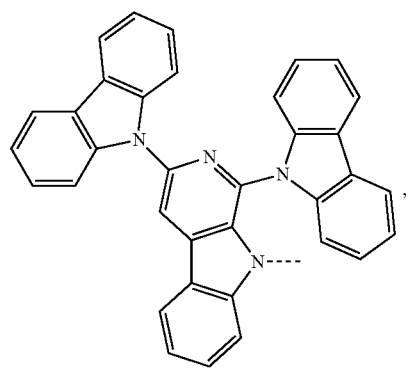
Y30
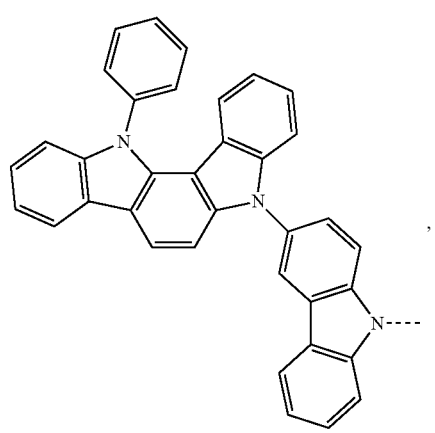
Y31
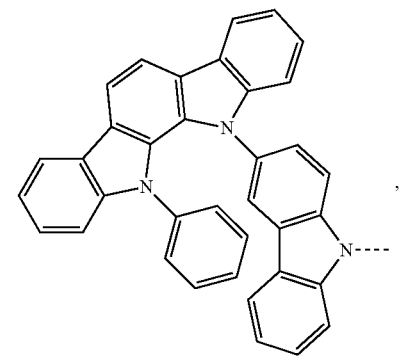
Y32
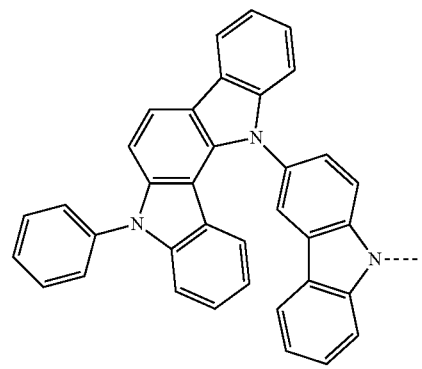
Y33
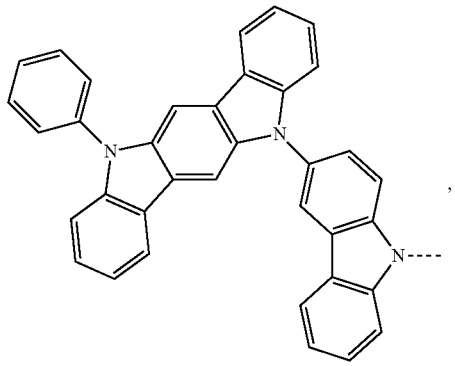
Y34
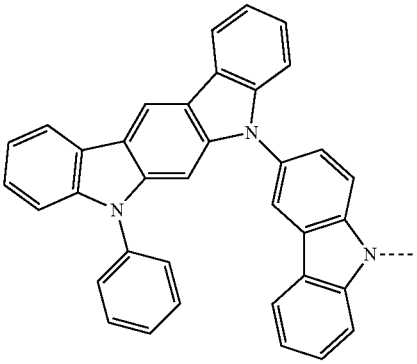
Y35
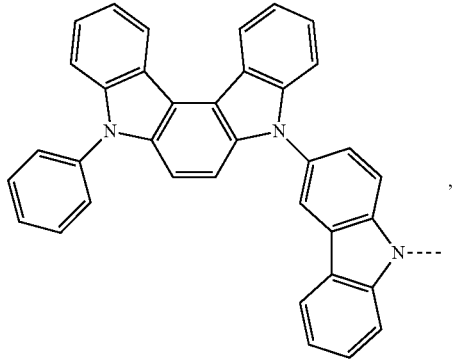
Y36
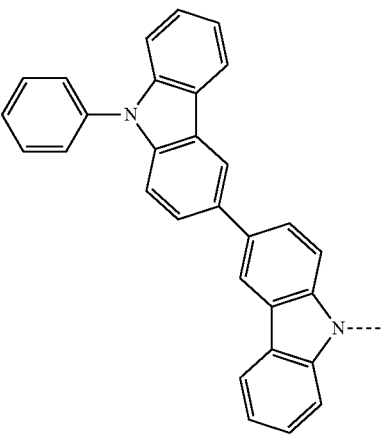

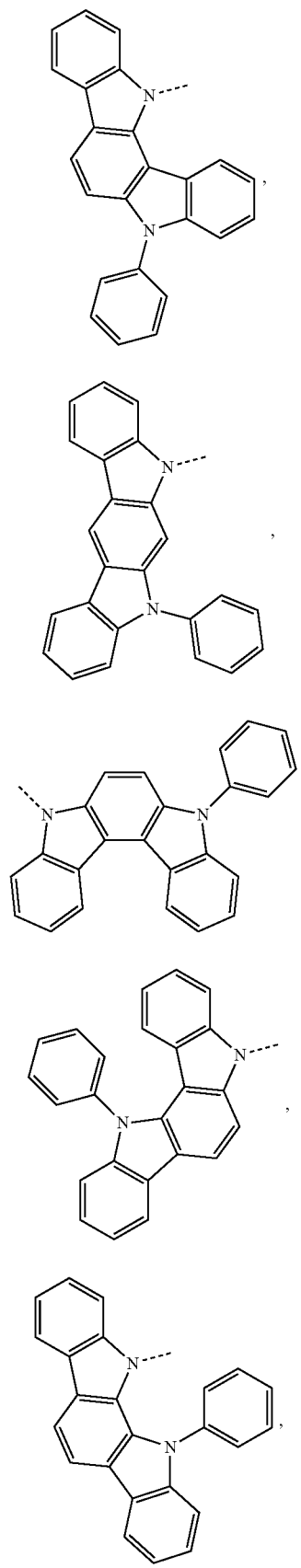
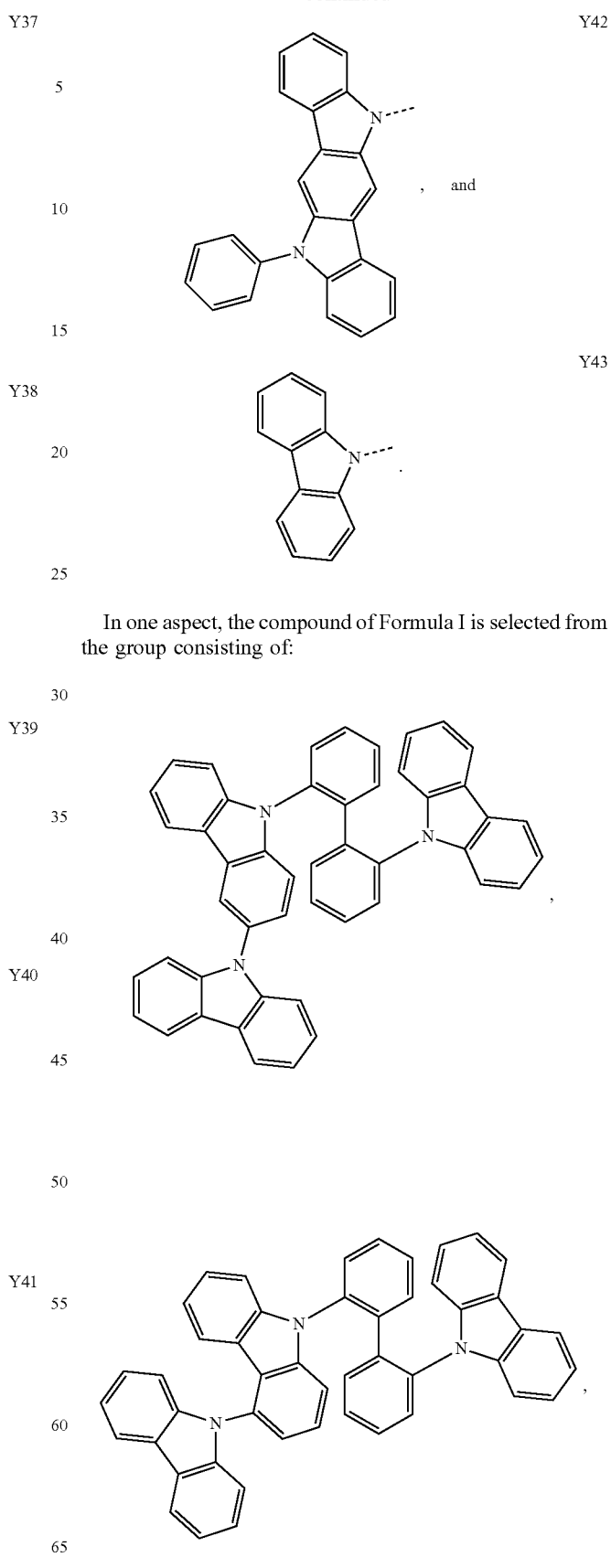
In one aspect, the compound of Formula I is selected from the group consisting of:

-continued
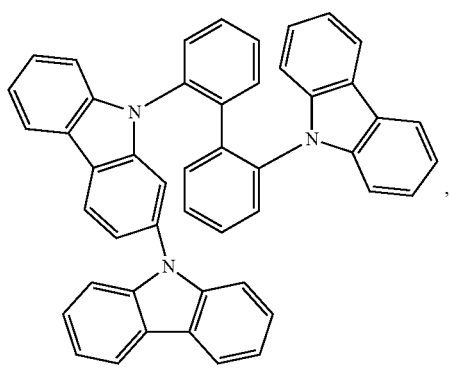,
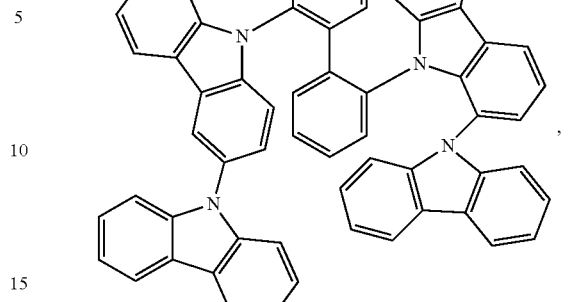,
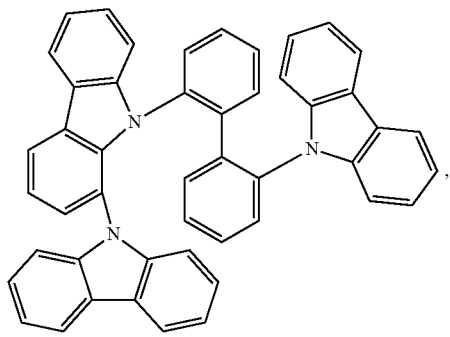,
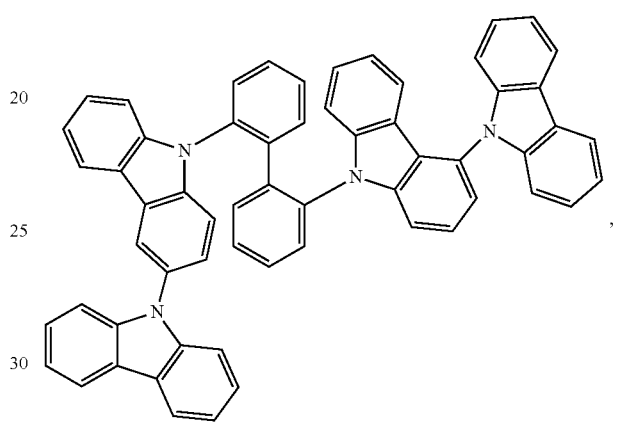,
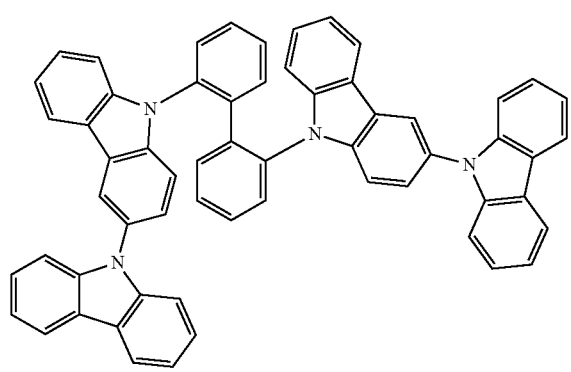,
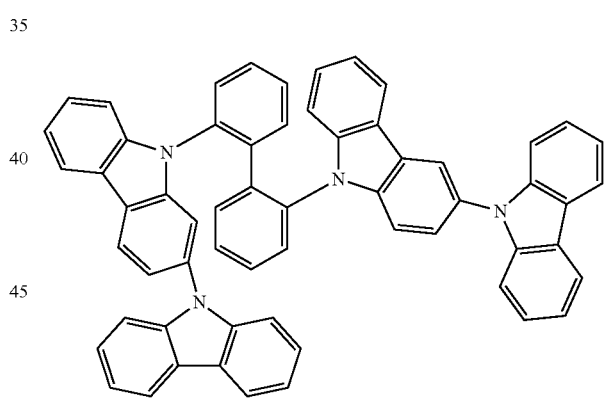,
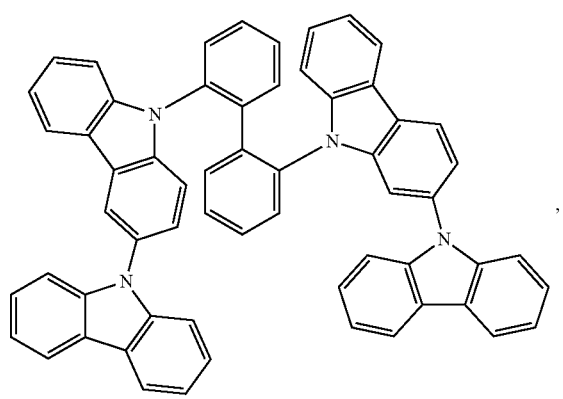,
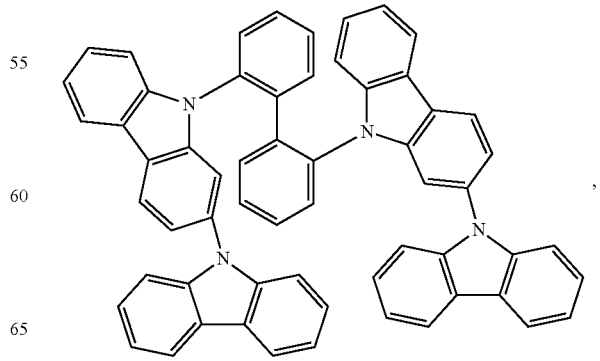,

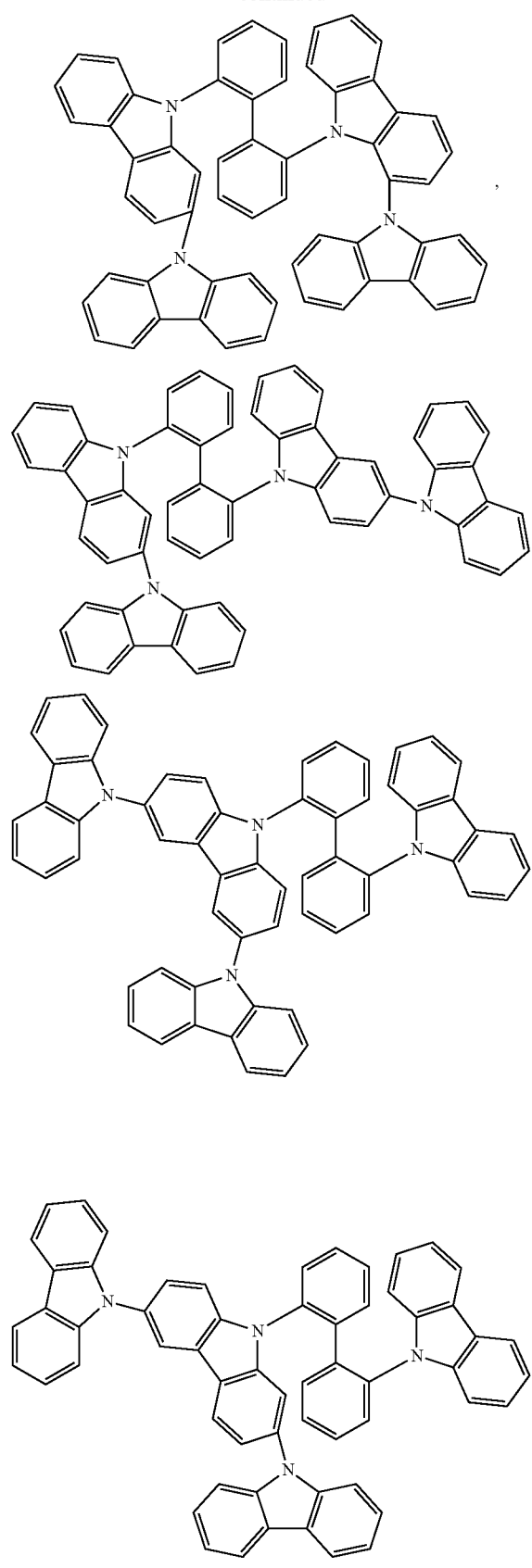
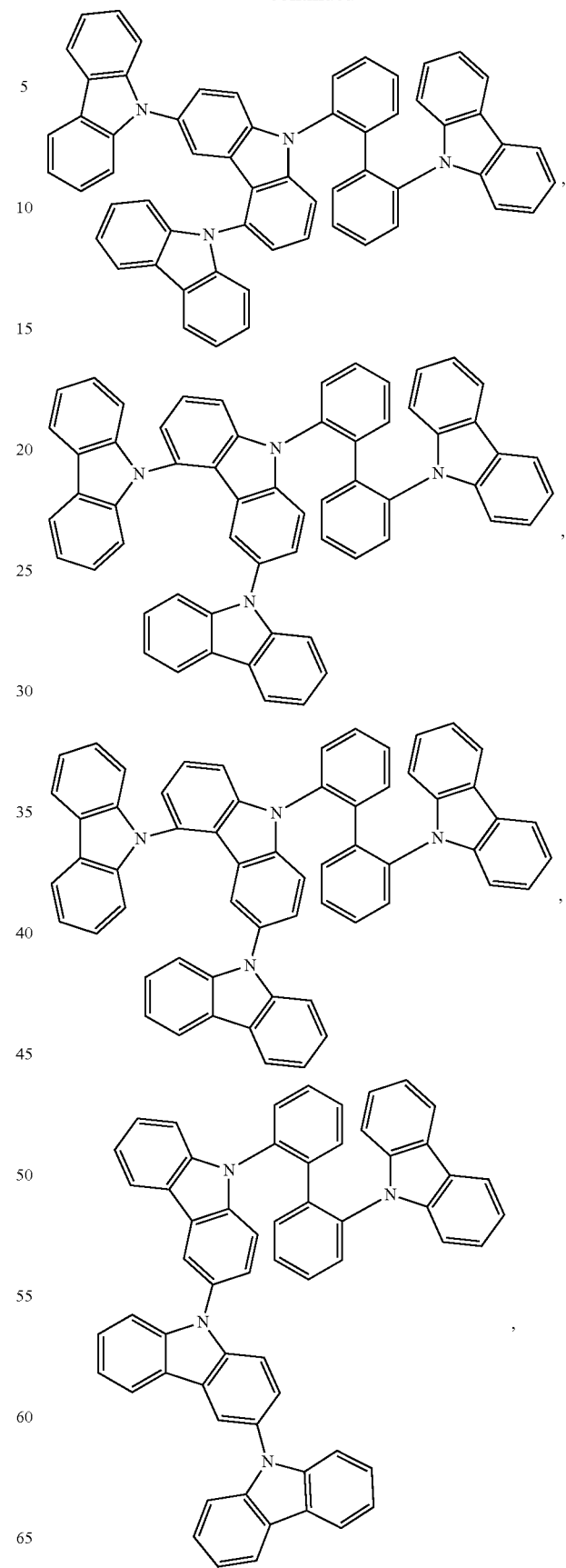

27
-continued
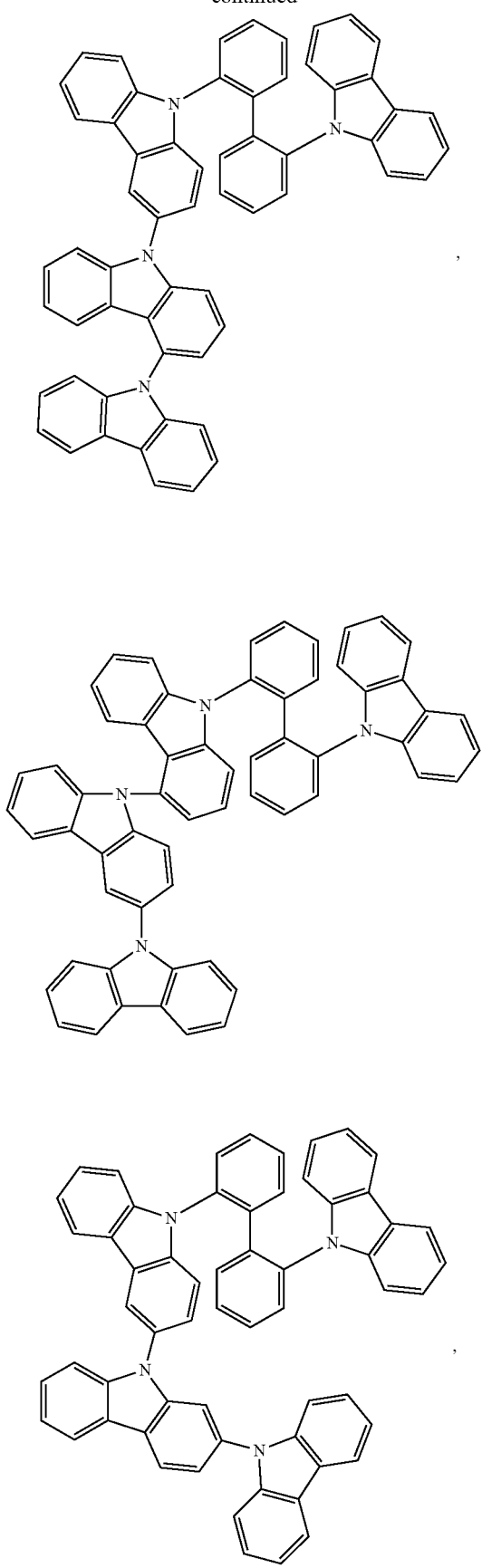
28
-continued
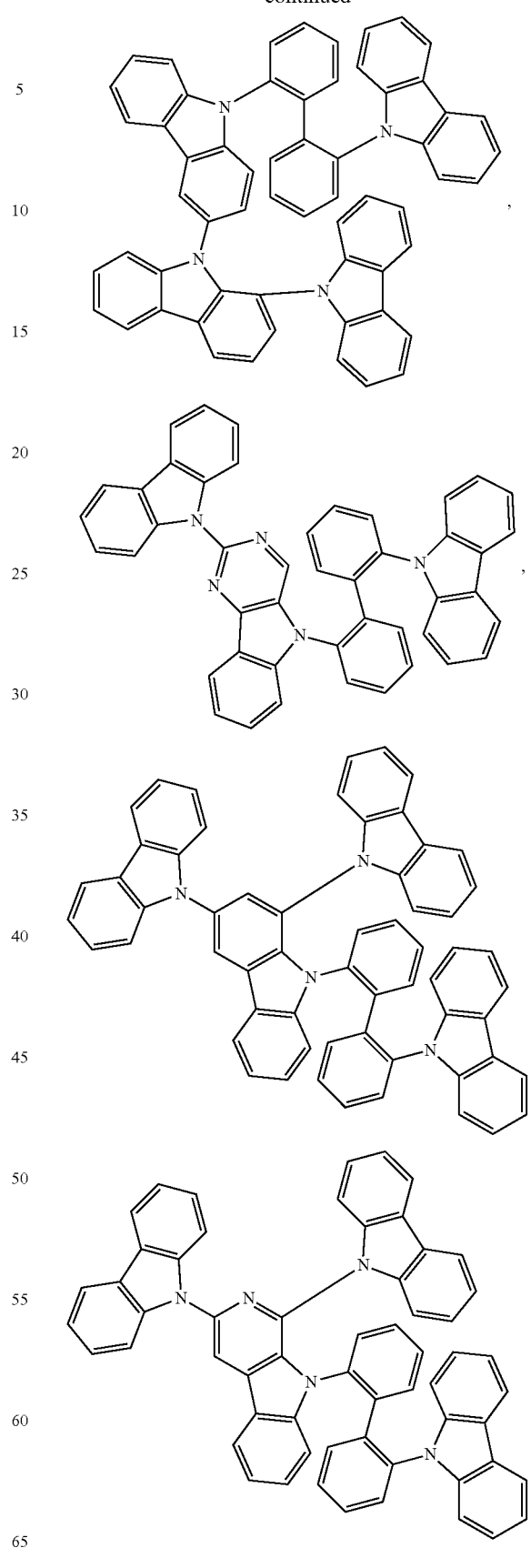

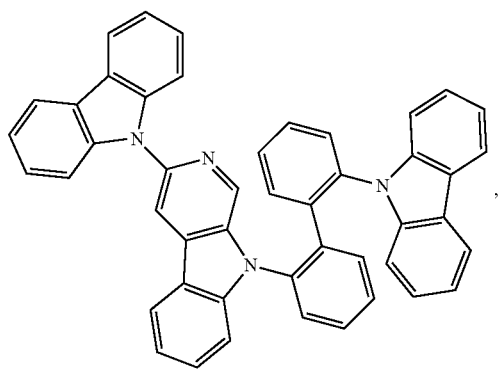
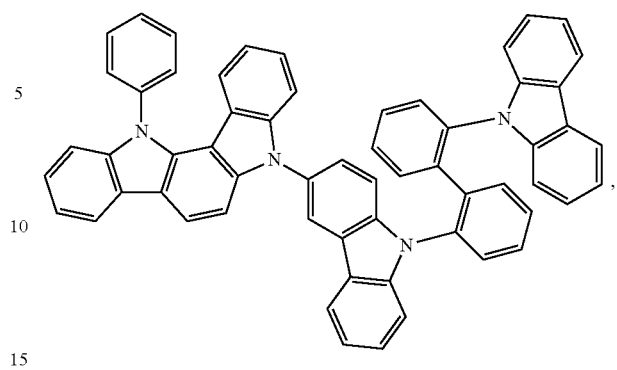
,
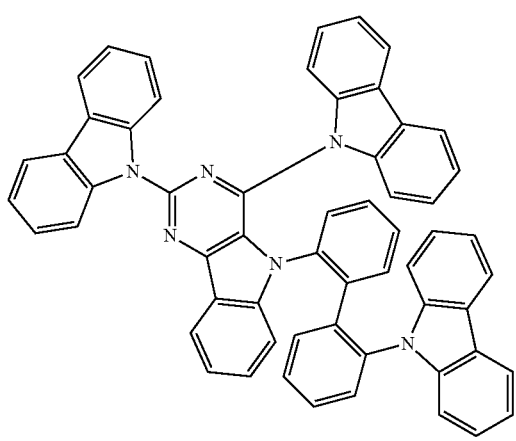
,
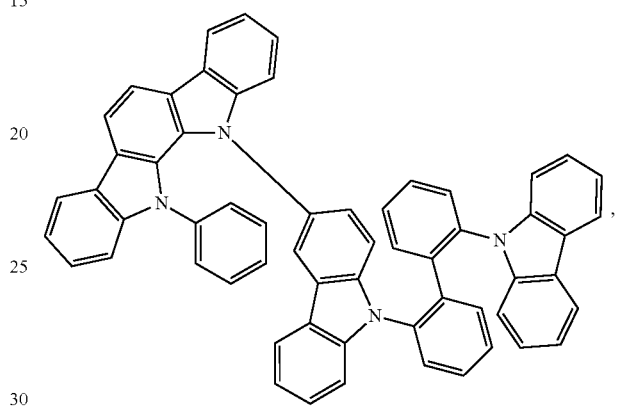
,
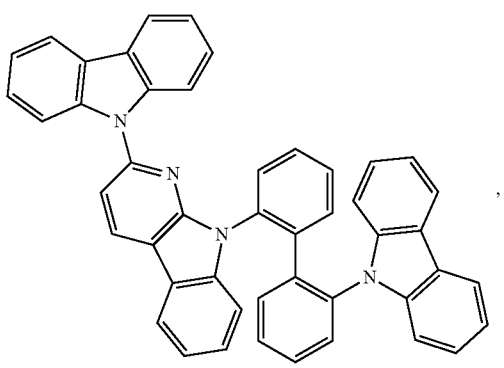
,
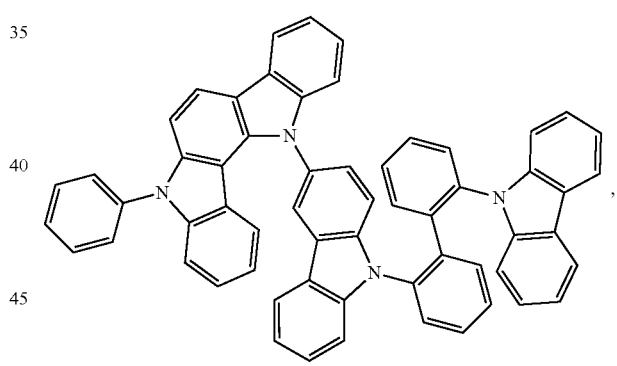
,
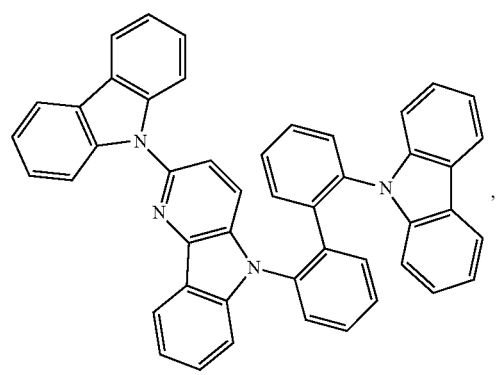
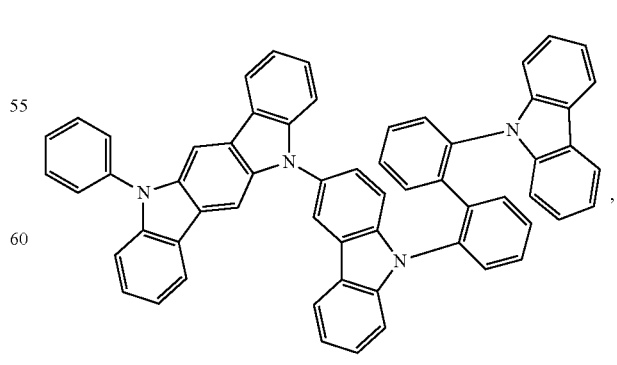
,

31
-continued
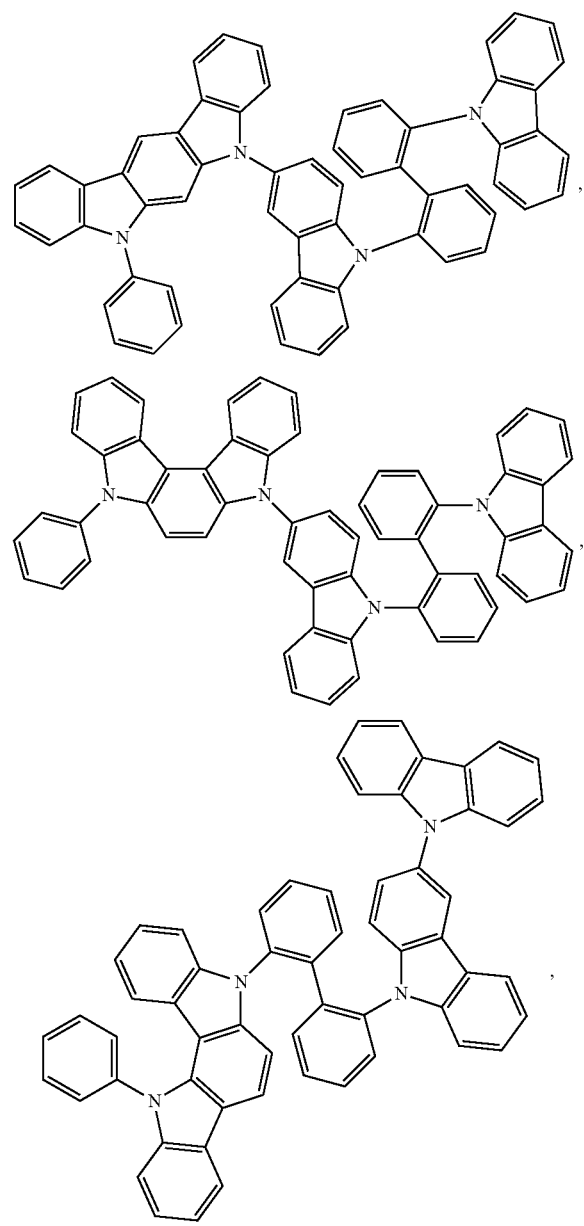
32
-continued
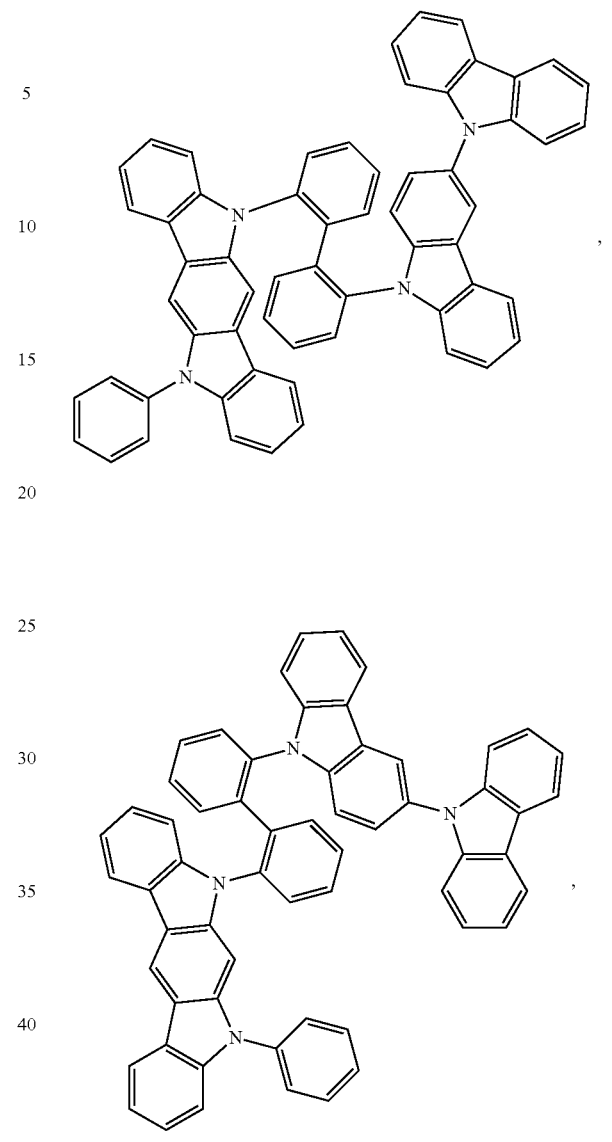
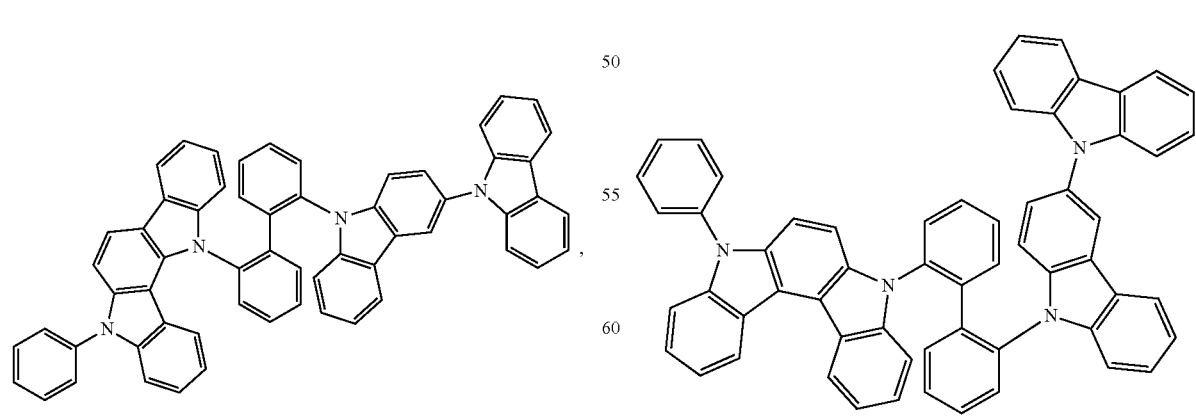

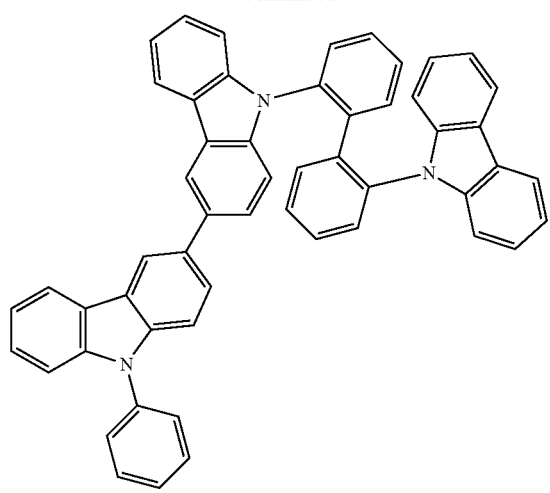

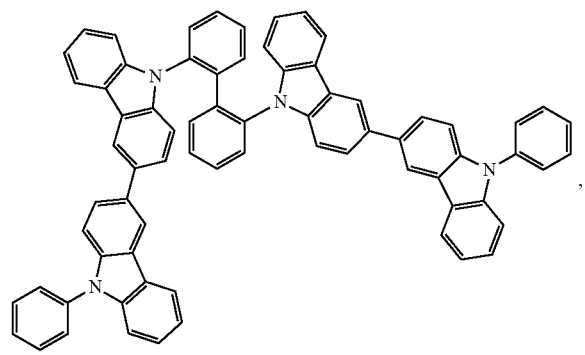

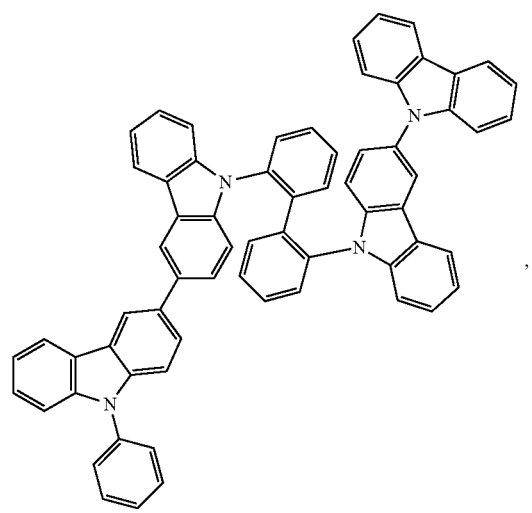

, and

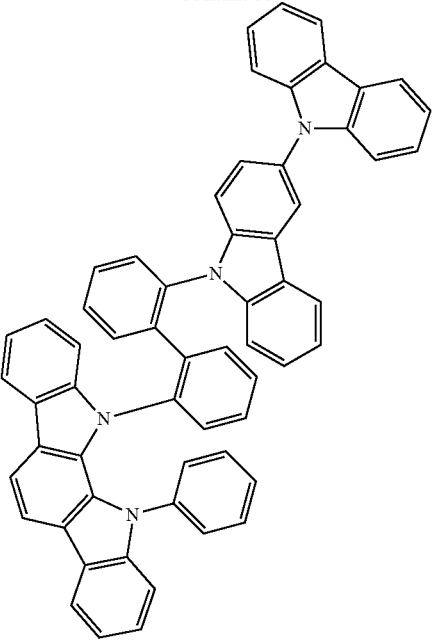

C. The OLEDs and the Devices of the Present Disclosure

In another aspect, the present disclosure also provides an OLED comprising a first organic layer that contains a compound as disclosed in the above compounds section of the present disclosure.

In some embodiments, In one aspect, the first organic layer may further comprise a second compound comprising a chemical structure selected from the group consisting of triazine, pyrimidine, pyridines, 9-dioxa-13b-boranaphtho[3,2,1-de]anthracene, aza-naphthalene, aza-fluorene, aza-triphenylene, aza-carbazole, aza-indolocarbazole, aza-dibenzothiophene, aza-dibenzofuran, and aza-dibenzoselenophene, and aza-(5,9-dioxa-13b-boranaphtho[3,2,1-de]anthracene).

In one aspect, the present disclosure provides that the second compound is selected from the group consisting of:

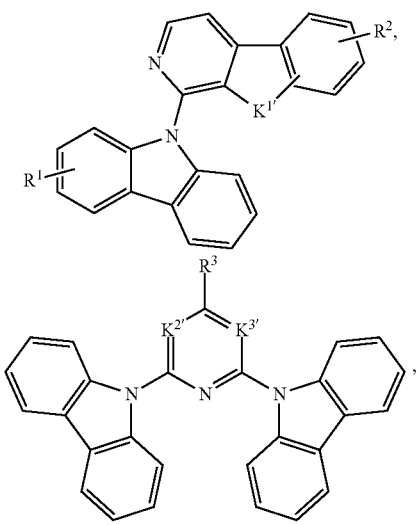

-continued

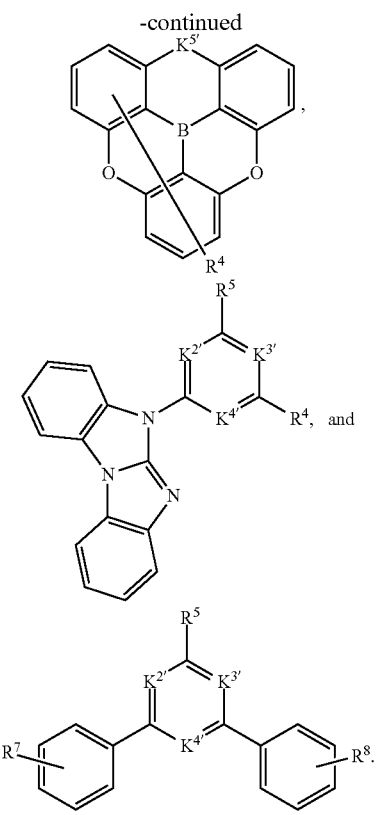

wherein
- $K^{1'}$ is O or S;
- $K^{2'}$, $K^{3'}$, and are N or $CR^9$;
- $K^{5'}$ is selected from the group consisting of O, S and $NR^{10}$; and
- $R^1$, $R^2$, $R^3$, $R^4$, $R^5$, $R^6$, $R^7$, $R^8$, $R^9$ and $R^{10}$ are independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In one aspect, the present disclosure provides that the second compound is selected from the group consisting of:

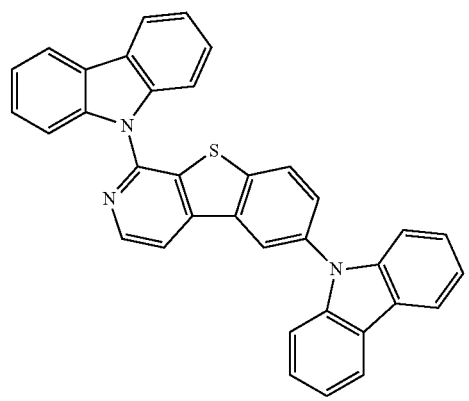

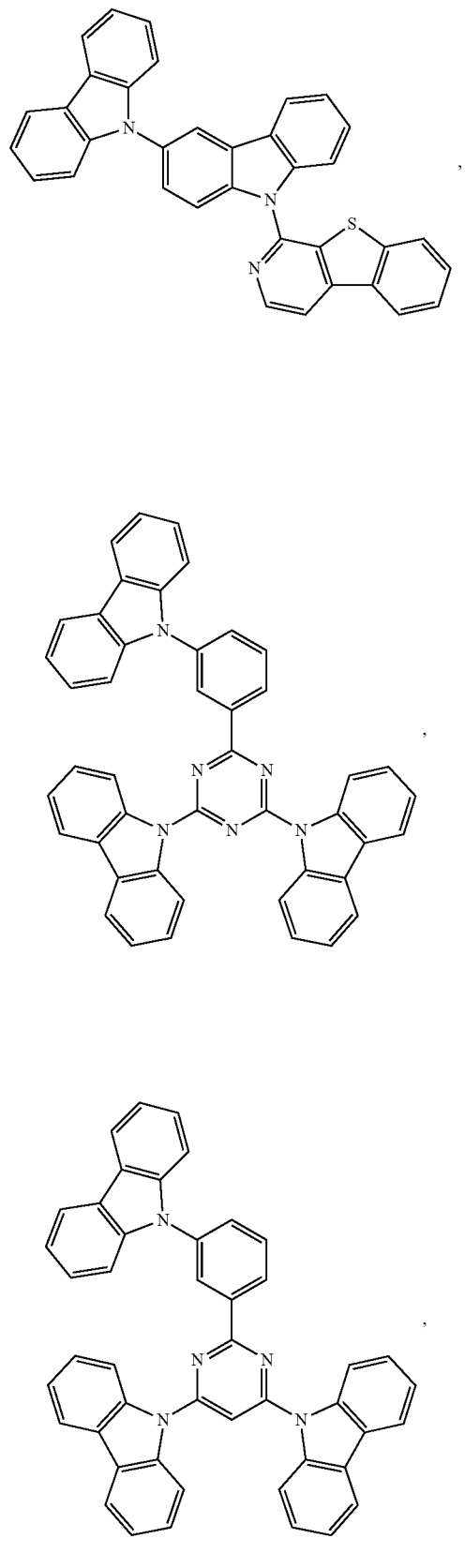

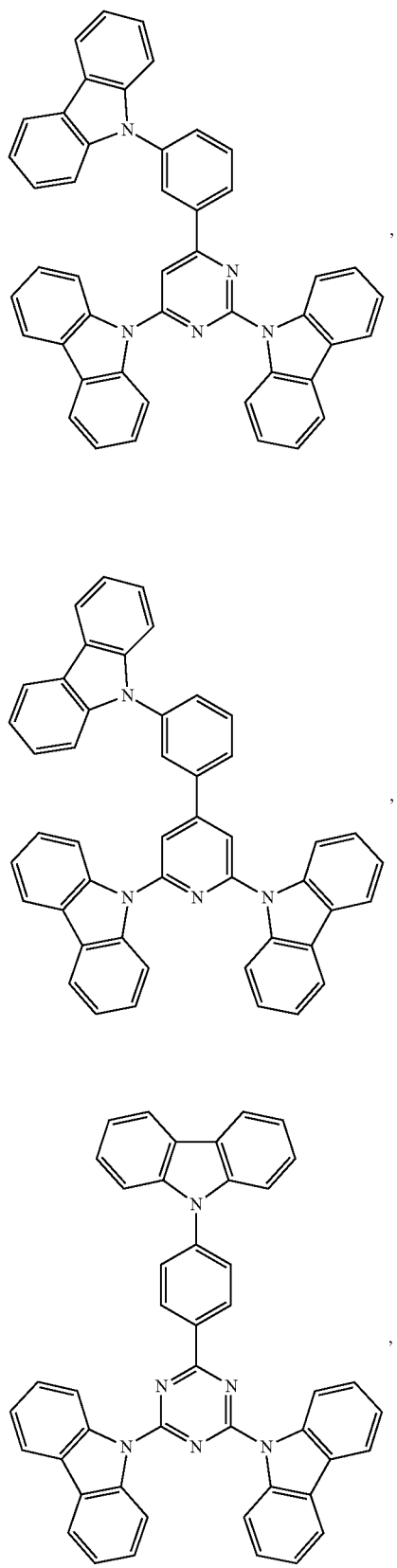
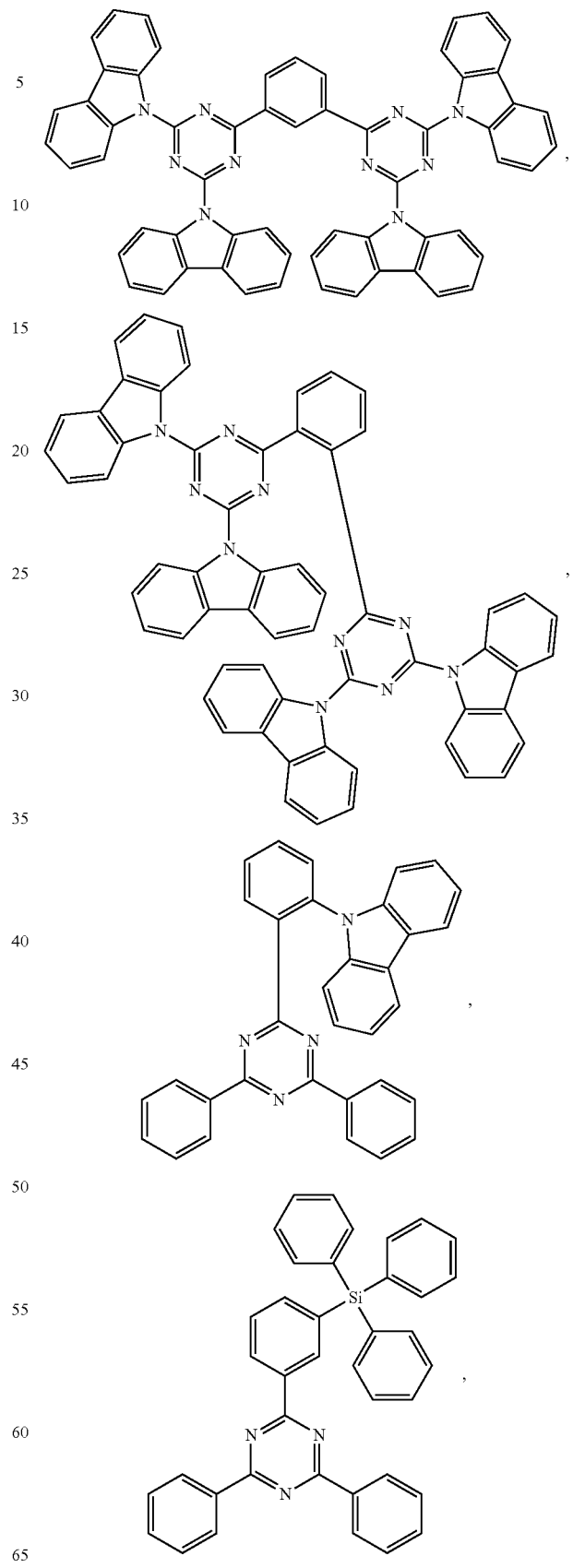

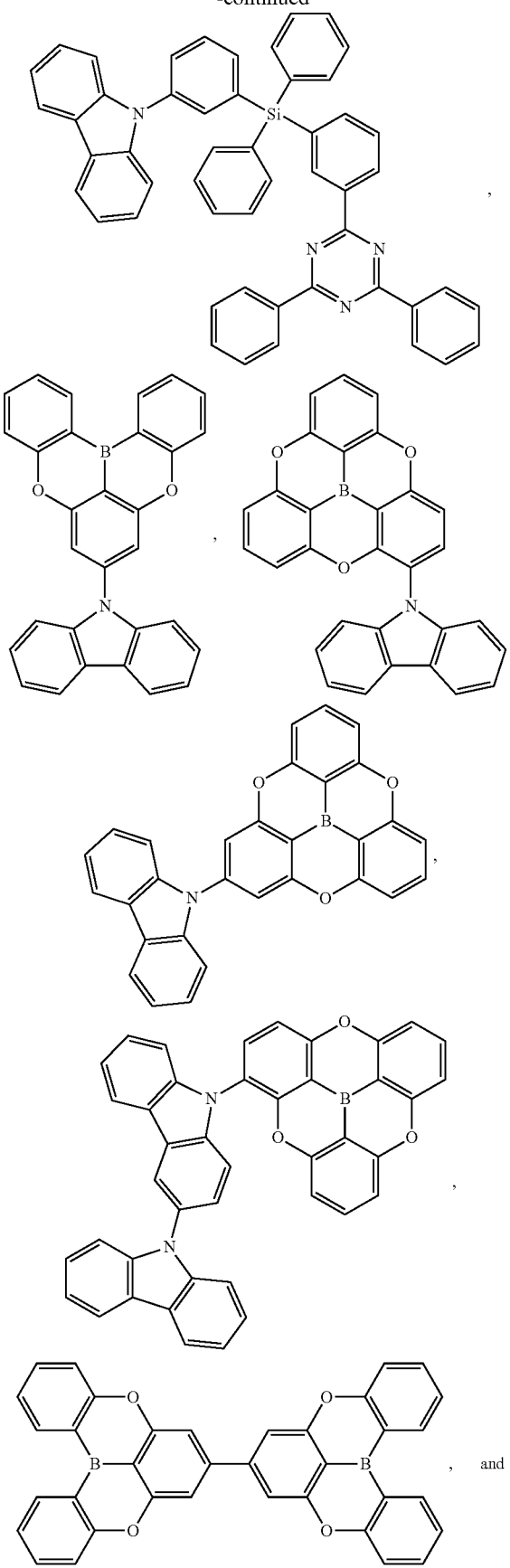

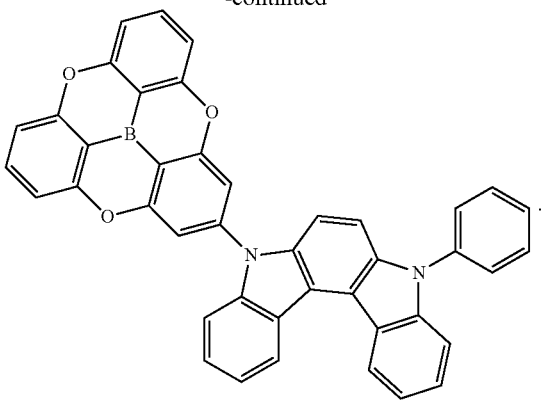

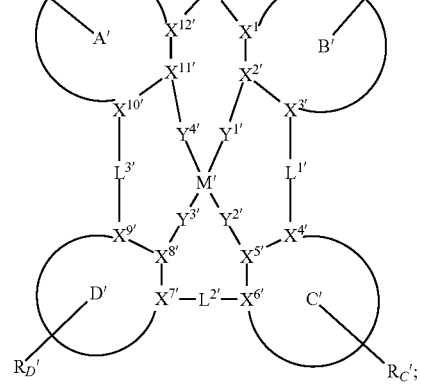

In one aspect, the first organic layer in the OLED can further comprise a compound of Formula II $$\text{[Formula II structure]}$$

wherein
M' is Pt or Pd;
rings A', B', C', and D' each independently represent a 5-membered or 6-membered carbocyclic or heterocyclic ring;
$X^{1'}$-$X^{12'}$ are each independently selected from the group consisting of carbon and nitrogen;
$R_{A'}$, $R_{B'}$, $R_{C'}$, and $R_{D'}$ each independently represents mono to the maximum allowed number of substitutions, or no substitution;
each $R_{A'}$, $R_{B'}$, $R_{C'}$, and $R_{D'}$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
n' is 0 or 1;
$L^{1'}$, $L^{2'}$, and $L^{3'}$ are each independently selected from the group consisting of a direct bond, BRR', NR, PR, O, S, Se, C=O, S=O, $SO_2$, CRR', SiRR', GeRR', and combinations thereof;
when n' is 1, $L^{4'}$ is selected from the group consisting of a direct bond, BRR', NR, PR, O, S, Se, C=O, S=O, $SO_2$, CRR', SiRR', GeRR', and combinations thereof;
when n' is 0, $L^{4'}$ is not present;

each $Y^{1'}$, $Y^{2'}$, $Y^{3'}$ and is selected from the group consisting of a direct bond, O, and S;

wherein at least two of $Y^{1'}$, $Y^{2'}$, $Y^{3'}$ and is a direct bond.

In one aspect, the present disclosure provides that the compound of Formula II in the first organic layer is a tetradentate Pt complex that has at least one part of the ligand selected from the group consisting of:

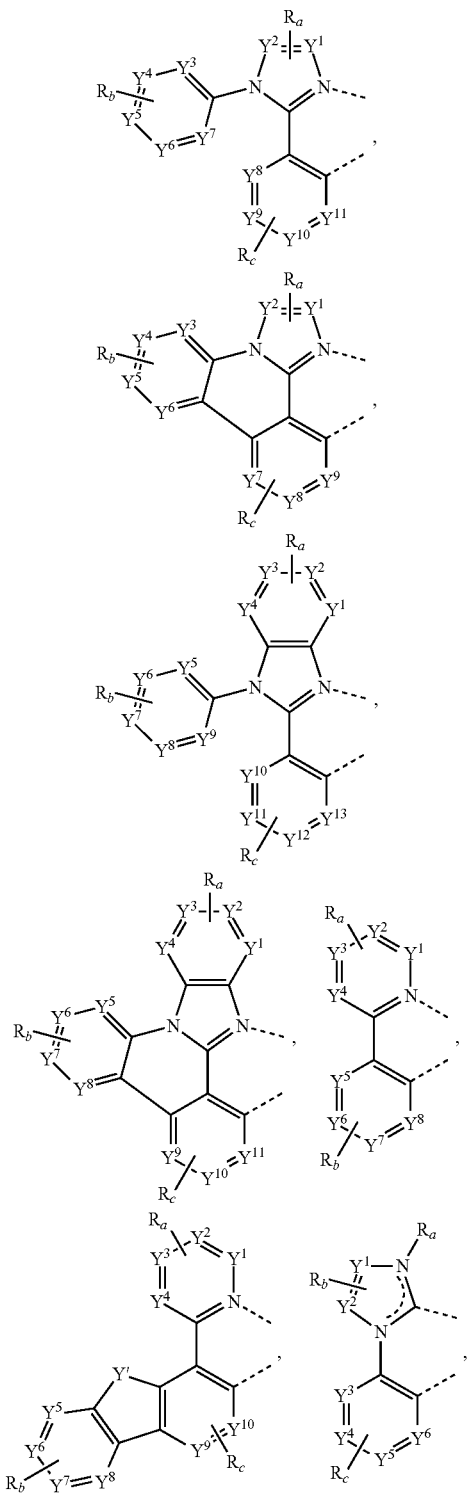

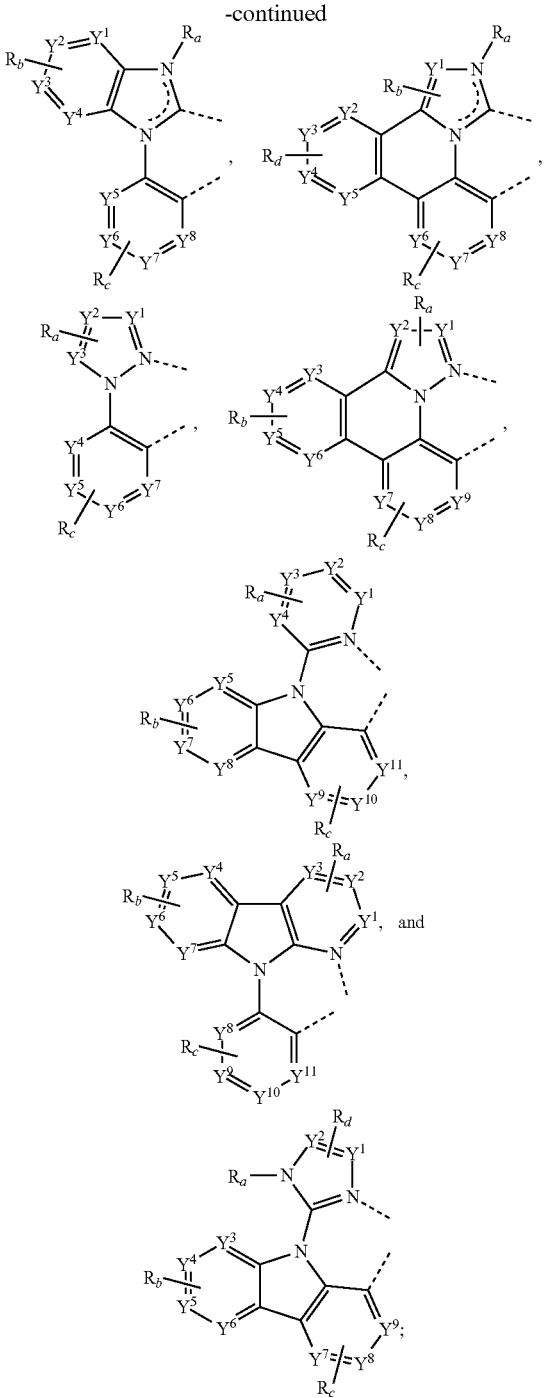

wherein each $Y^1$ to $Y^{13}$ are independently selected from the group consisting of carbon and nitrogen;

wherein Y' is selected from the group consisting of $BR_e$, $NR_e$, $PR_e$, O, S, Se, C=O, S=O, $SO_2$, $CR_eR_f$, $SiR_eR_f$, and $GeR_eR_f$;

wherein $R_e$ and $R_f$ are optionally fused or joined to form a ring;

wherein each $R_a$, $R_b$, $R_c$, and $R_d$ may independently represent from mono substitution to the maximum possible number of substitution, or no substitution;

wherein each $R_a$, $R_b$, $R_c$, $R_d$, $R_e$ and $R_f$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring.

In one aspect, the present disclosure provides that the compound of Formula II in the first organic layer is selected from the group consisting of:

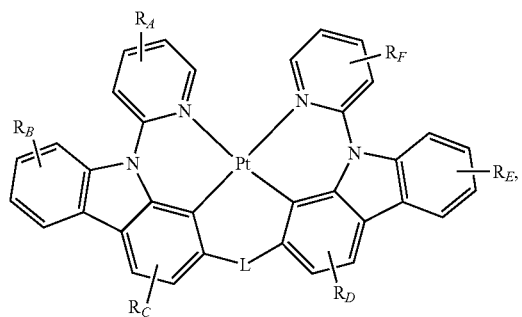

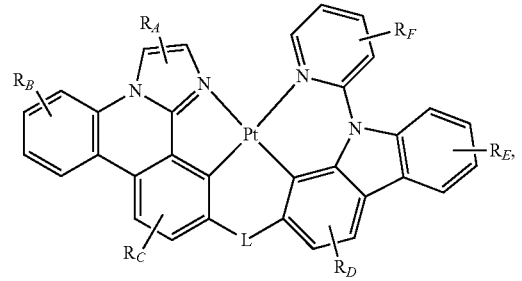

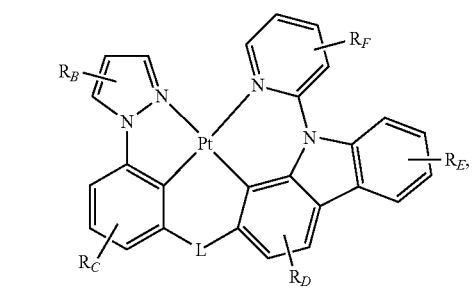

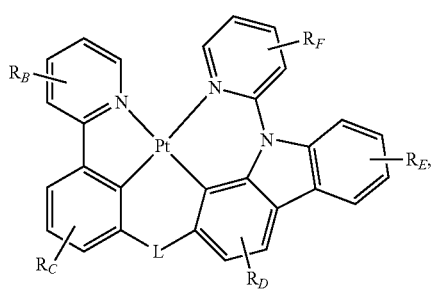

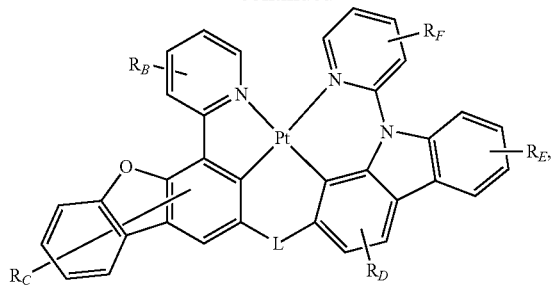

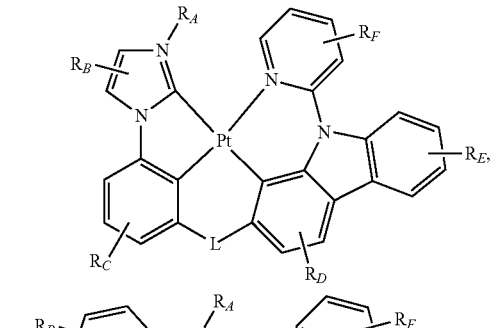

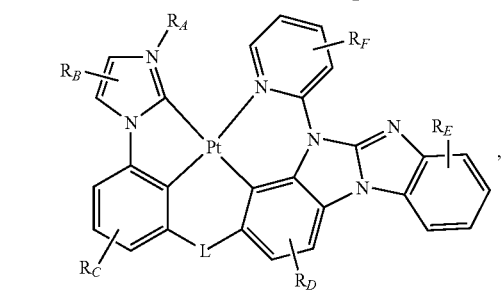

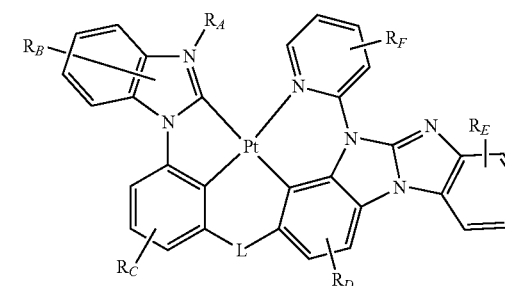

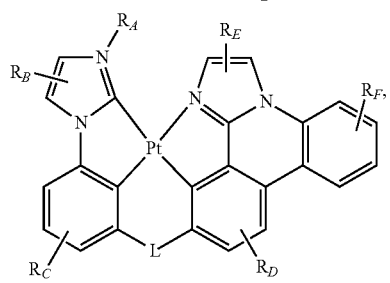

-continued

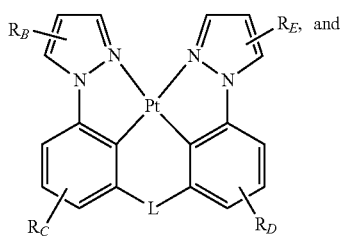

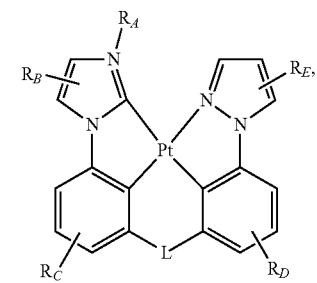

wherein L is selected form the group consisting of O, S, Se, NR, BR, BRR', C=O, S=O, CRR', SiRR', and combinations thereof; and each $R_A$, $R_B$, $R^C$, $R_D$, $R_E$, and $R_F$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some embodiments, the first organic layer may be an emissive layer and the compound as described herein may be an emissive dopant or a non-emissive dopant.

In some embodiments, the compound may be a fluorescent emitter.

In some embodiments, the first organic layer may further comprise a phosphorescent sensitizer, and the compound is a fluorescent acceptor.

In some embodiments, the OLED may comprise a second organic layer disposed between the anode and the cathode, wherein the second organic layer comprises a phosphorescent sensitizer, and the compound is a fluorescent acceptor.

In some embodiments, the phosphorescent sensitizer may be a transition metal complex having at least one ligand or part of the ligand if the ligand is more than bidentate selected from the group consisting of:

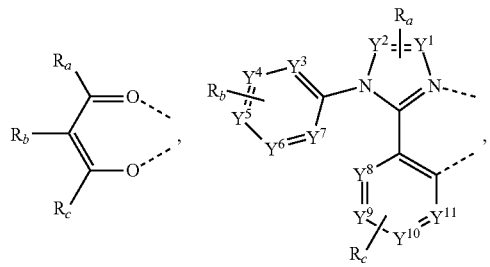

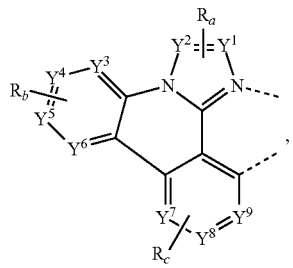

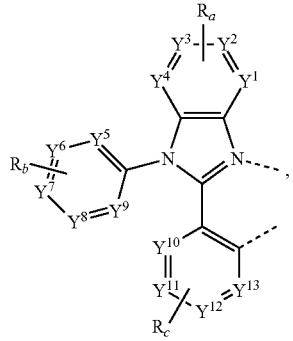

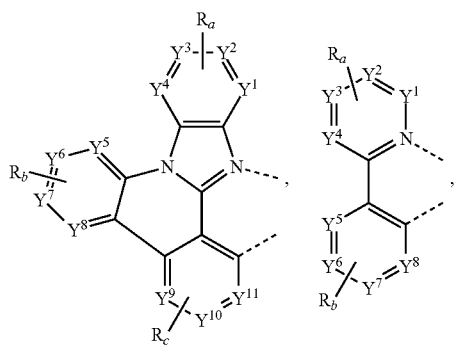

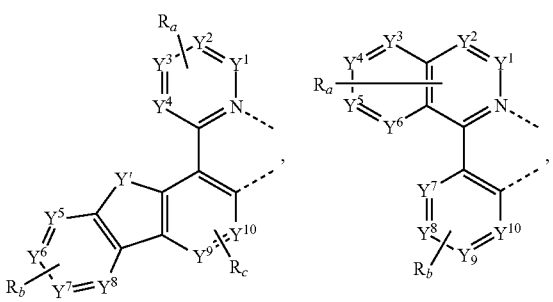

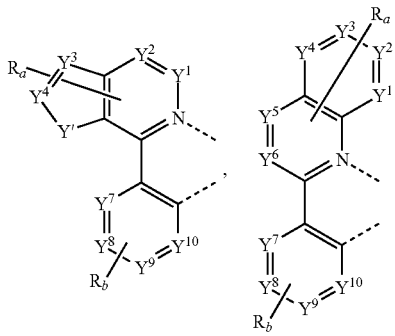

-continued

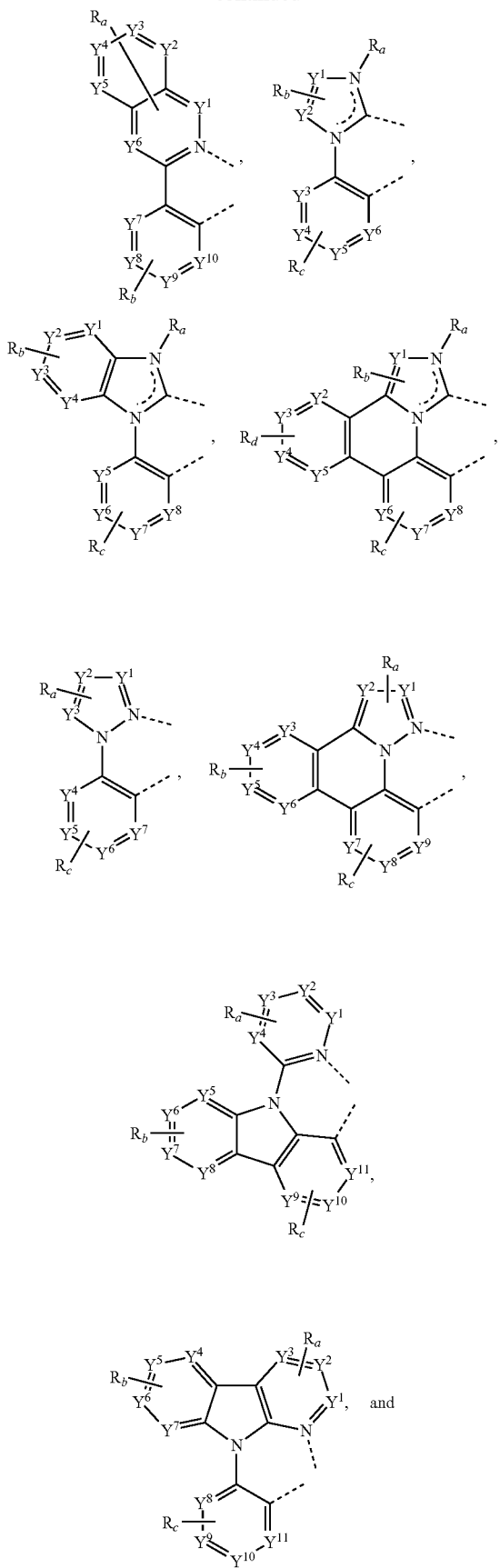

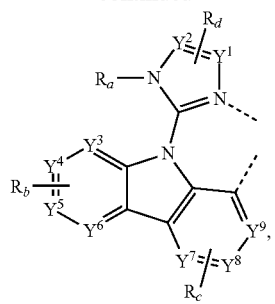

wherein each $Y^1$ to $Y^{13}$ are independently selected from the group consisting of carbon and nitrogen; Y' is selected from the group consisting of $BR_e$, $NR_e$, $PR_e$, O, S, Se, C=O, S=O, $SO_2$, $CR_eR_f$, $SiR_eR_f$, and $GeR_eR_f$; $R_e$ and $R_f$ are optionally fused or joined to form a ring; each $R_a$, $R_b$, $R_c$, and $R_d$ independently represent from zero, mono, or up to a maximum allowed substitution to its associated ring; $R_a$, $R_b$, $R_c$, $R_d$, $R_e$ and $R_f$ are each independently hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and two adjacent substituents of $R_a$, $R_b$, $R_c$, and $R_d$ are optionally fused or joined to form a ring or form a multidentate ligand.

In some embodiments, one or more organic layers, disposed between the anode and cathode, comprise a host, wherein the host comprises at least one chemical group selected from the group consisting of anthracene, naphthalene, triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

In some embodiments, the host may be selected from the HOST Group consisting of:

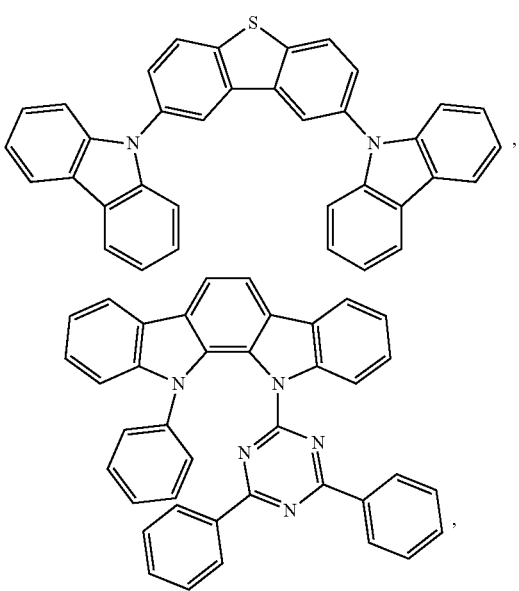

-continued
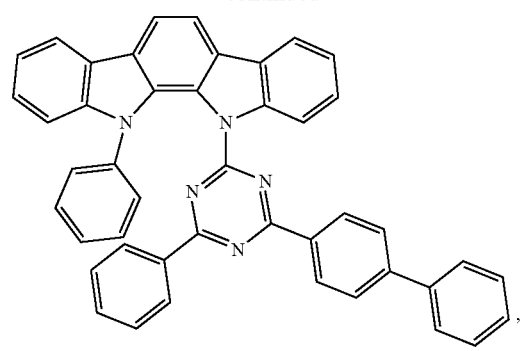
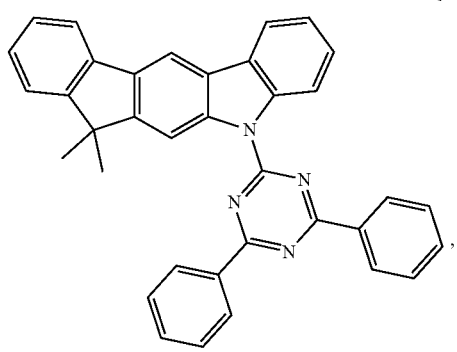
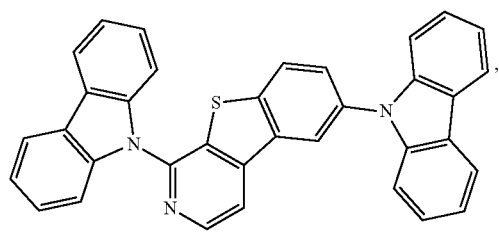
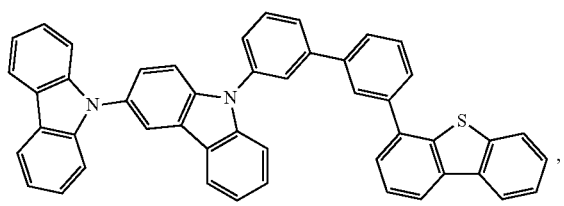
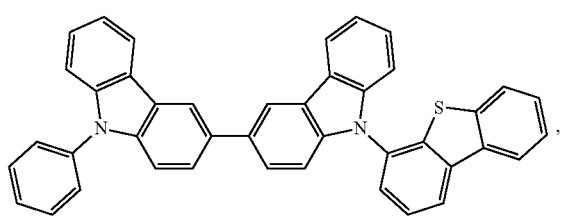
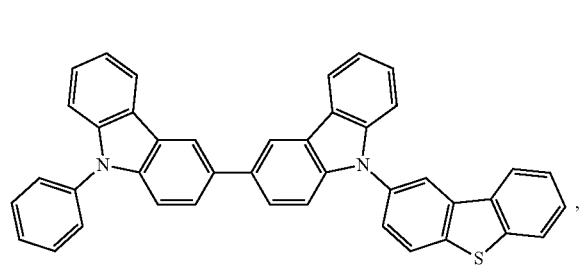
-continued
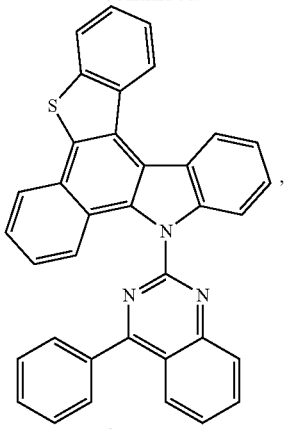
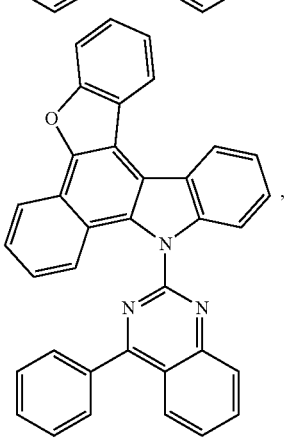
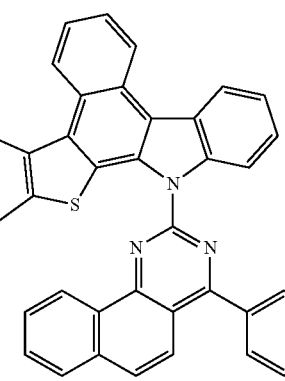
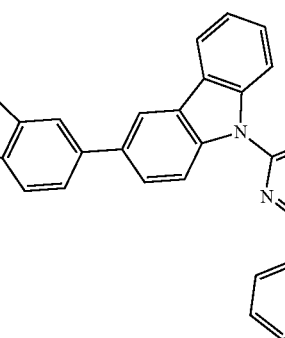

51
-continued
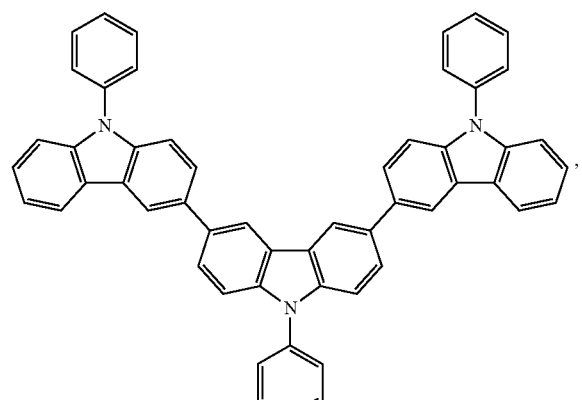
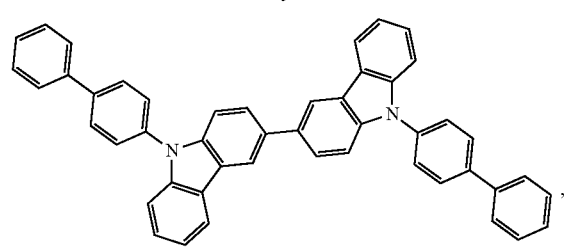
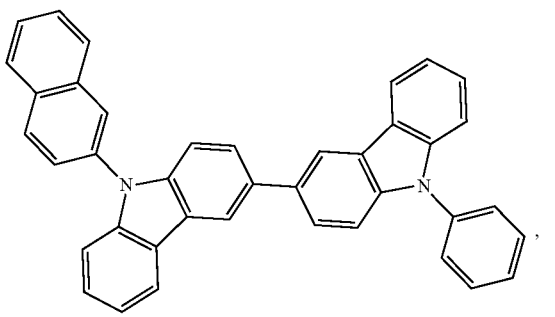
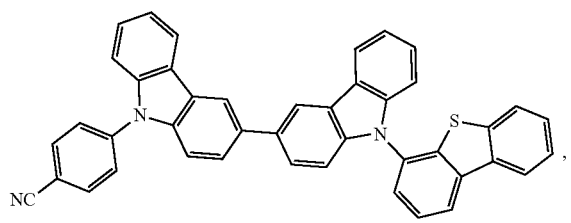
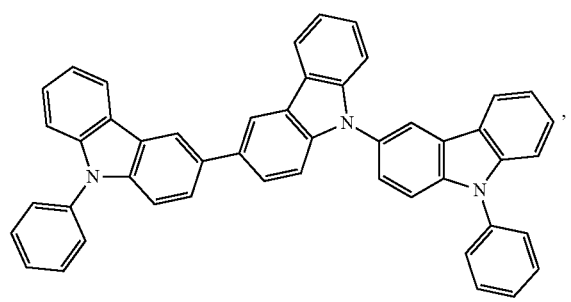
52
-continued
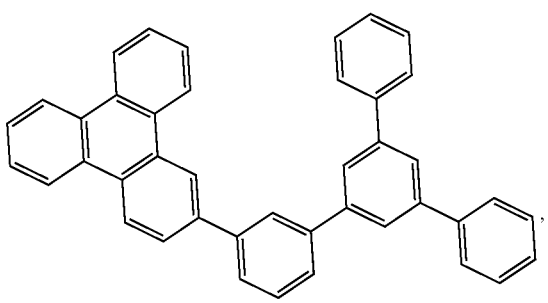
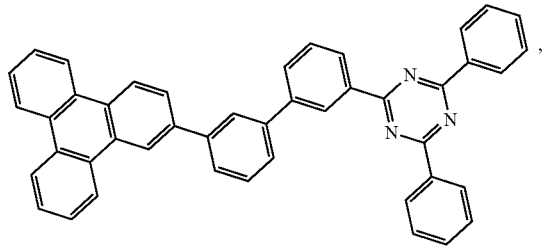
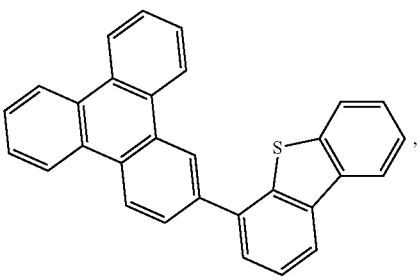
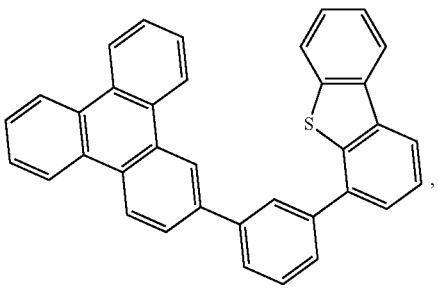
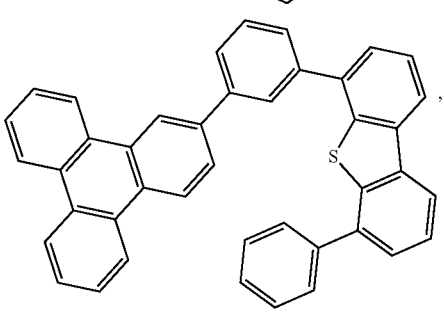
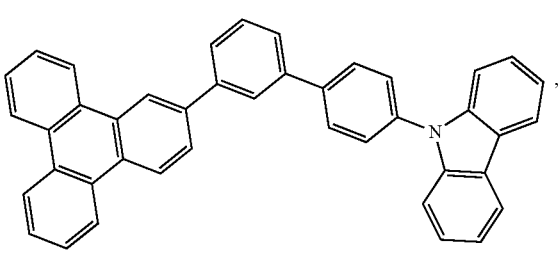

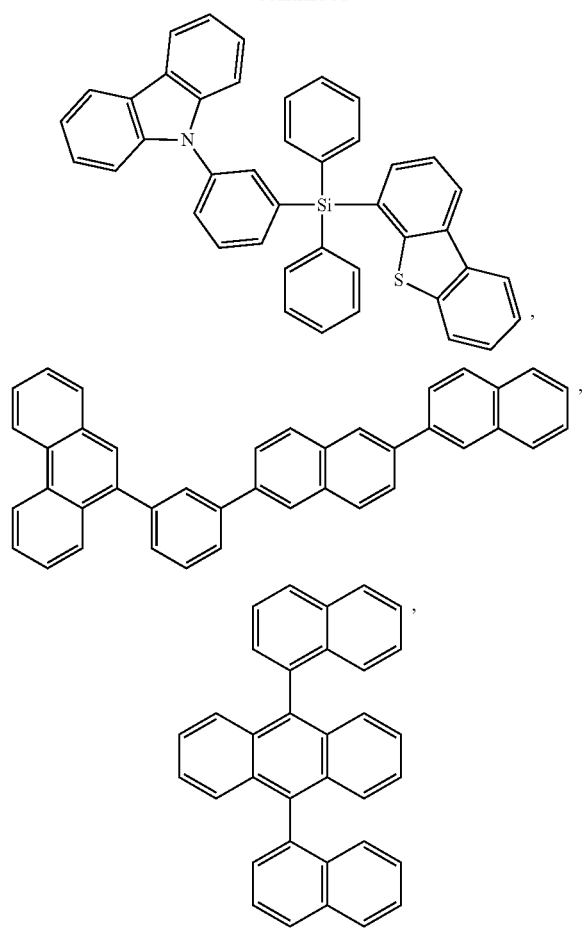
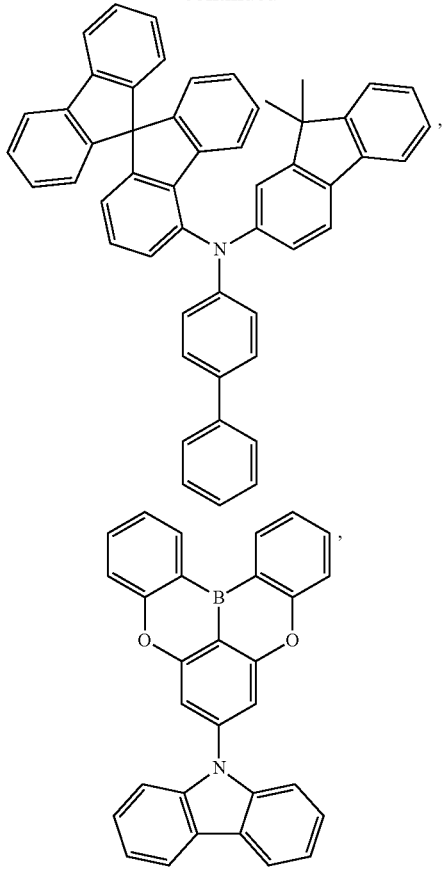
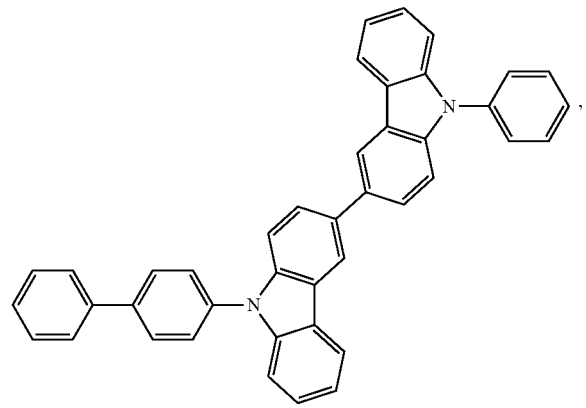
and combinations thereof.
In yet another aspect, the OLED of the present disclosure may also comprise an emissive region containing a compound as disclosed in the above compounds section of the present disclosure.
In some embodiments, the emissive region can comprise a compound comprising a structure of Formula I
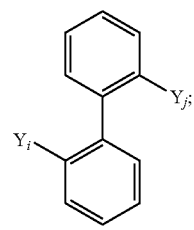
wherein: $Y_i$ is
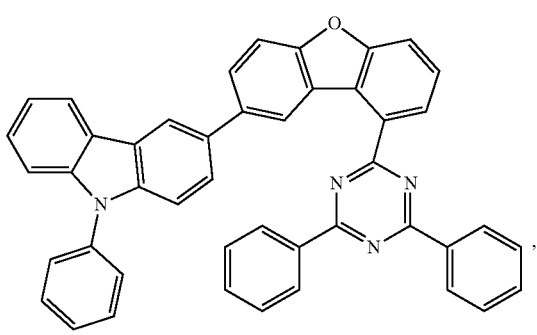
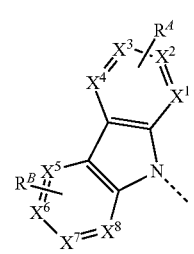

and $Y_j$ is

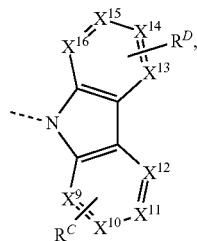

wherein:
$R^A$, $R^B$, $R^C$, and $R^D$ each independently represents zero, mono, di-substitution or the maximum allowable substitution;

each $R^A$, $R^B$, $R^C$, and $R^D$ is independently a hydrogen or a substituent selected from the group consisting of the general substituents defined herein;

at least one of $R^A$, $R^B$, $R^C$, and $R^D$ comprises a carbazole moiety;

each of $X^1$-$X^{16}$ is independently C or N; and any two substituents can be joined or fused together to form a ring.

In yet another aspect, the present disclosure also provides a consumer product comprising an organic light-emitting device (OLED) having an anode; a cathode; and an organic layer disposed between the anode and the cathode, wherein the organic layer may comprise a compound as disclosed in the above compounds section of the present disclosure.

In some embodiments, the consumer product comprises an organic light-emitting device (OLED) having an anode; a cathode; and an organic layer disposed between the anode and the cathode, wherein the organic layer can comprise a compound comprising a structure of Formula I

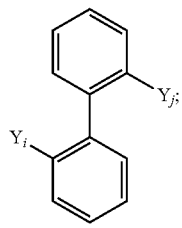

wherein: $Y_i$ is

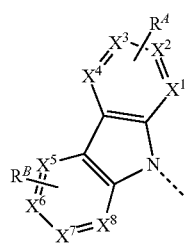

and $Y_j$ is

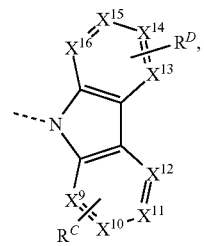

wherein:
$R^A$, $R^B$, $R^C$, and $R^D$ each independently represents zero, mono, di-substitution or the maximum allowable substitution;

each $R^A$, $R^B$, $R^C$, and $R^D$ is independently a hydrogen or a substituent selected from the group consisting of the general substituents defined herein;

at least one of $R^A$, $R^B$, $R^C$, and $R^D$ comprises a carbazole moiety;

each of $X^1$-$X^{16}$ is independently C or N; and any two substituents can be joined or fused together to form a ring.

In some embodiments, the consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
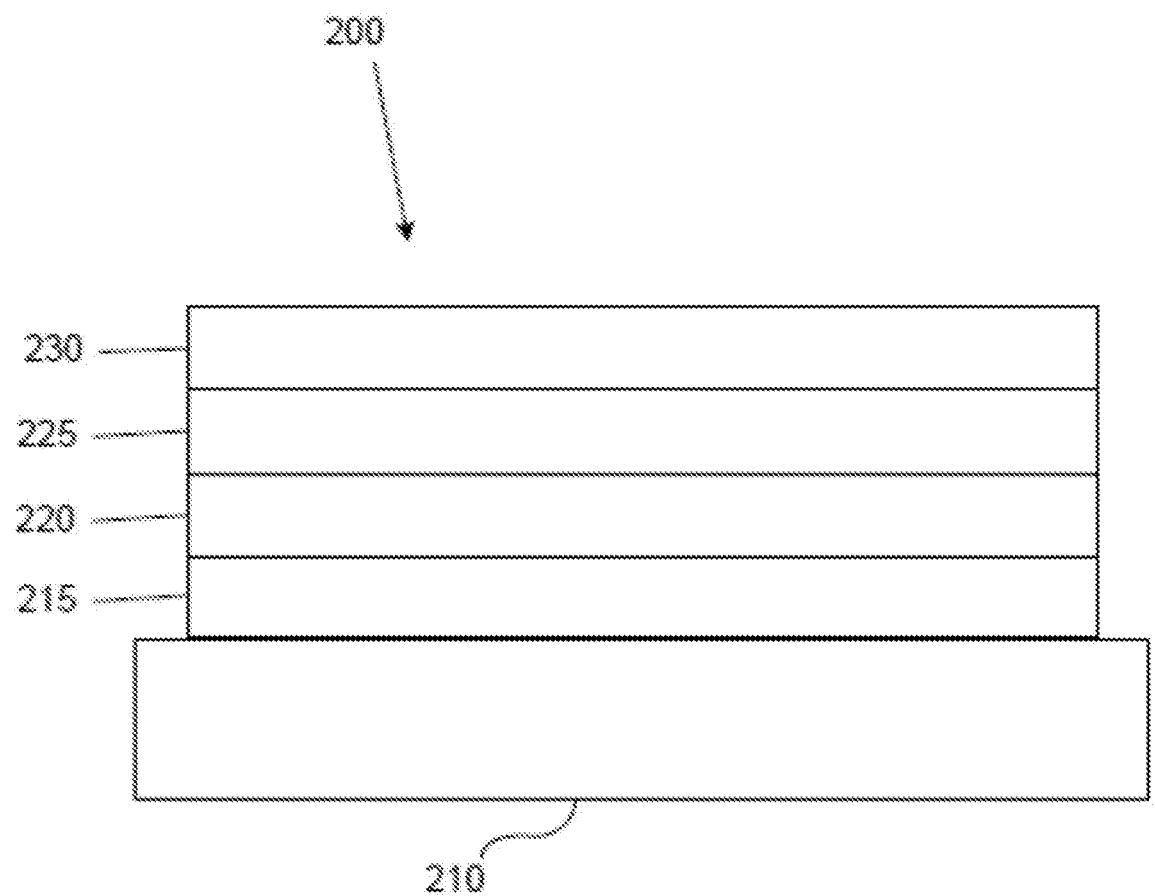
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18° C. to 30° C., and more preferably at room temperature (20-25° C.), but could be used outside this temperature range, for example, from −40° C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands Thus, where the coordinating ligands are being linked together, all of the ligands can be the same in some embodiments, and at least one of the ligands being linked can be different from the other ligand(s) in some other embodiments.

In some embodiments, the compound can be used as one component of an exciplex to be used as a sensitizer.

In some embodiments, the sensitizer is a single component, or one of the components to form an exciplex.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

D. Combination of the Compounds of the Present Disclosure with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

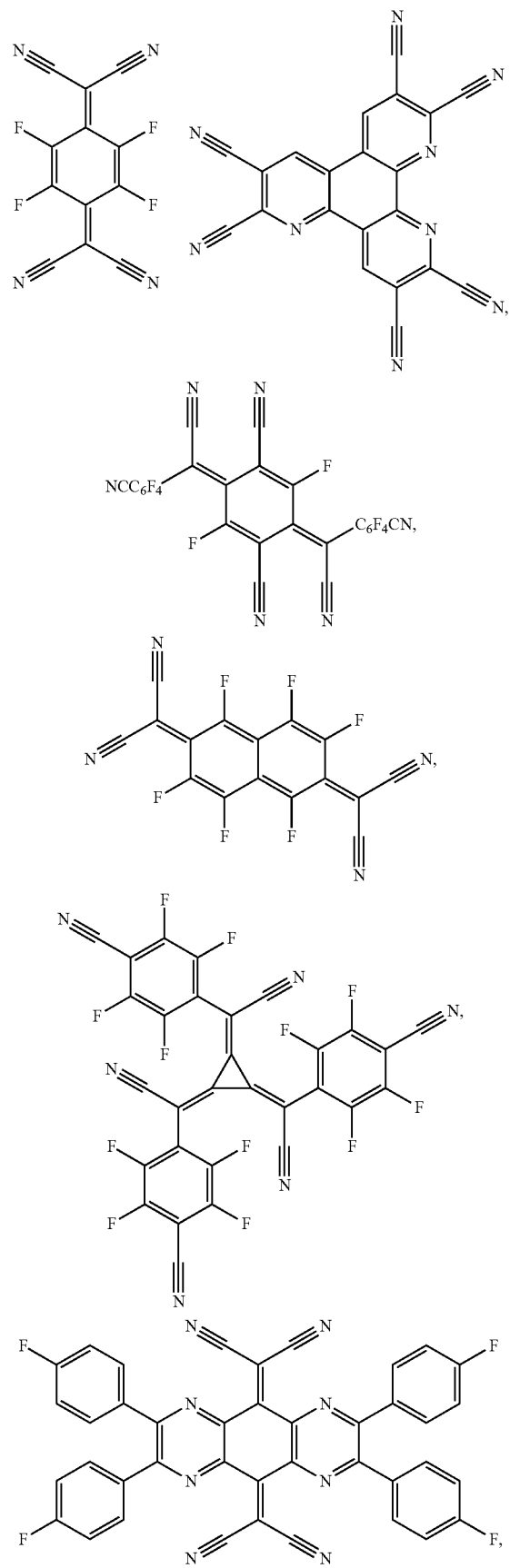

-continued

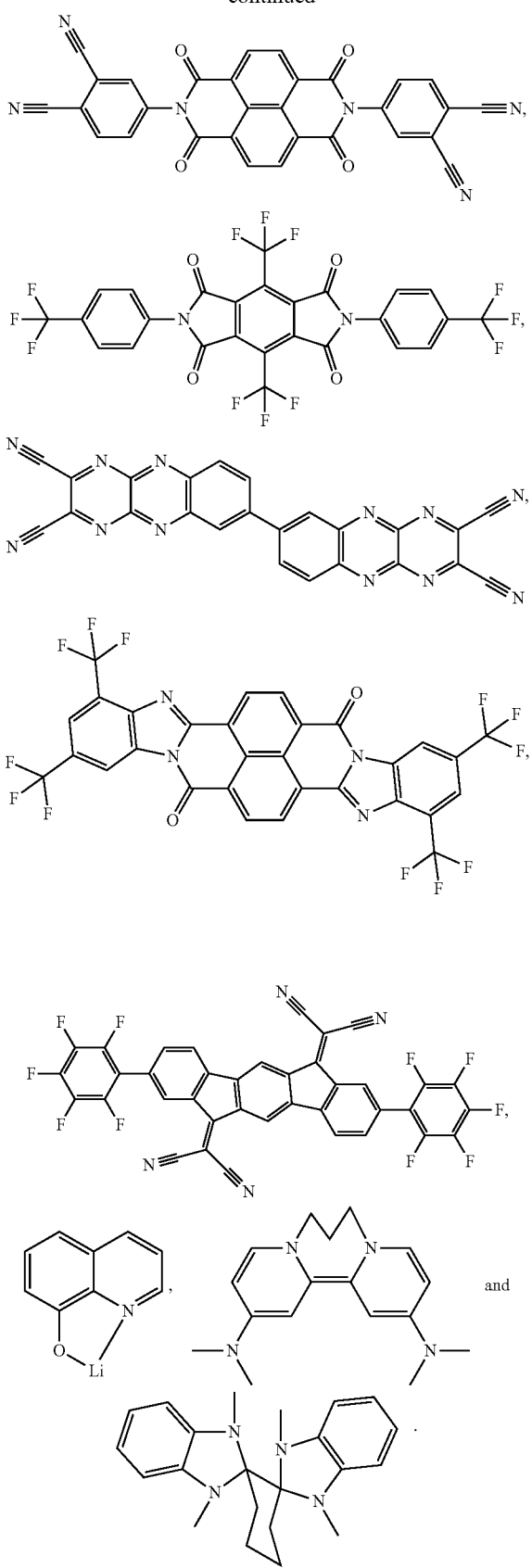

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphoric acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

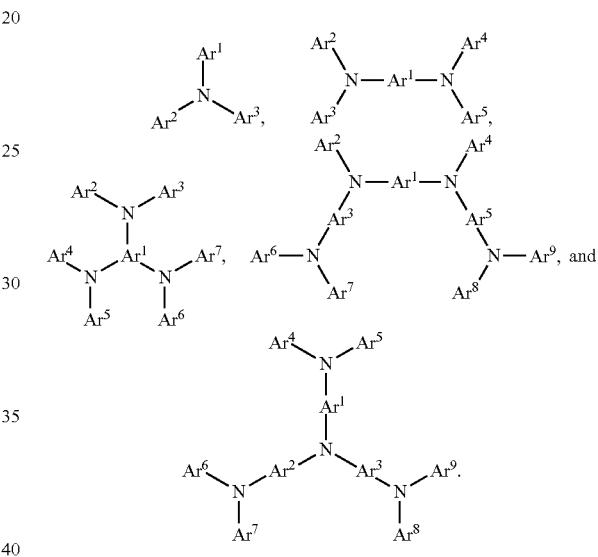

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

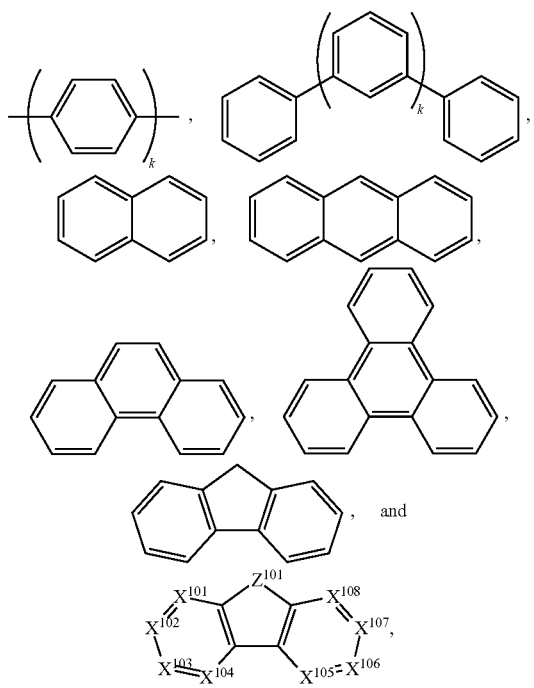

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

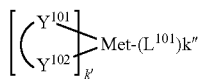

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

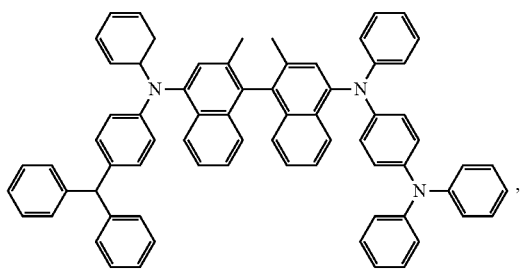

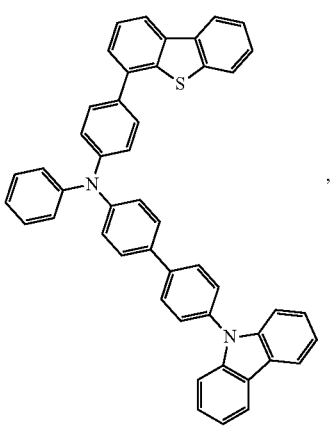

-continued
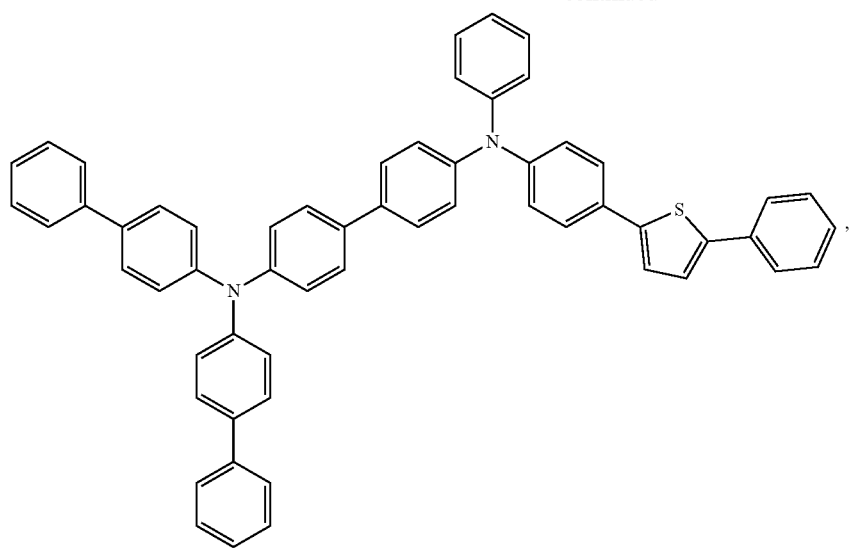
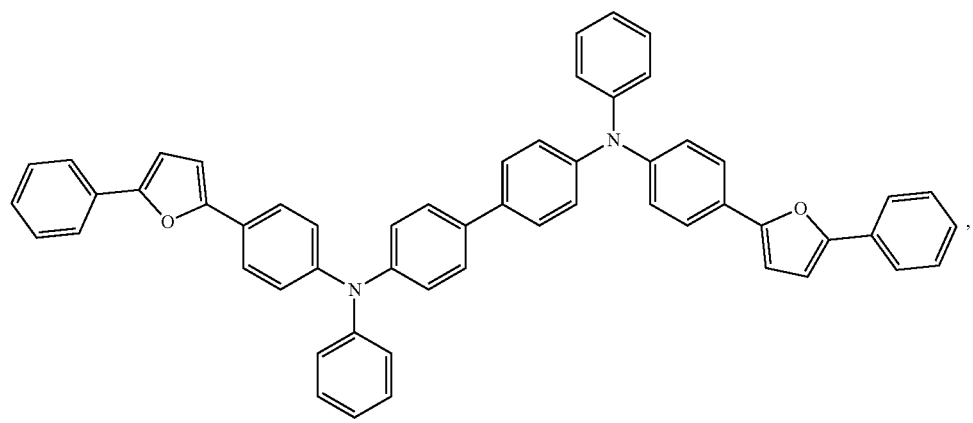
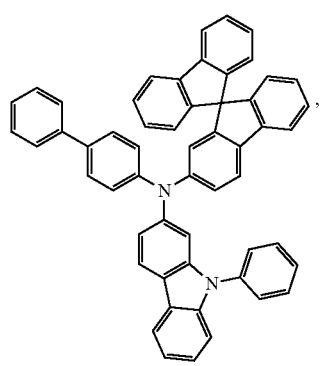
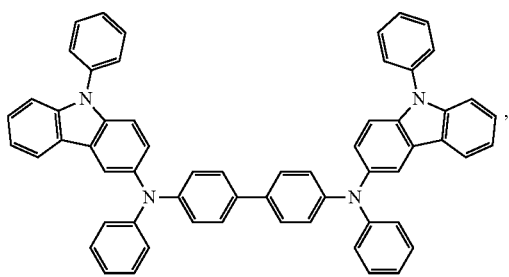

-continued
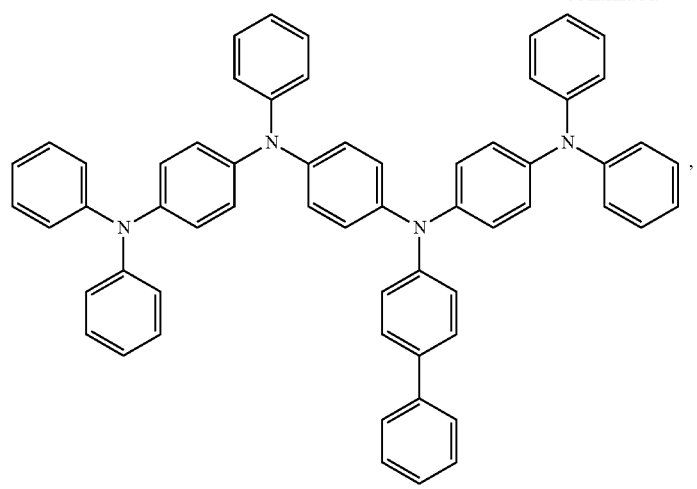
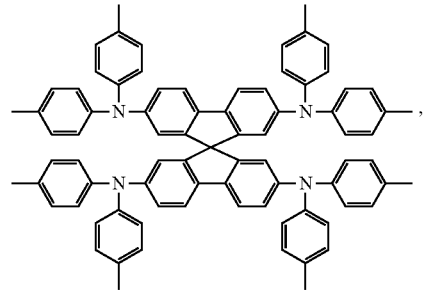
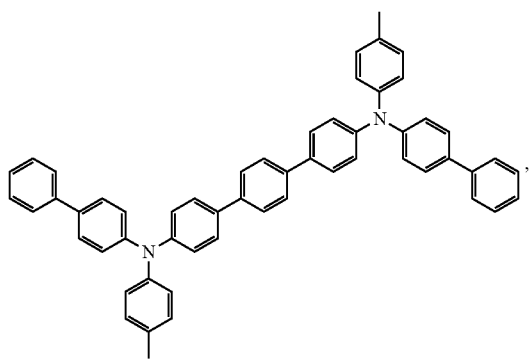
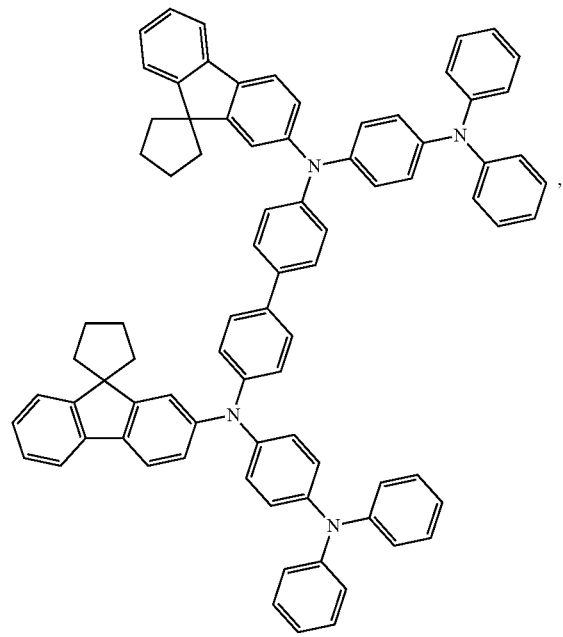

-continued
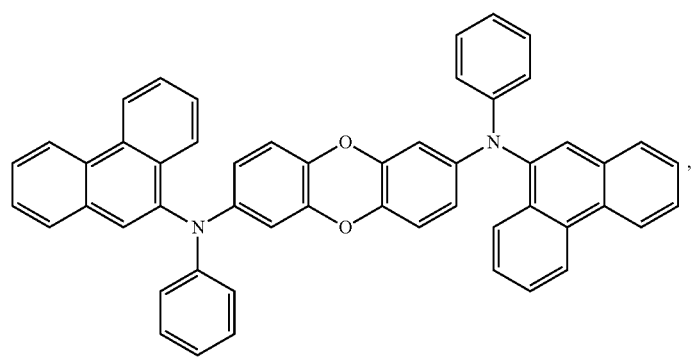
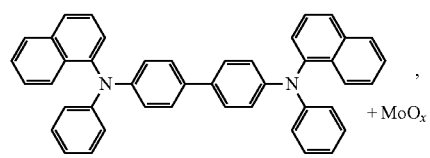
+MoOx
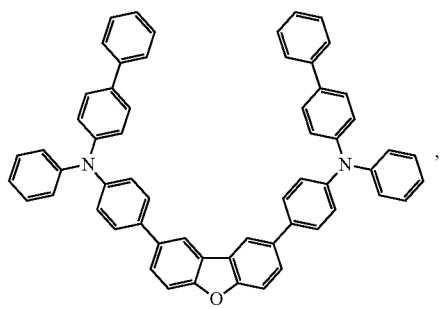
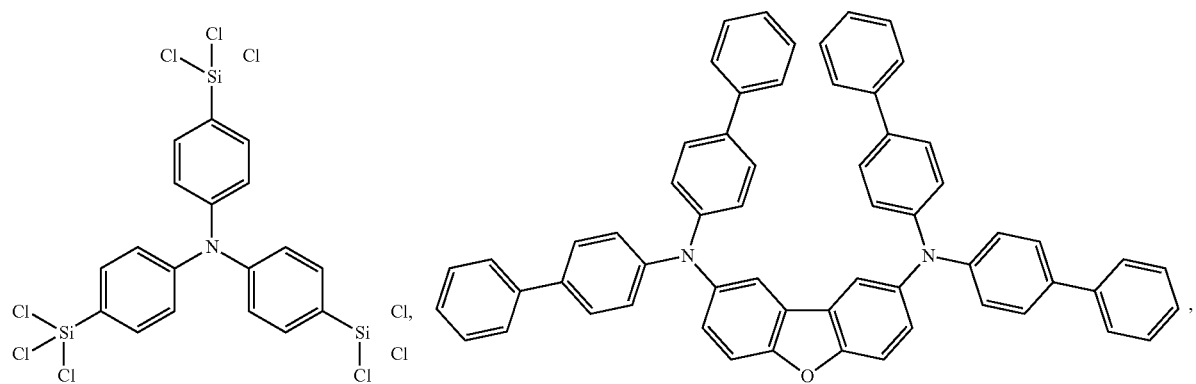
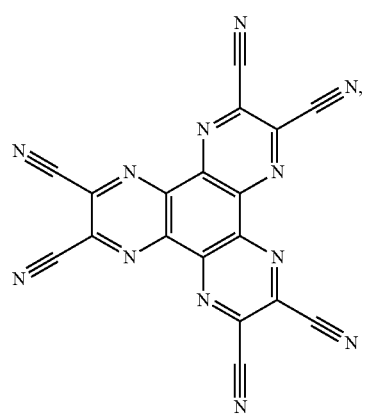

-continued
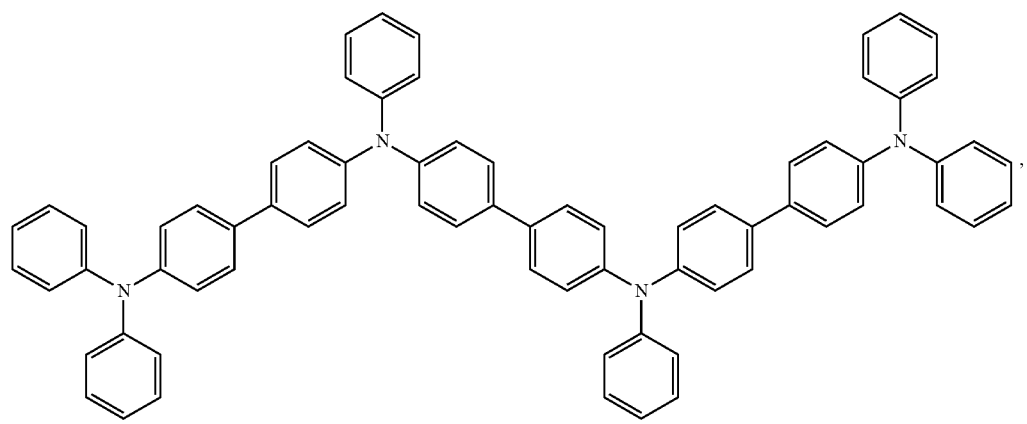
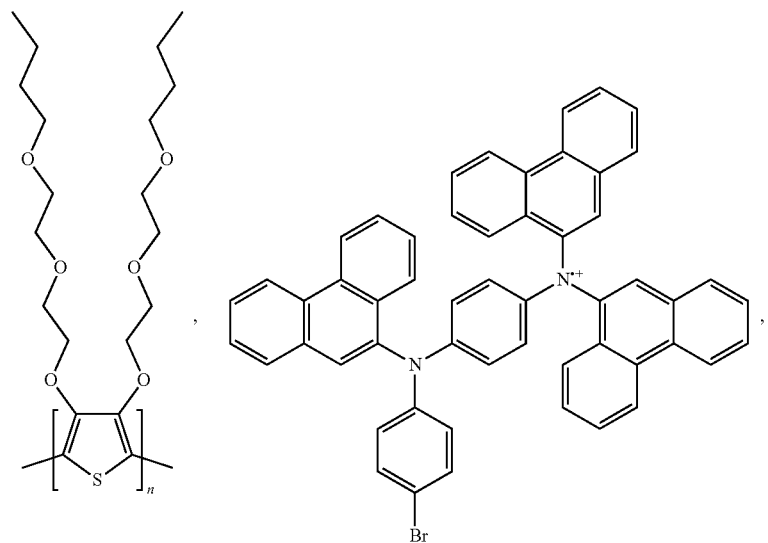
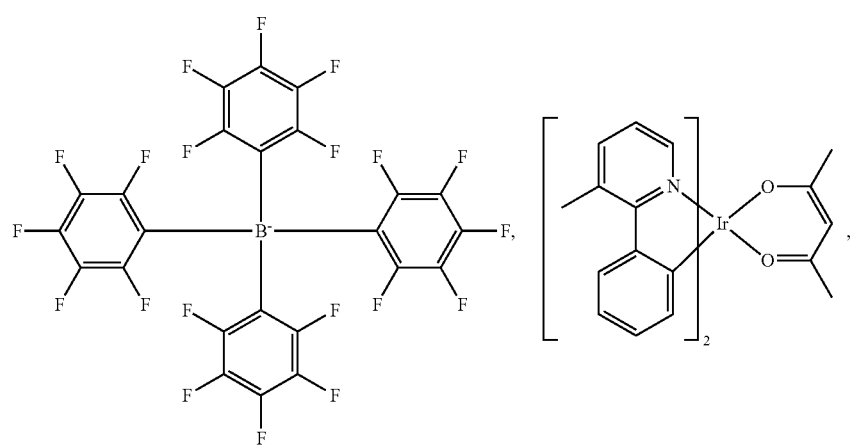

-continued
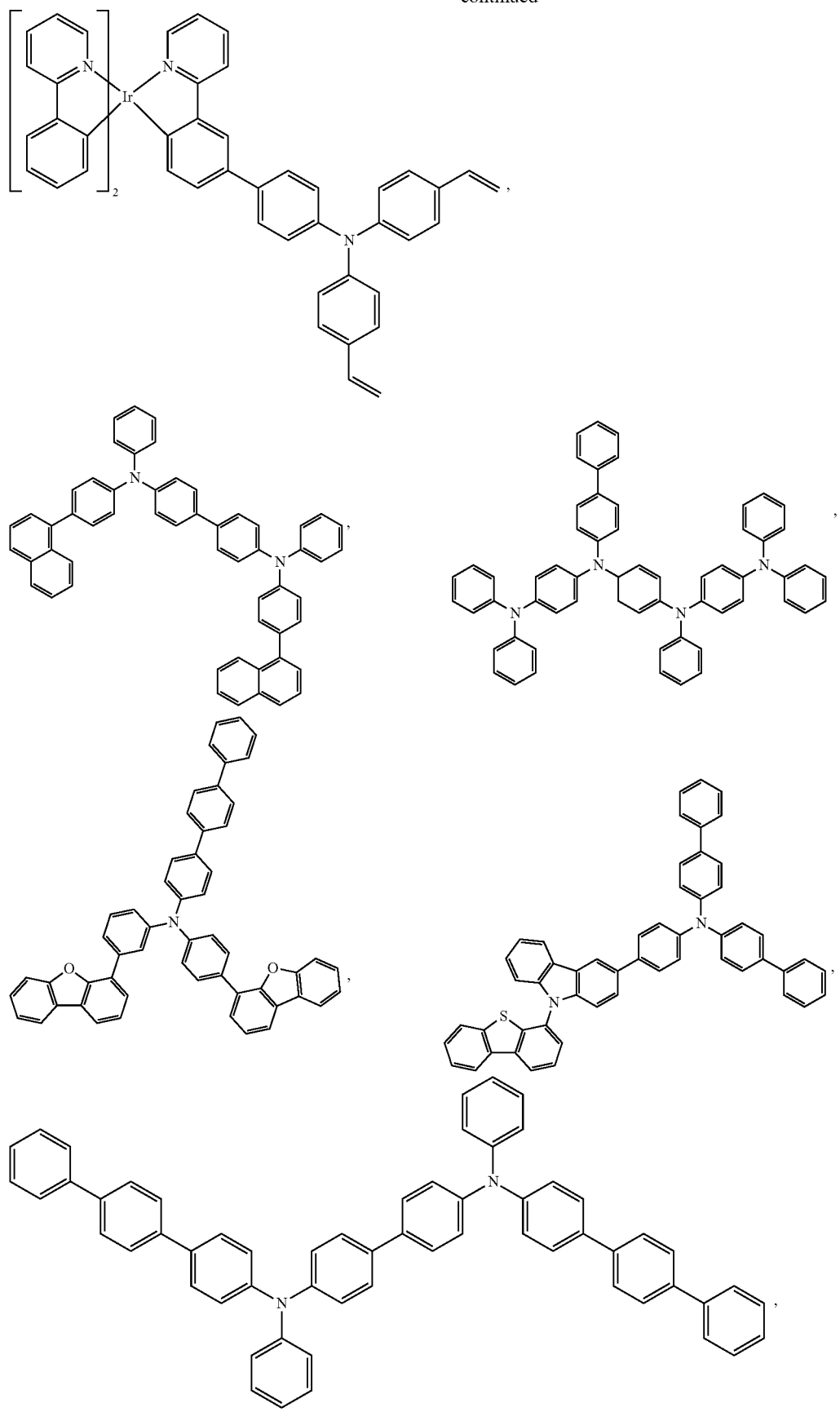

-continued
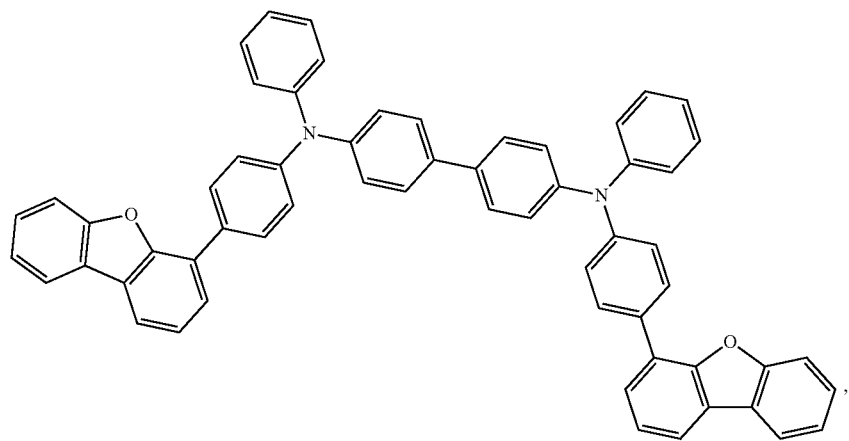
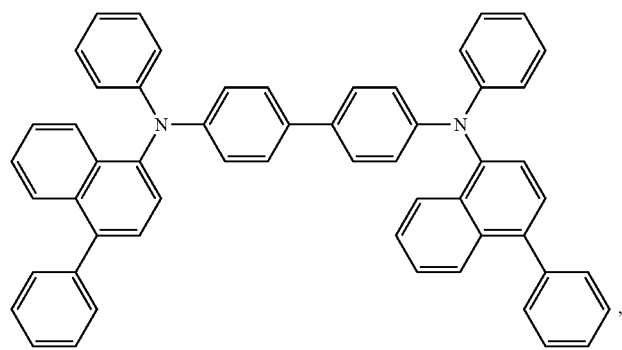
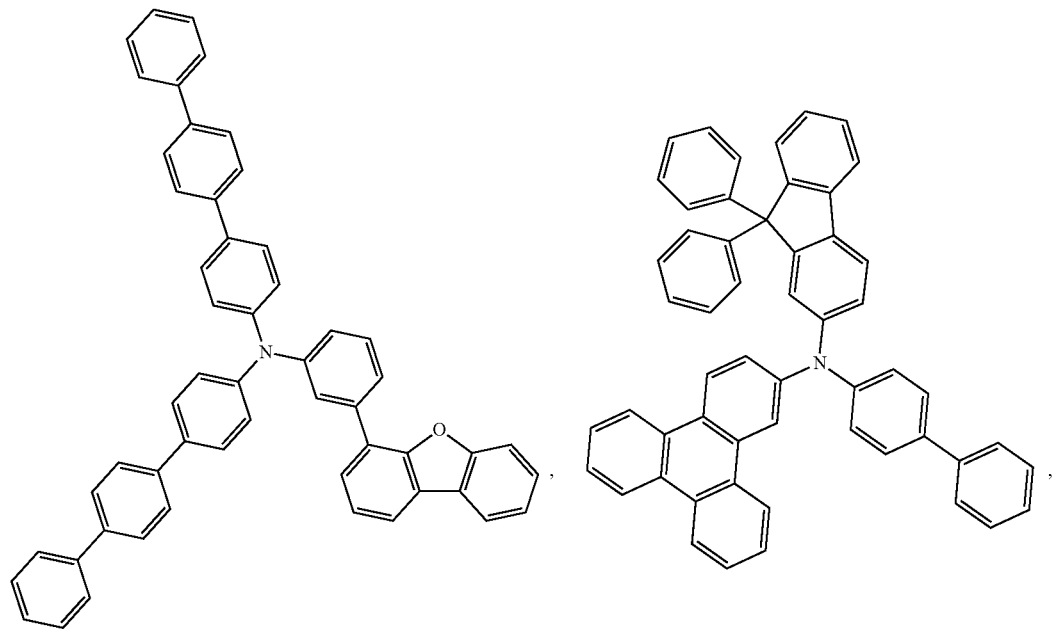

-continued
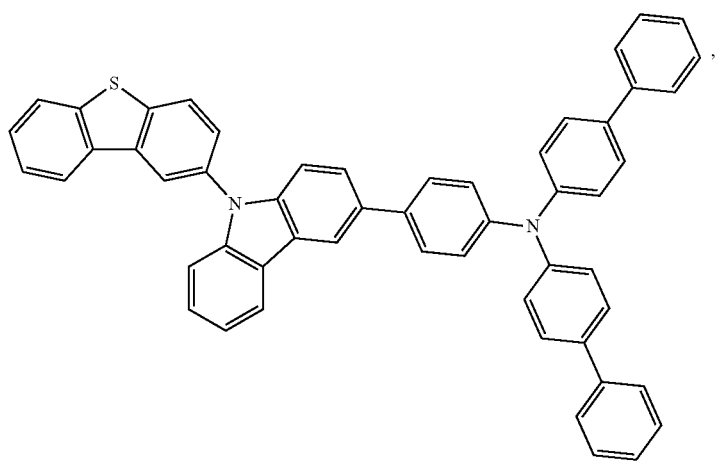
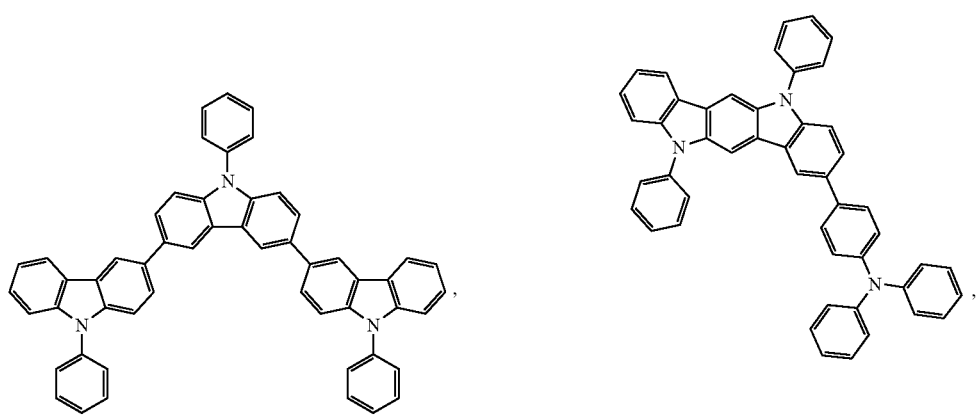
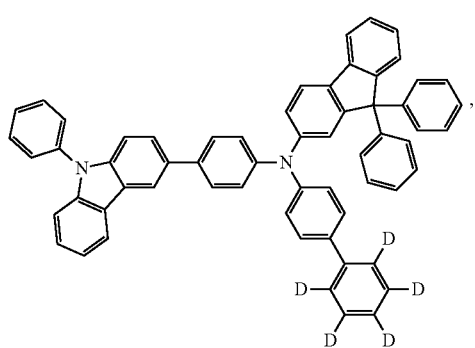
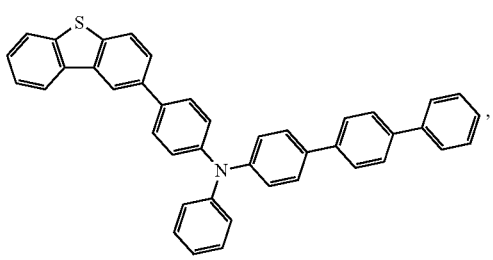
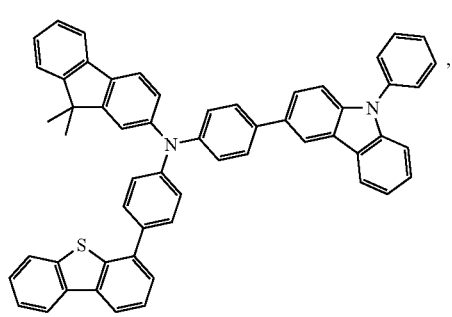
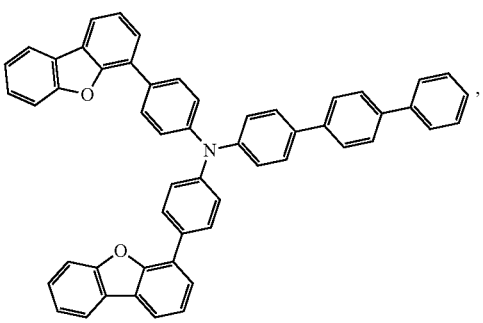

-continued
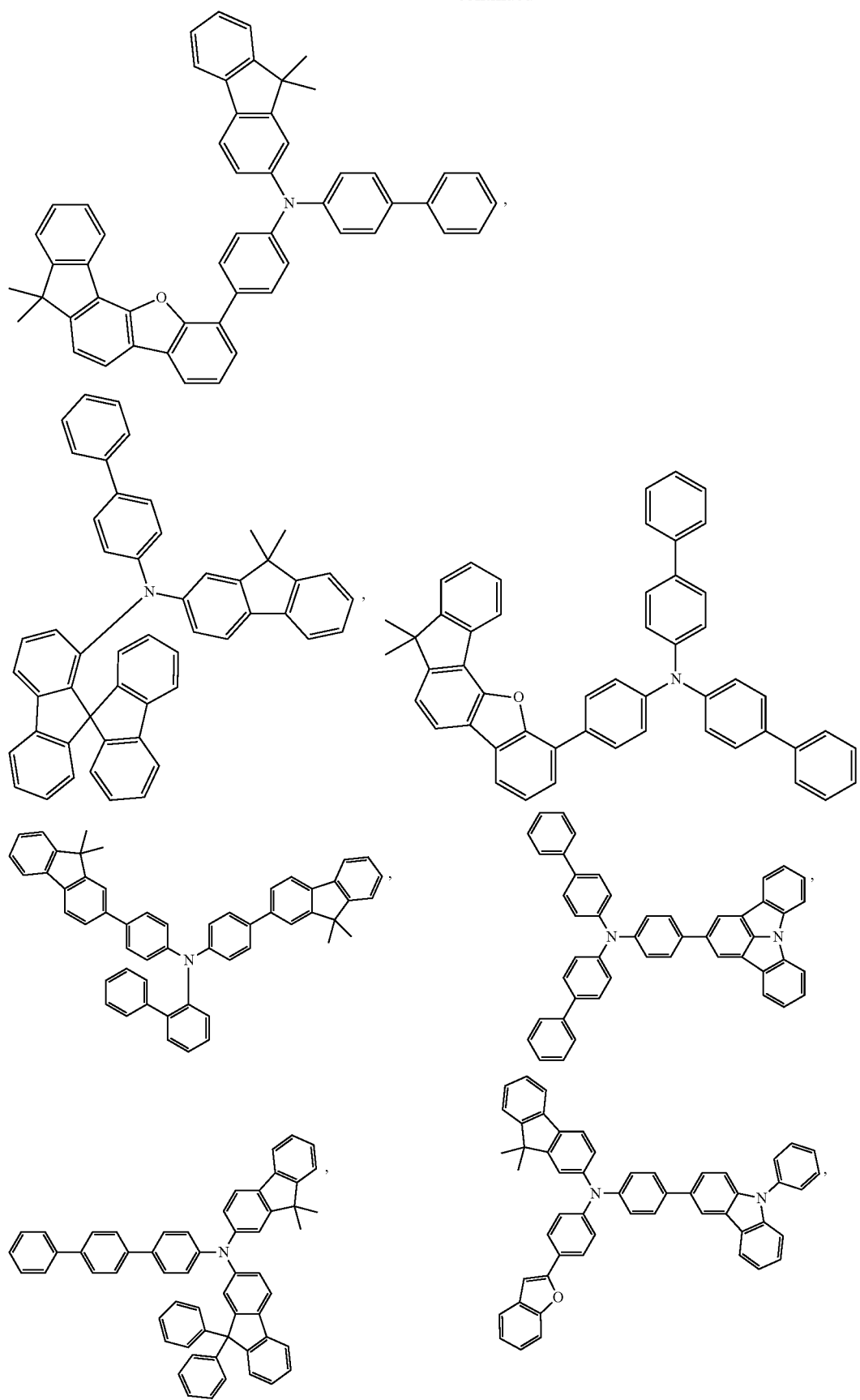

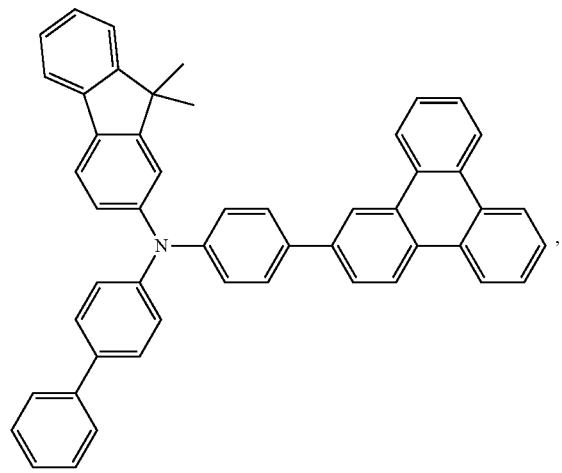
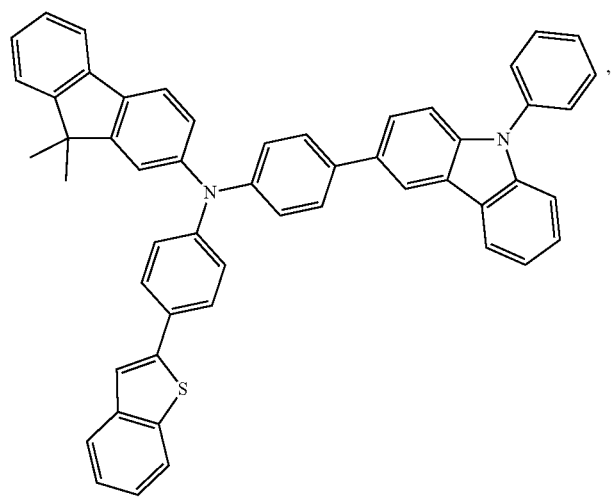
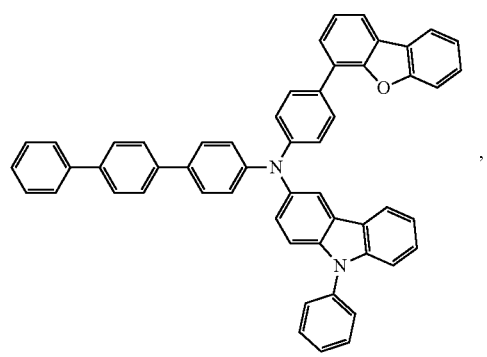
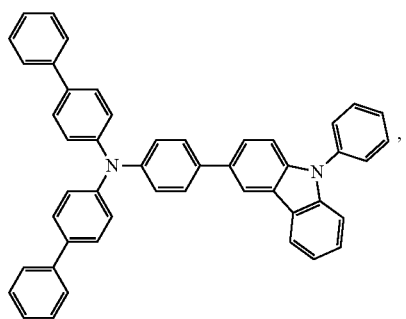

-continued
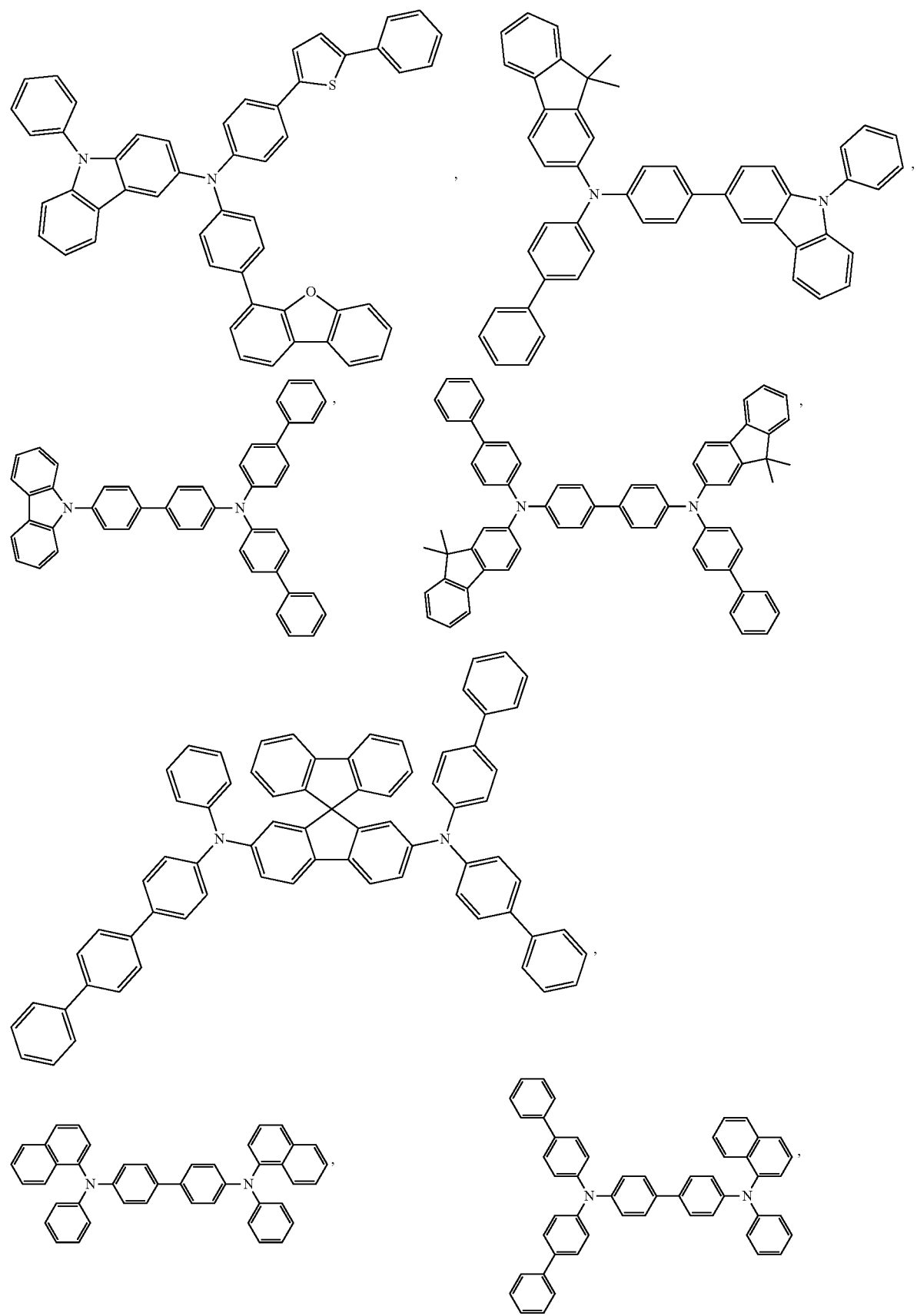

-continued
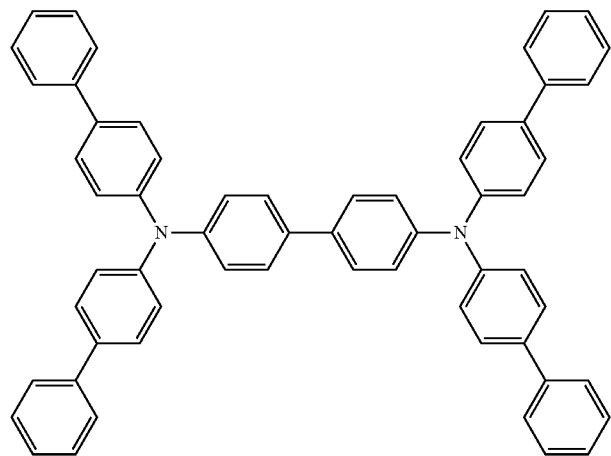
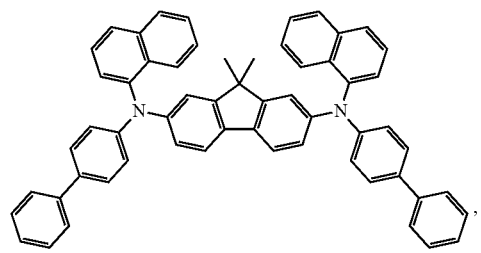
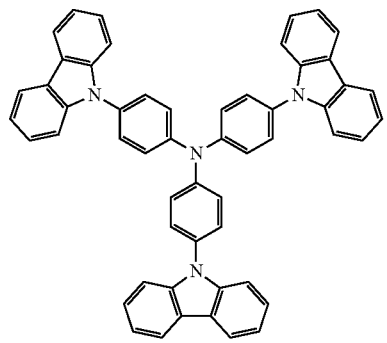
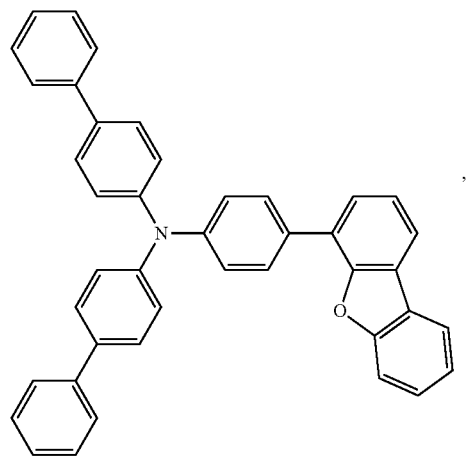
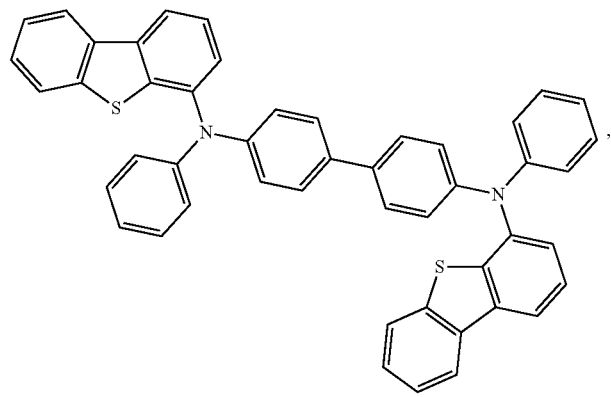

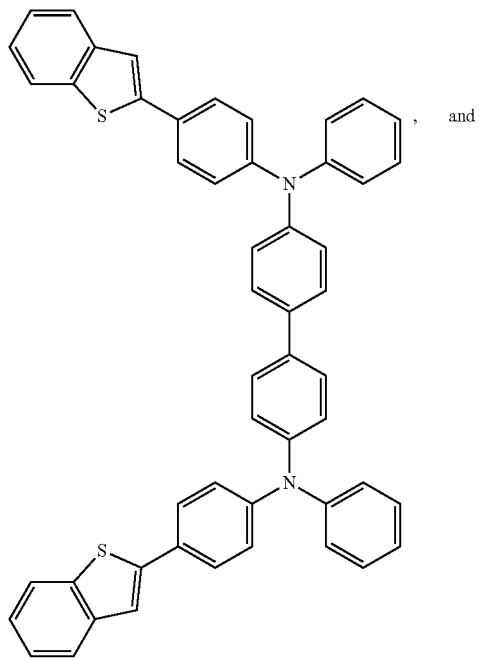

, and

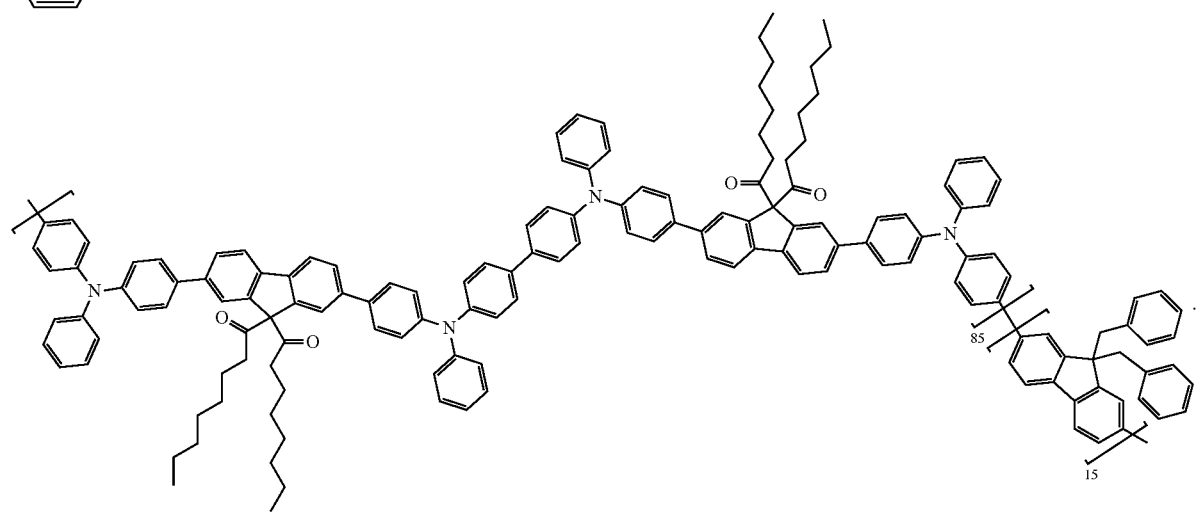

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

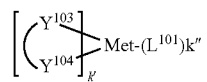

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

91

In one aspect, the metal complexes are:

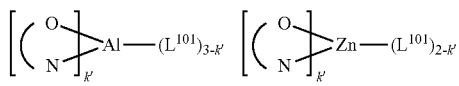

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

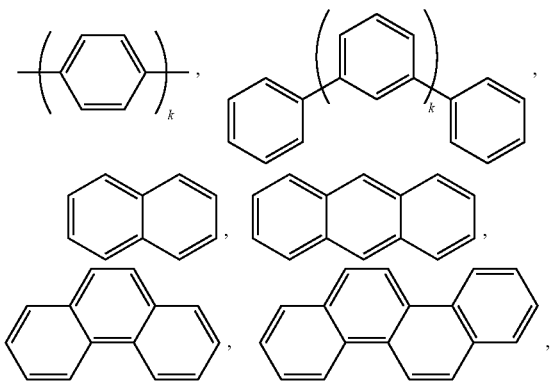

92

-continued

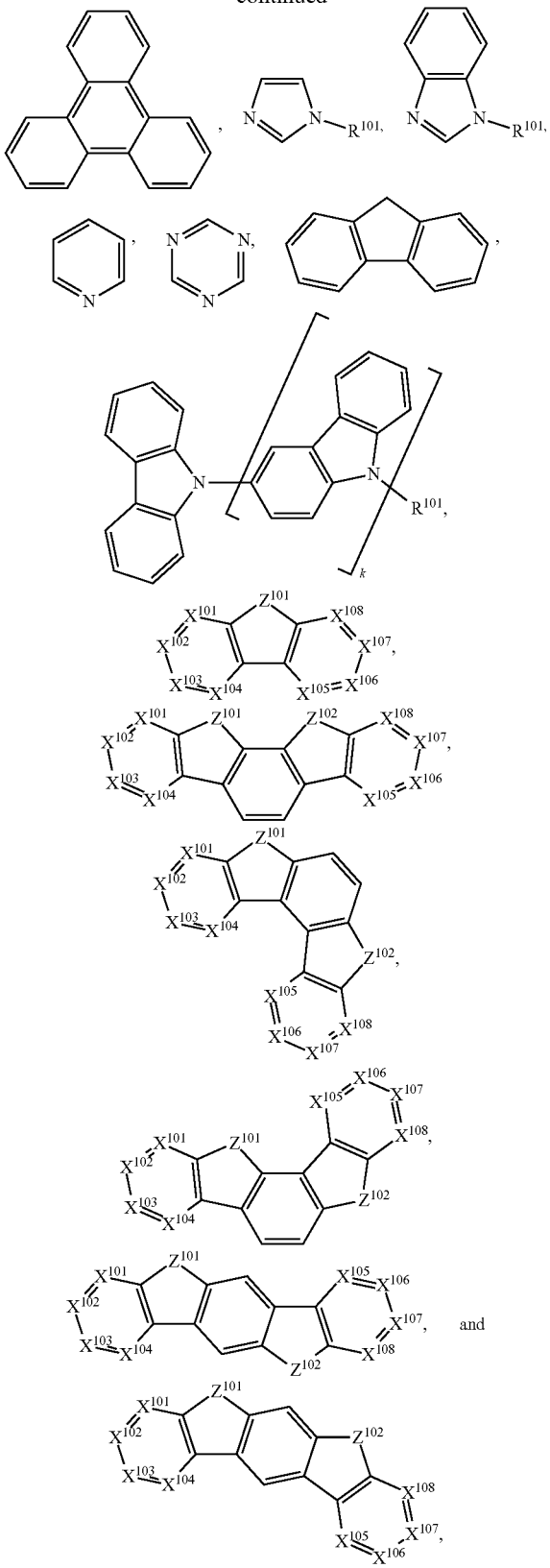

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

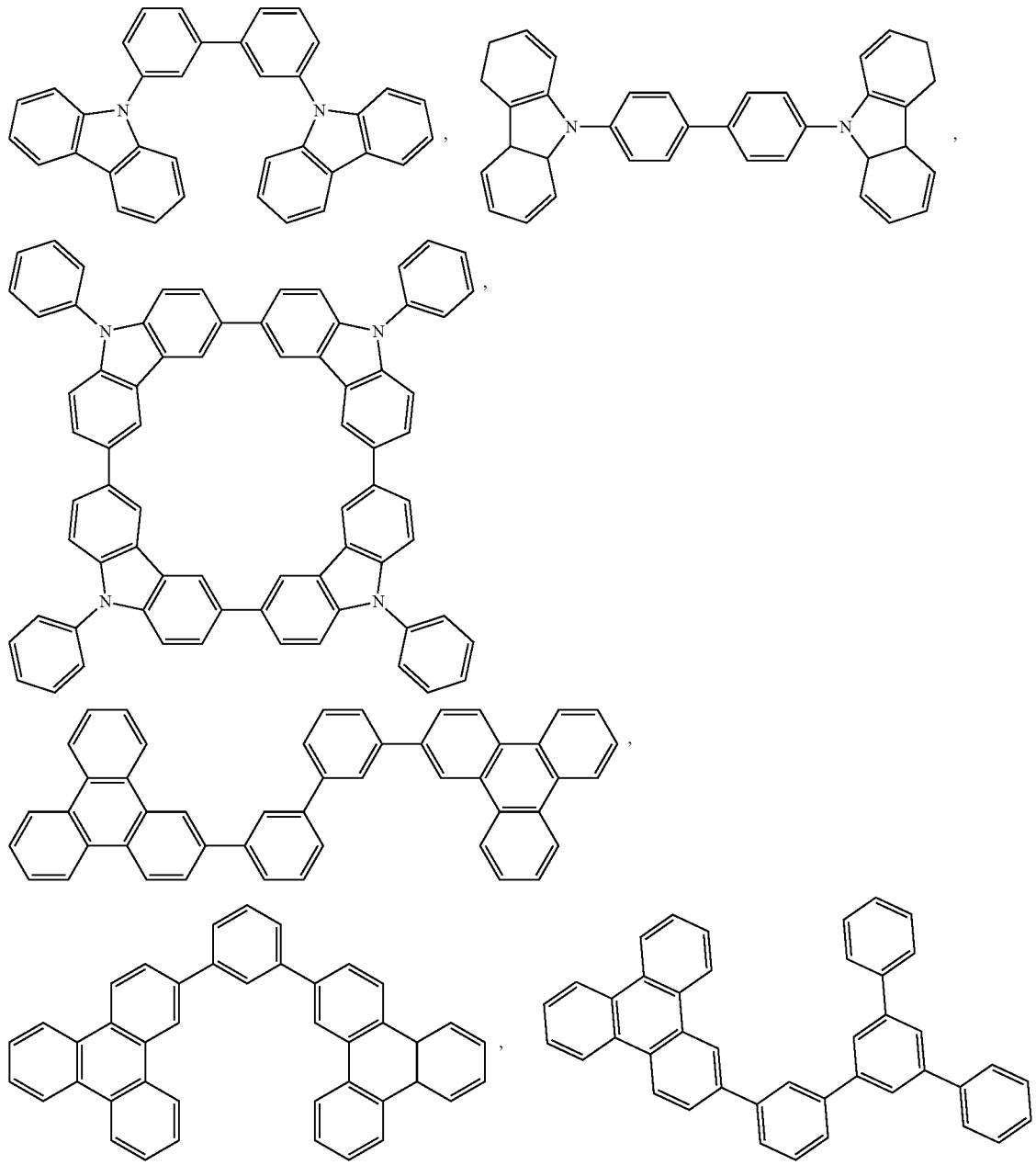

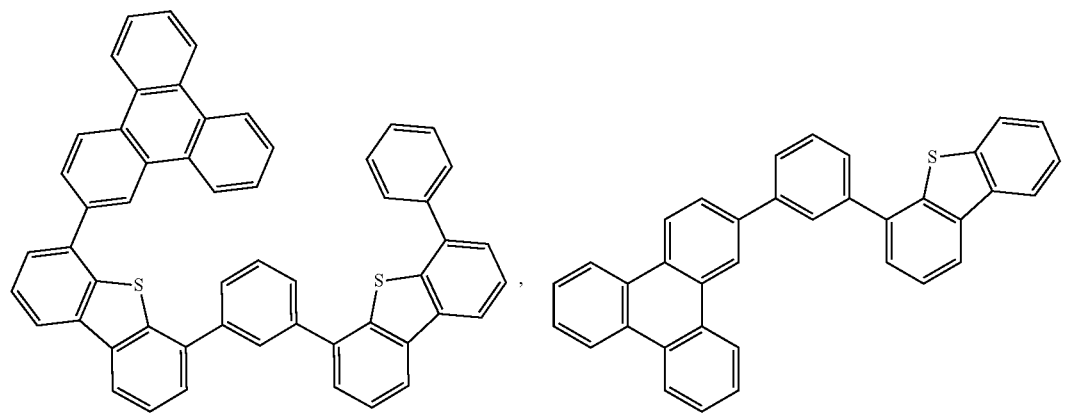
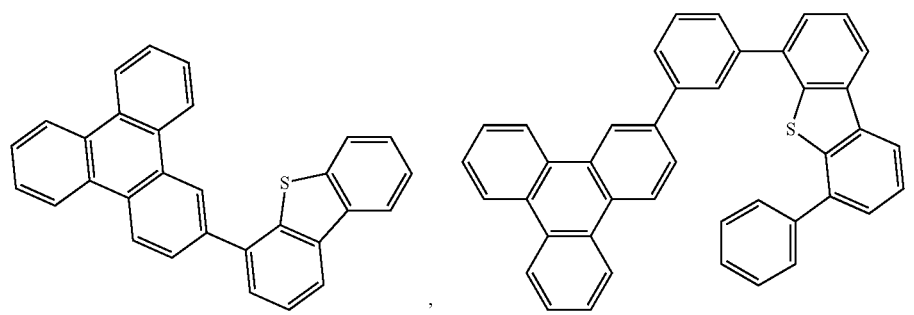
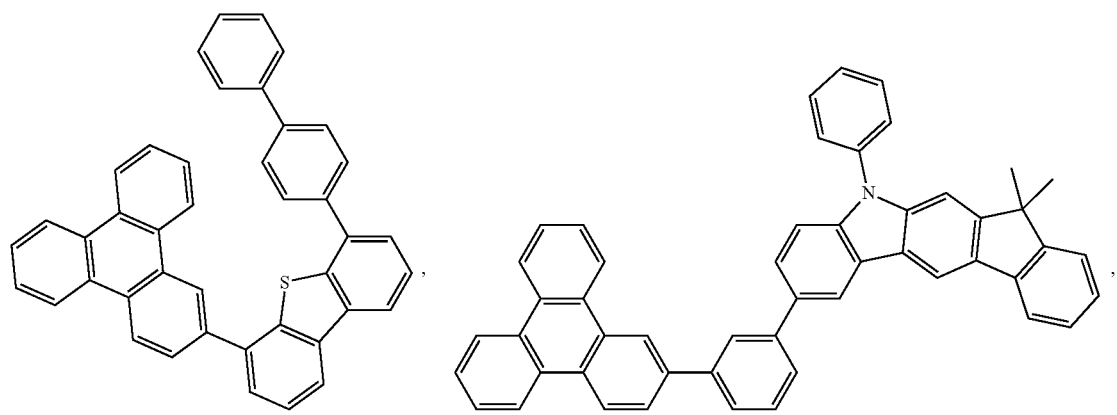
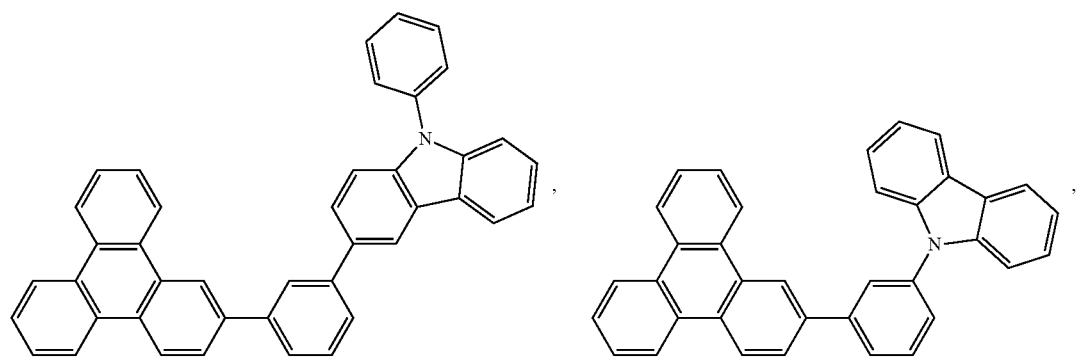

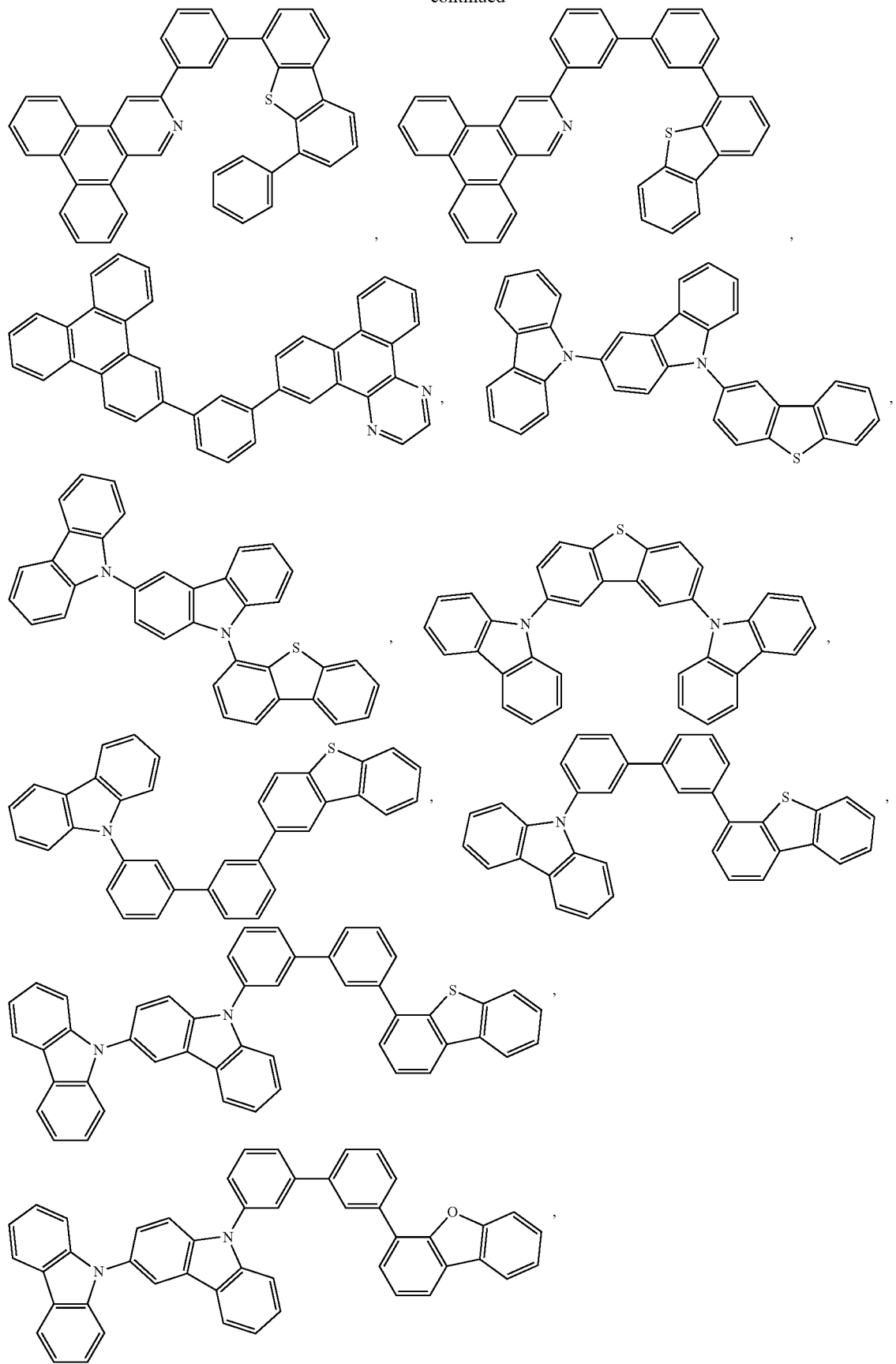

-continued
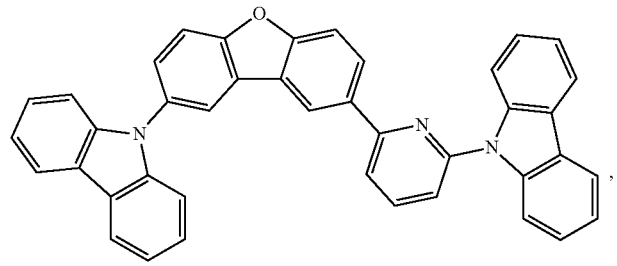
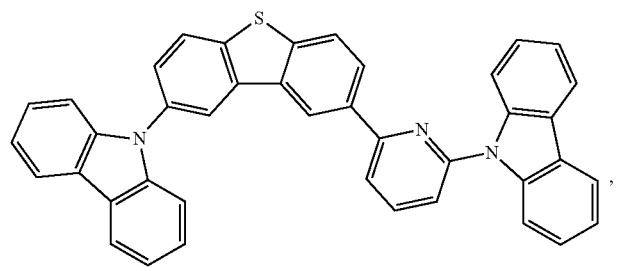
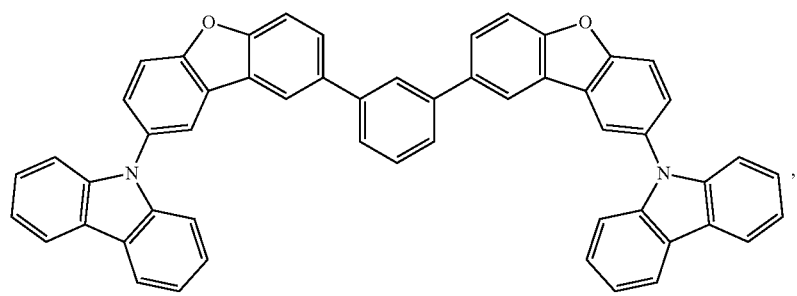
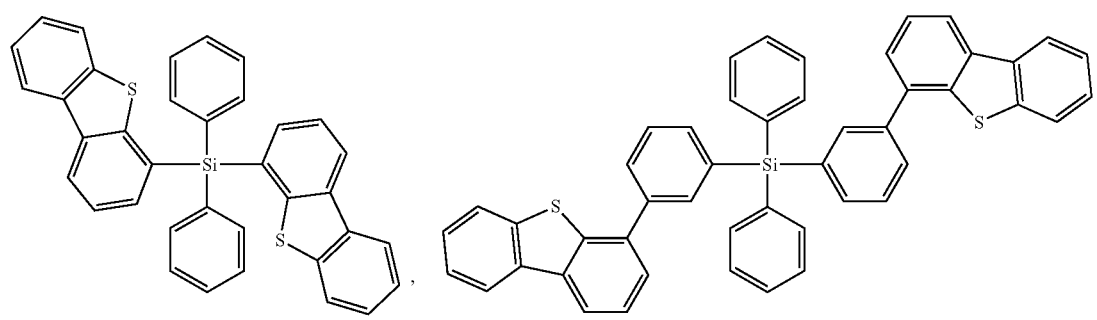
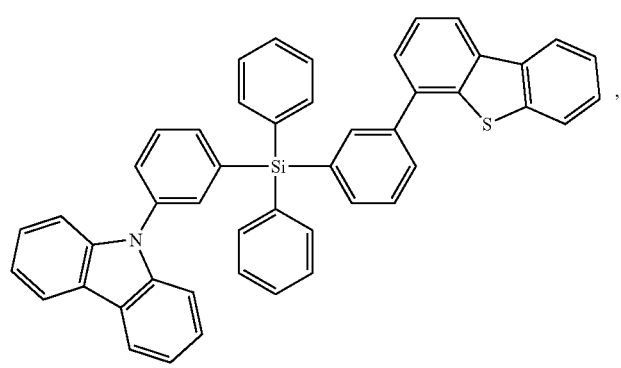

-continued
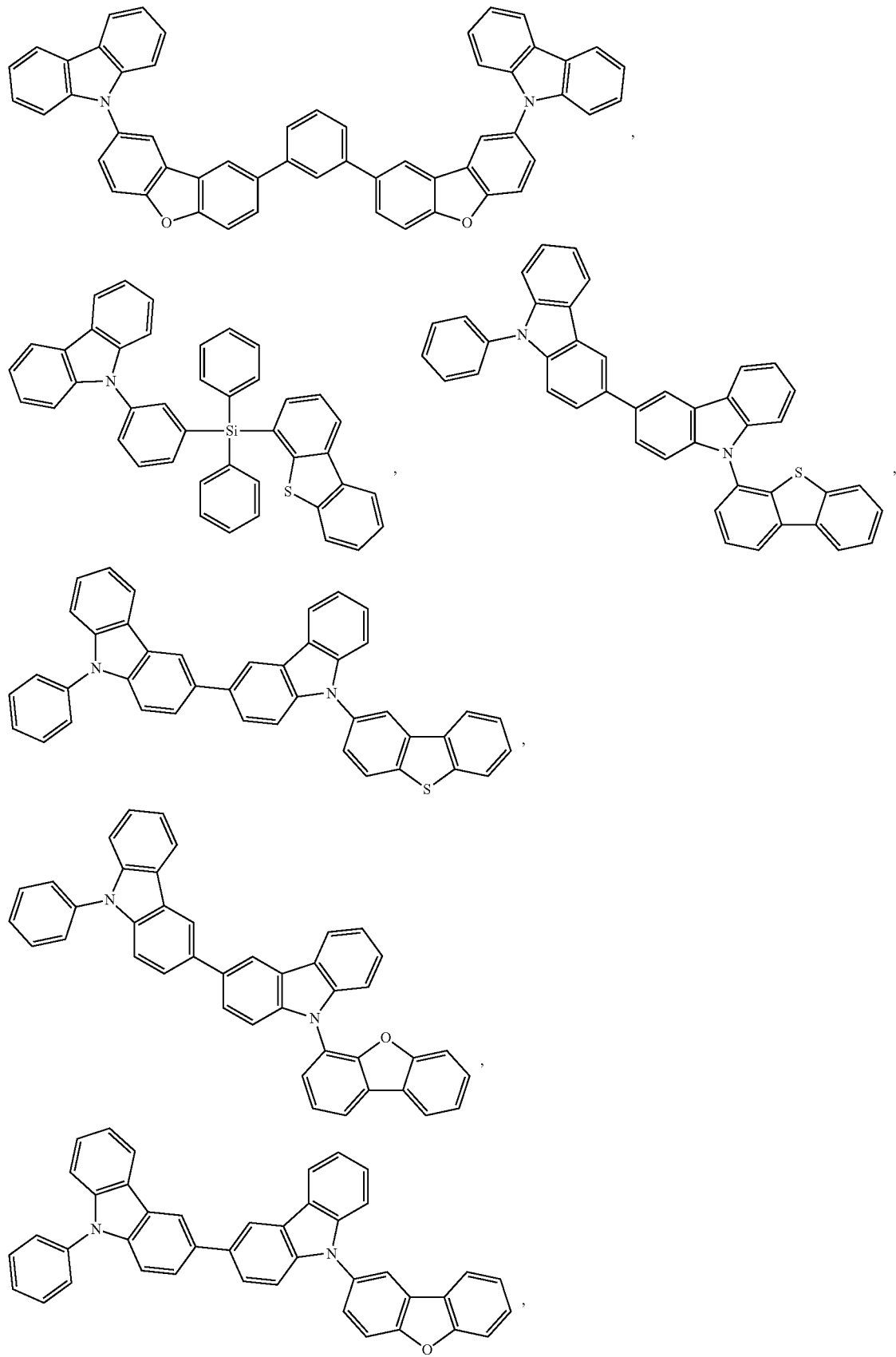

-continued
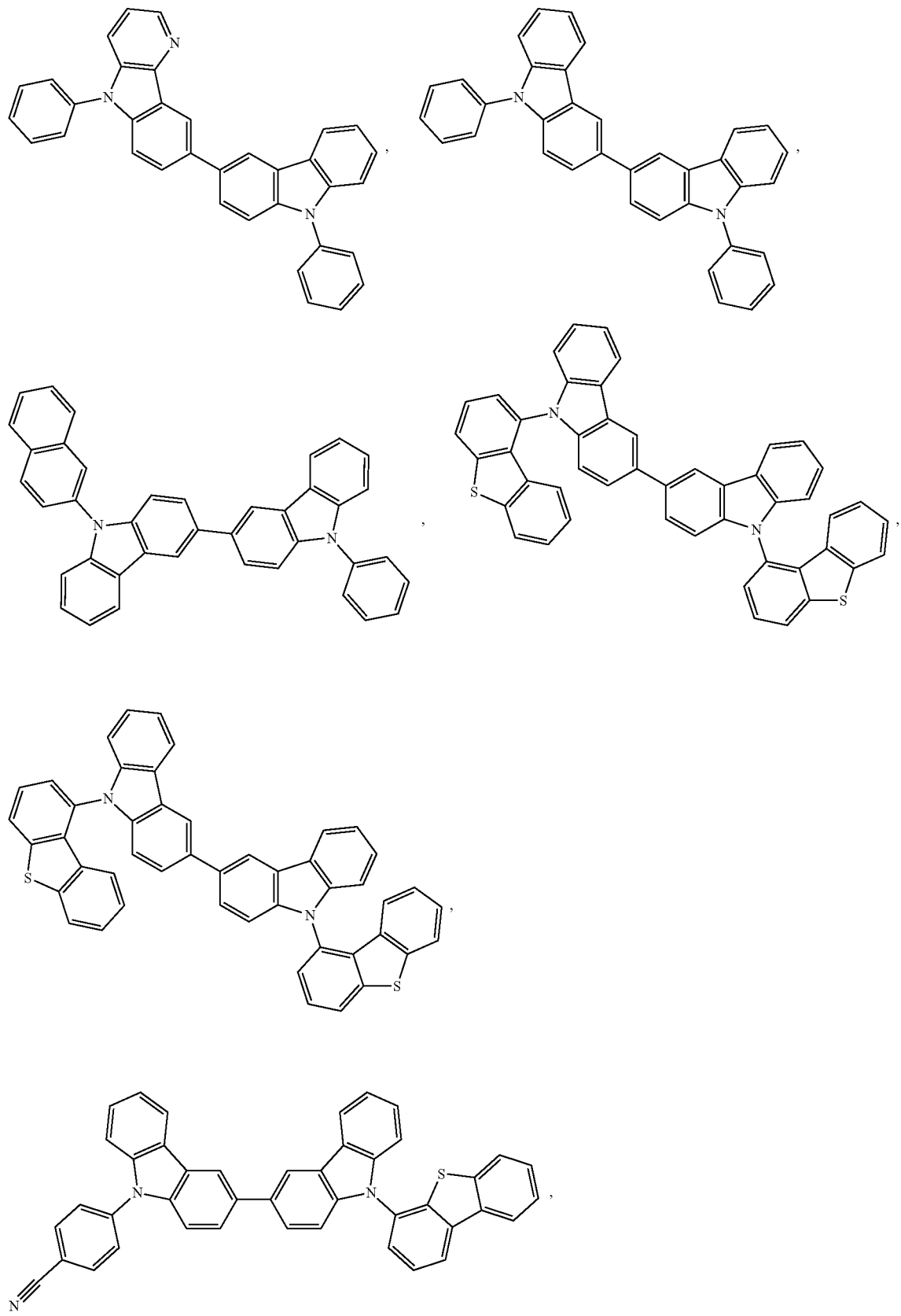

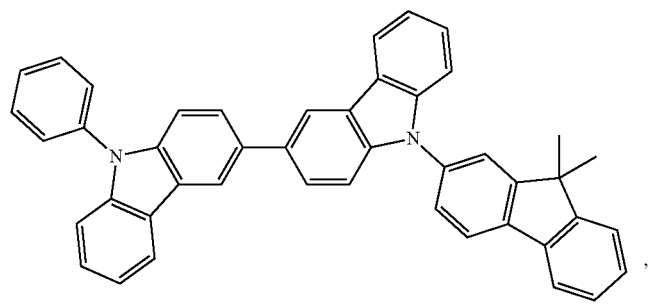
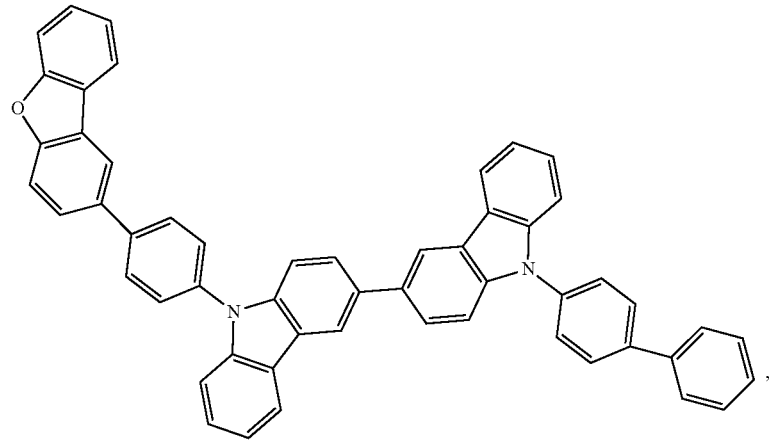
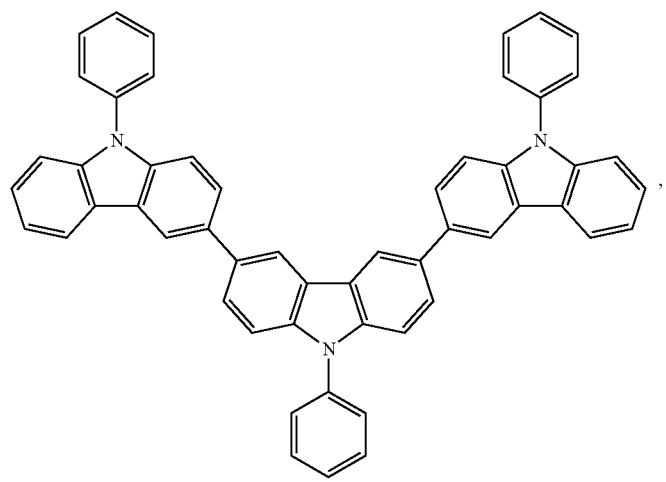
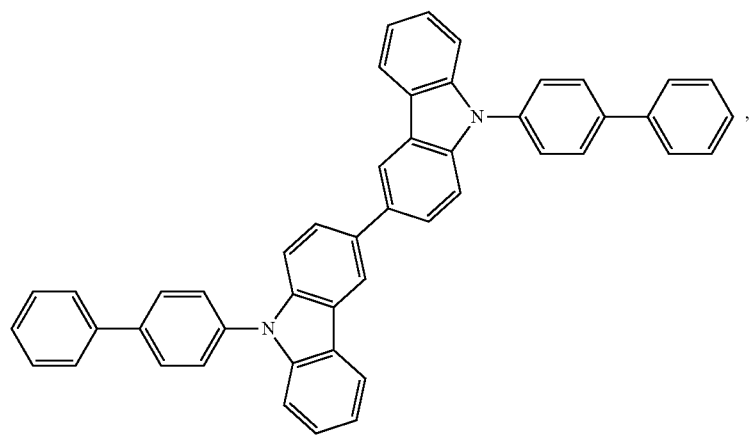

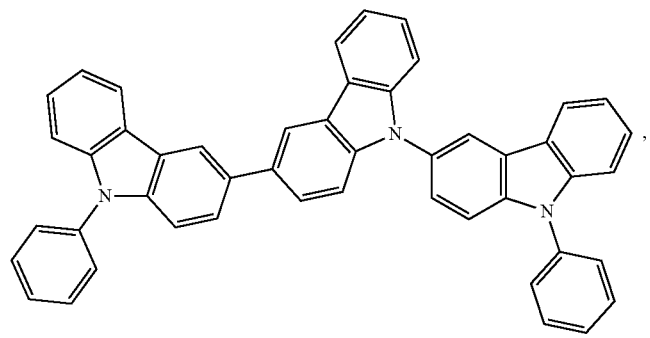
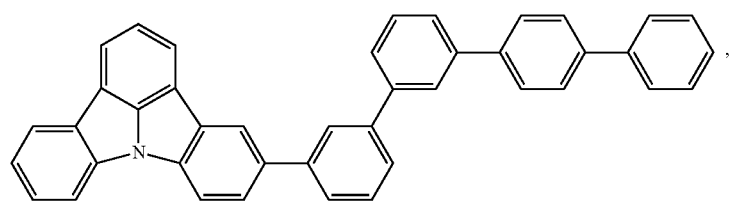
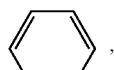
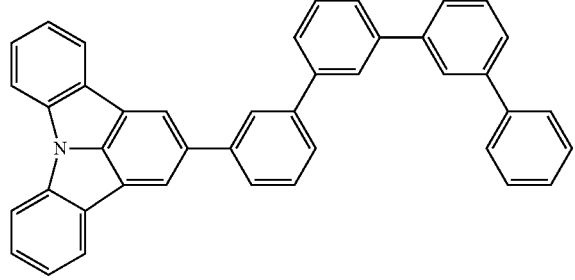
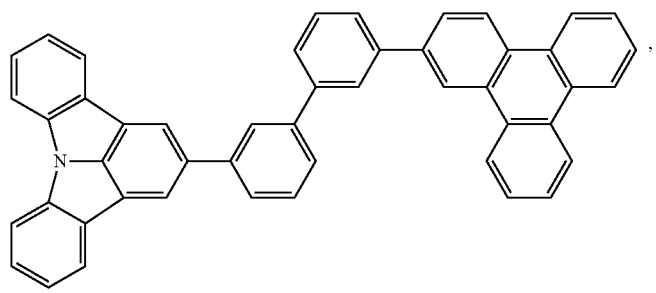
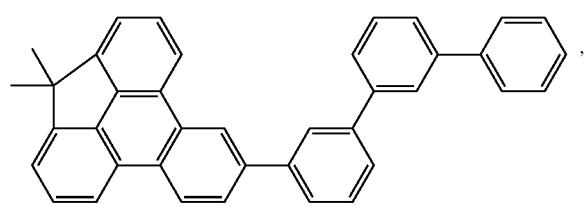

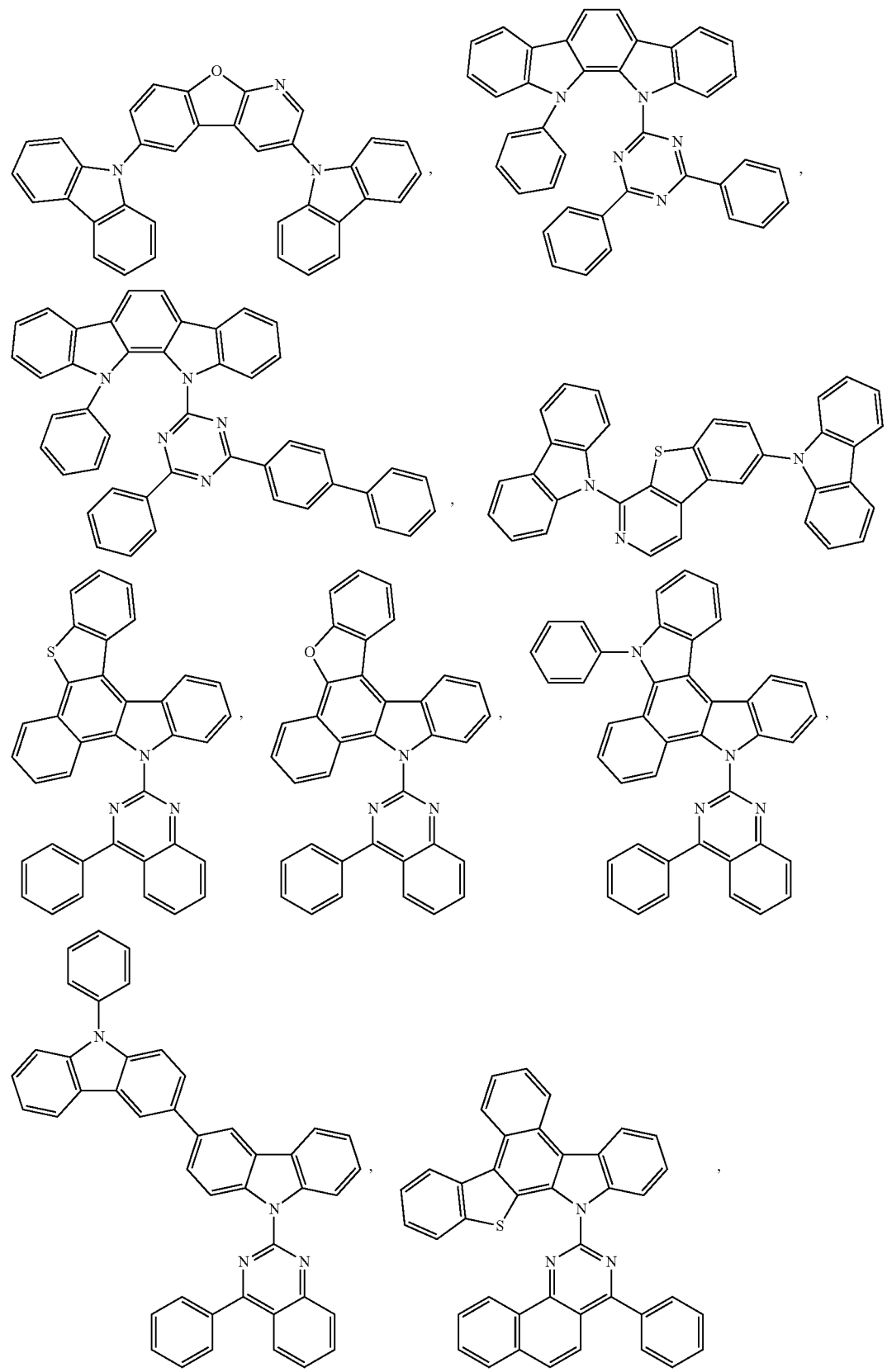

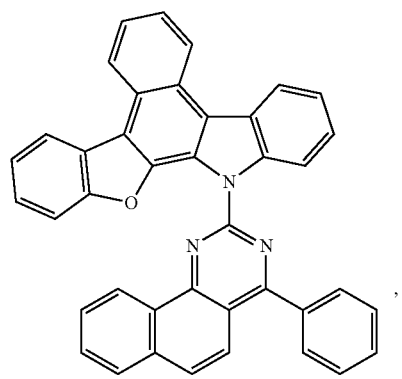
,
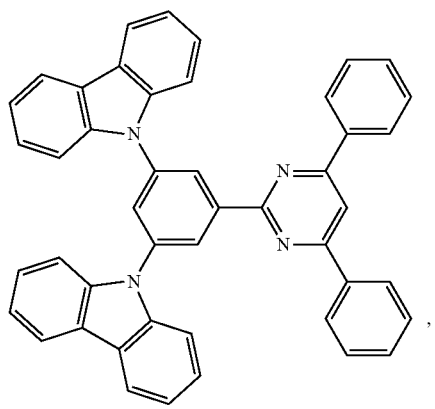
,
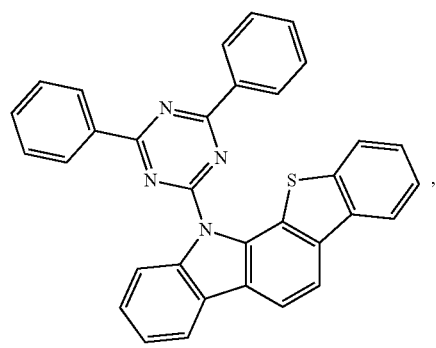
,
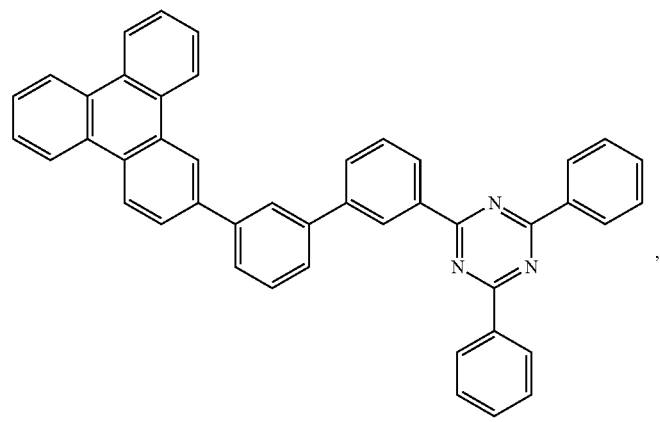
,
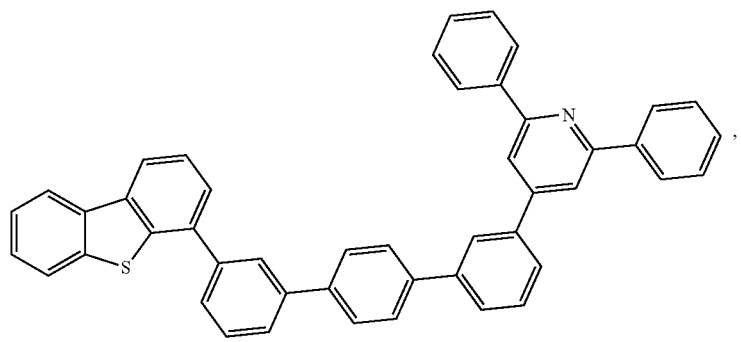
,
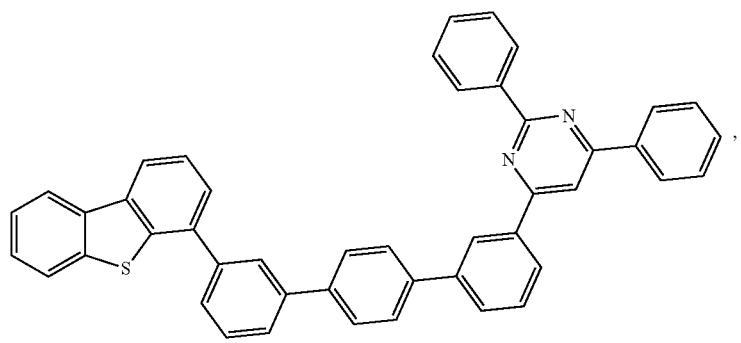
,

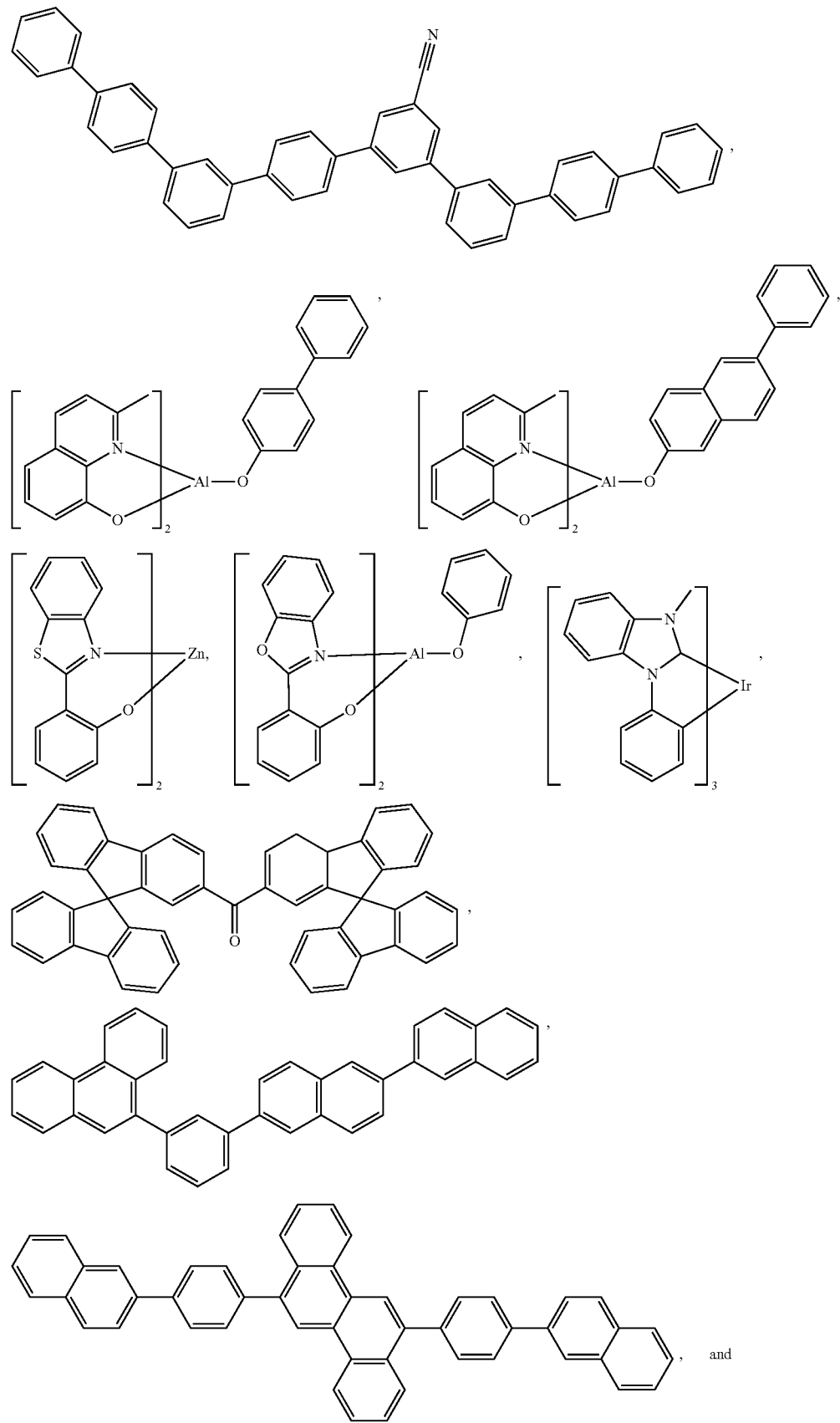

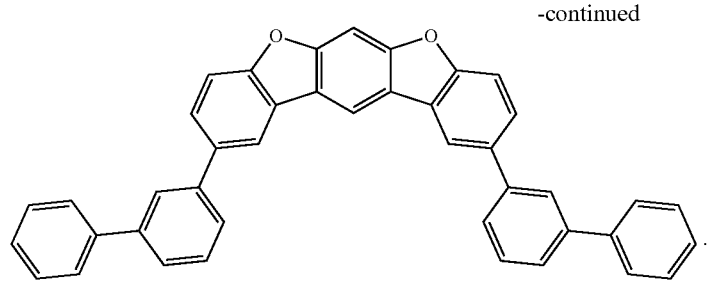

e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

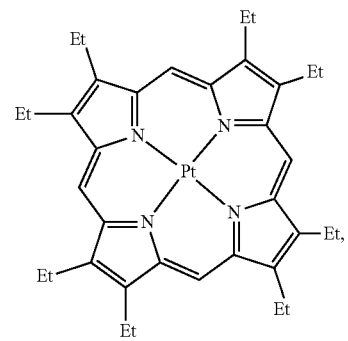

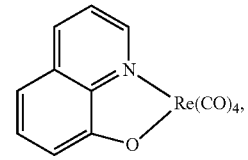

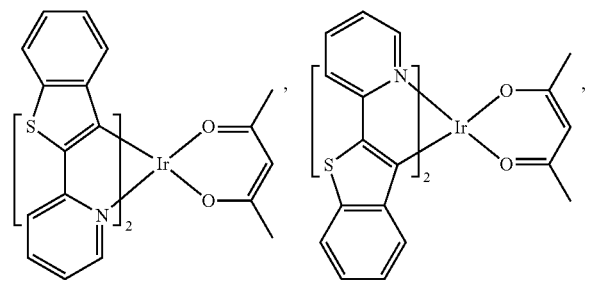

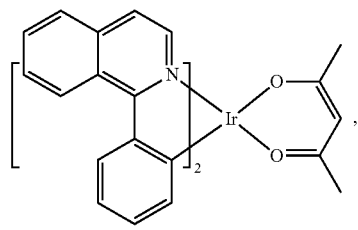

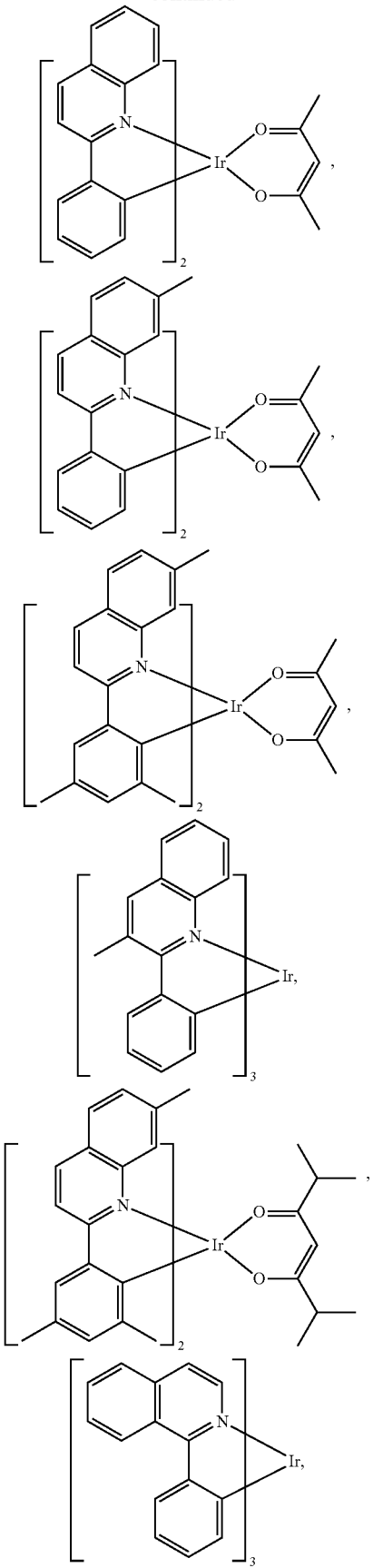
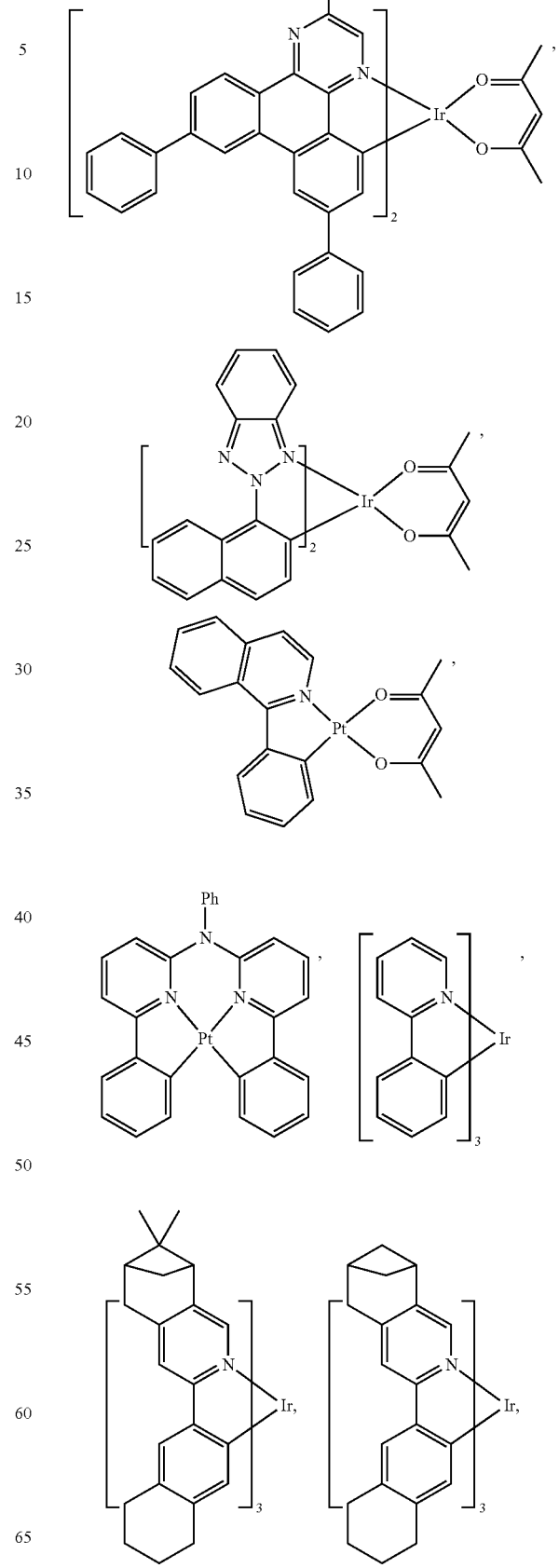

119
-continued
120
-continued
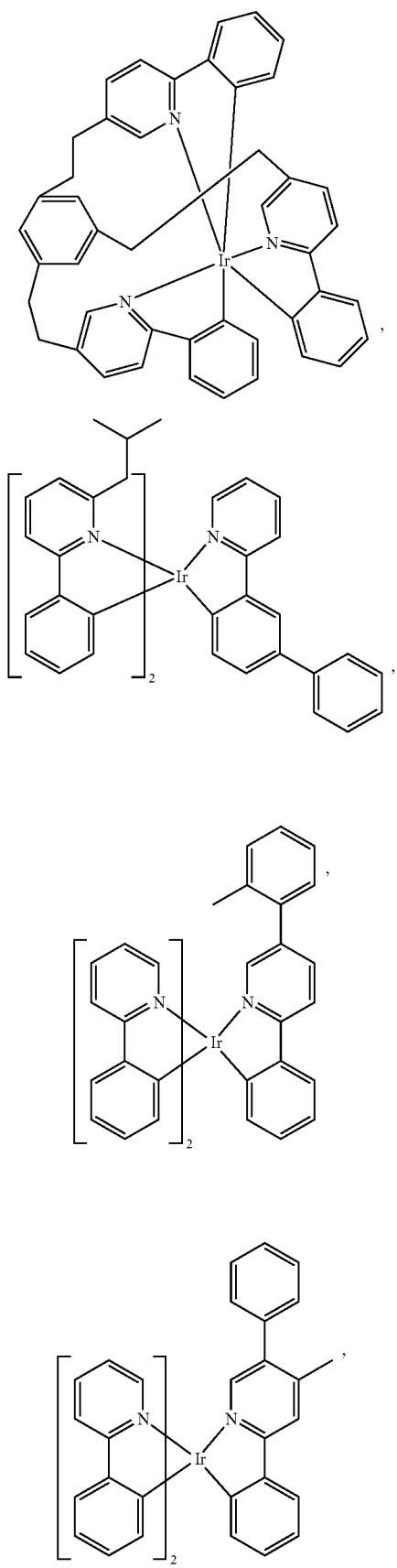
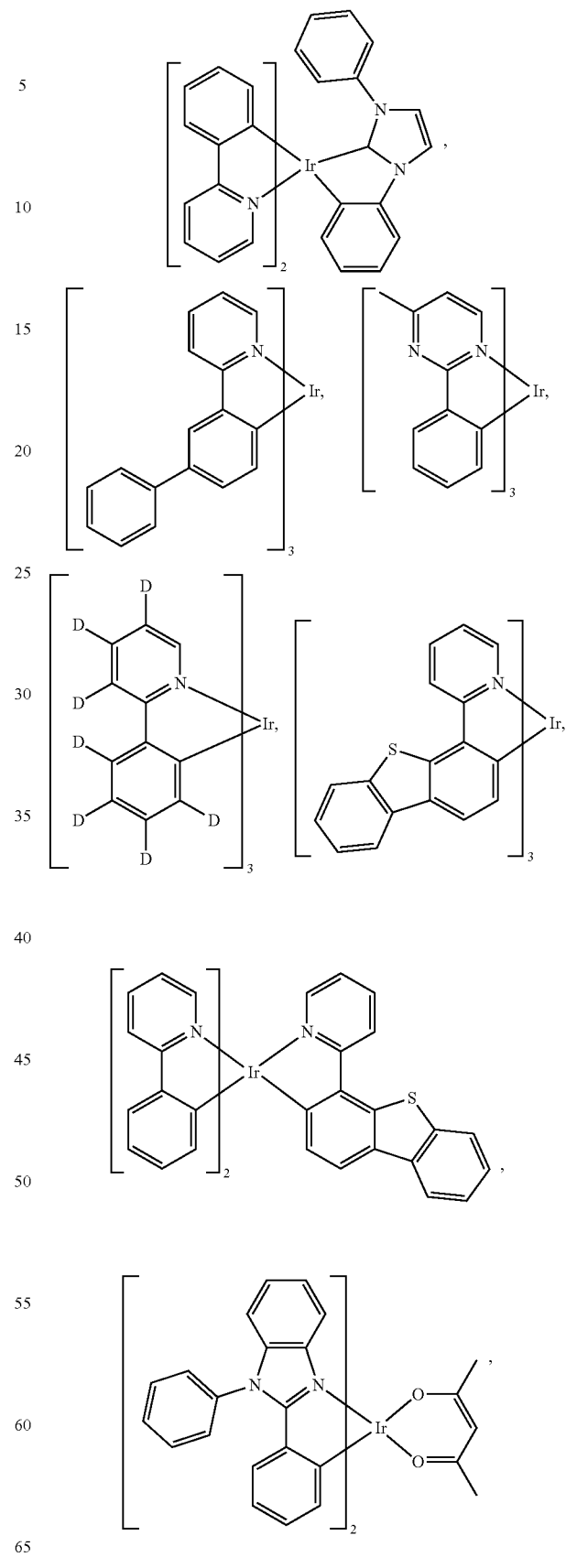

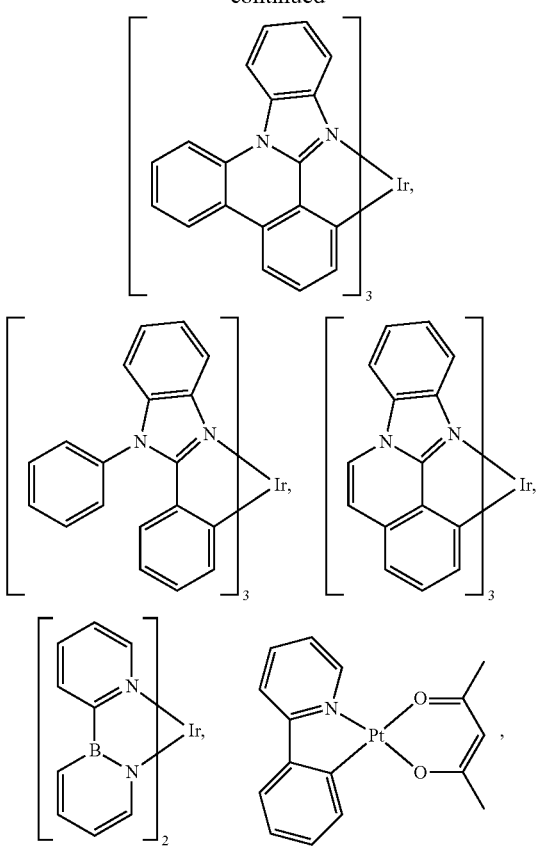
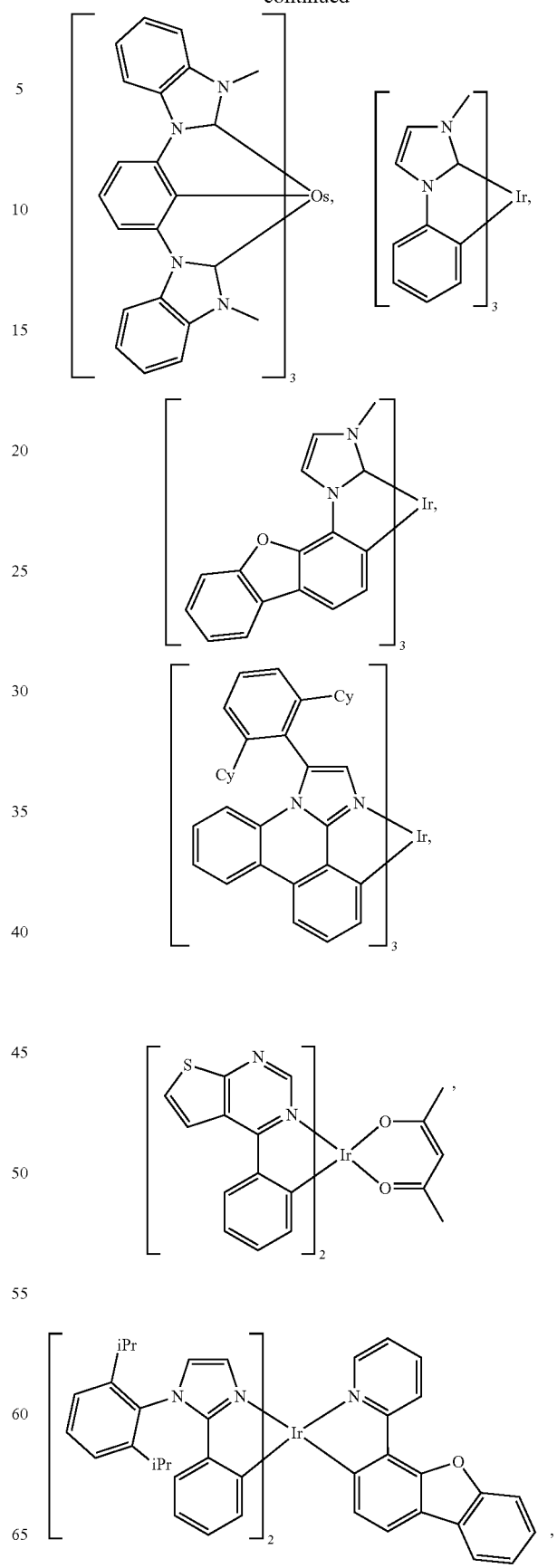

123
-continued
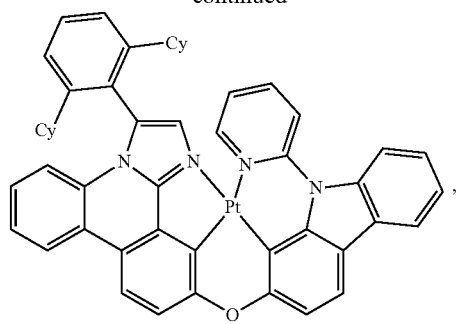
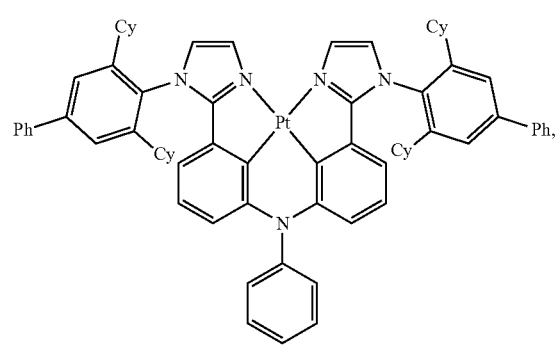
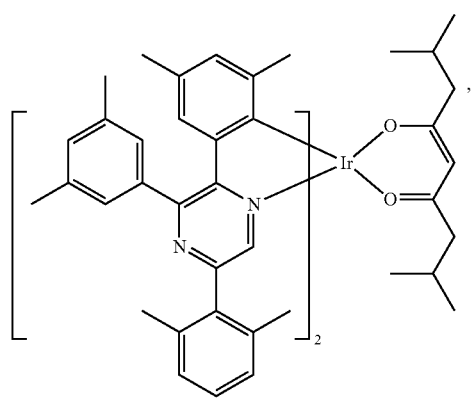
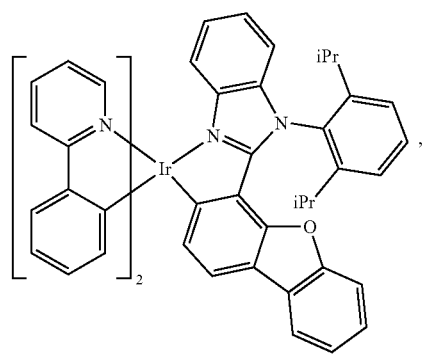
124
-continued
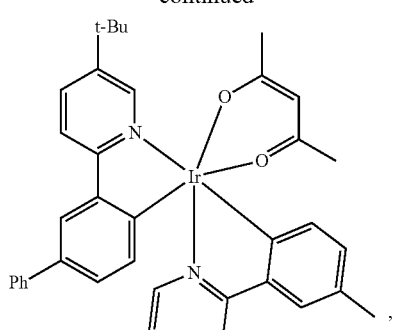
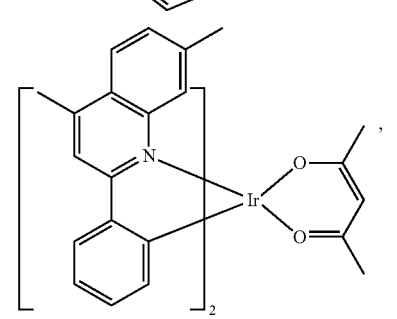
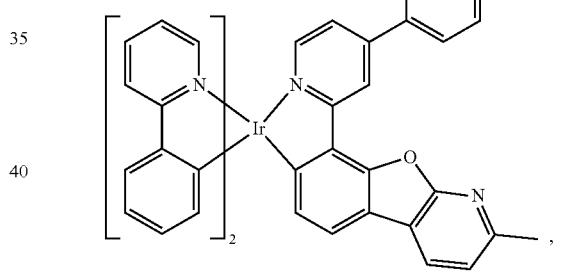
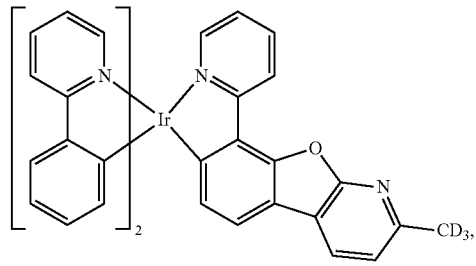
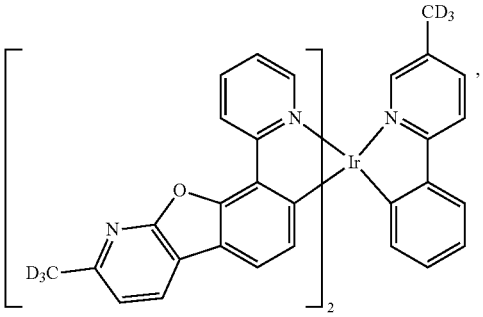

-continued
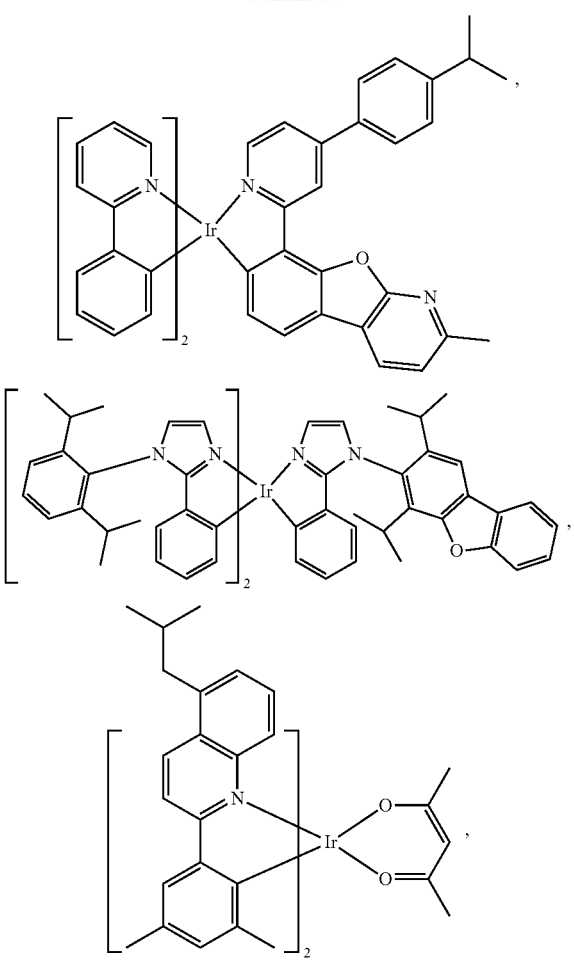
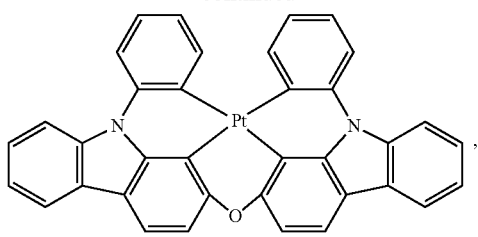
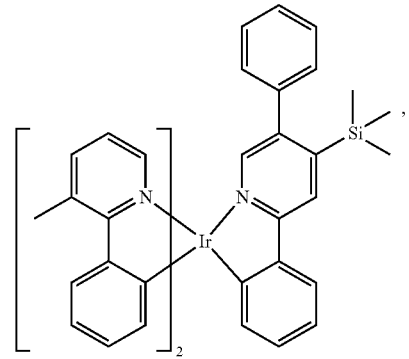
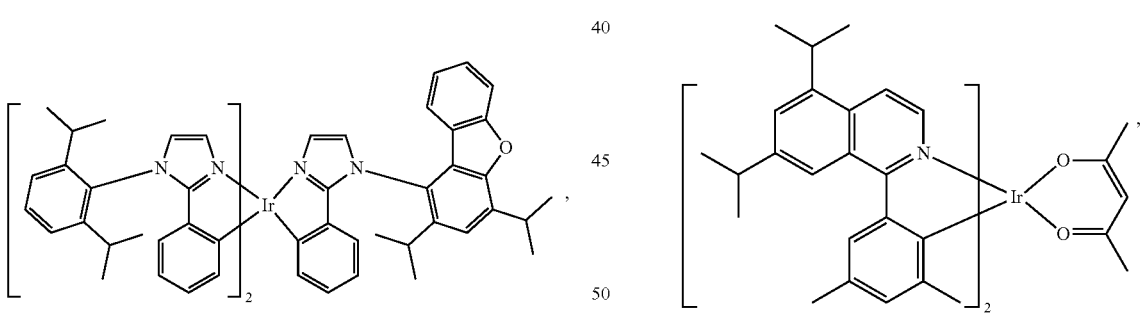
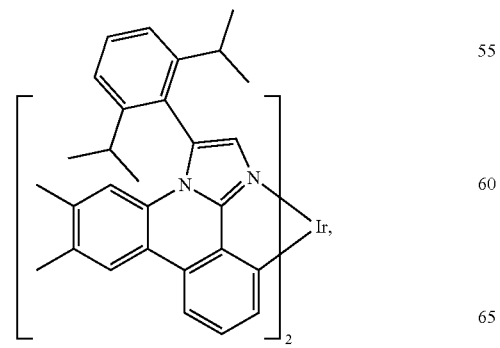
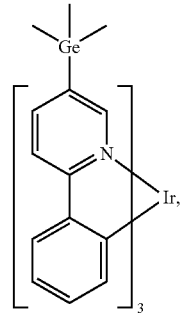

127
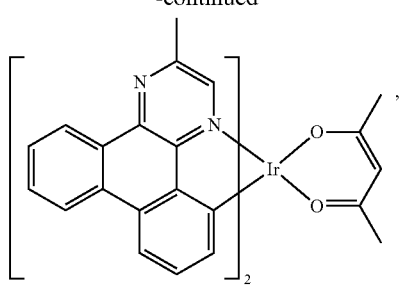
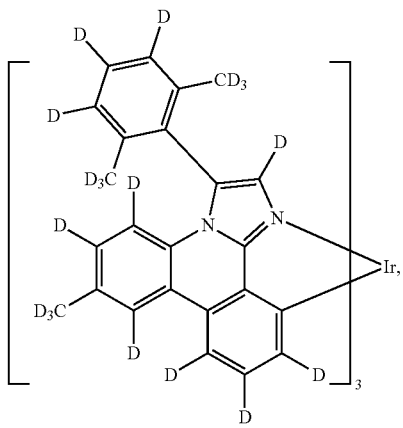
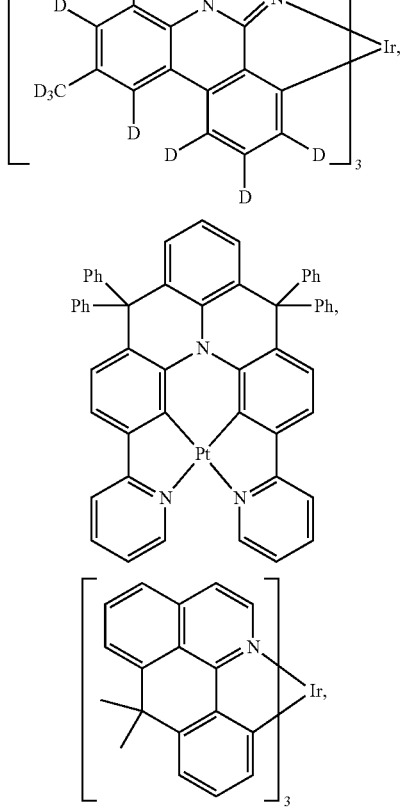
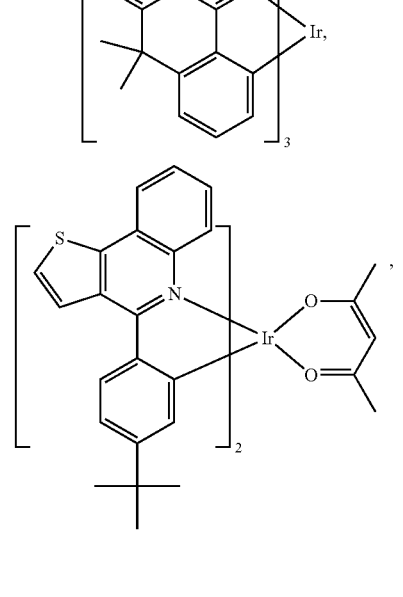
128
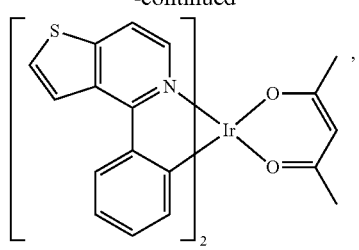
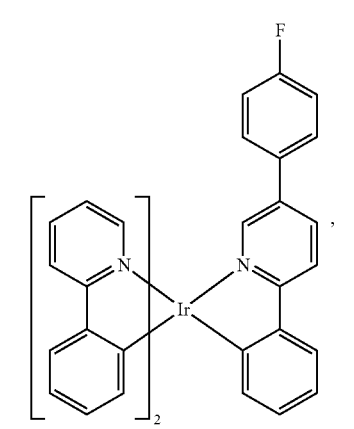
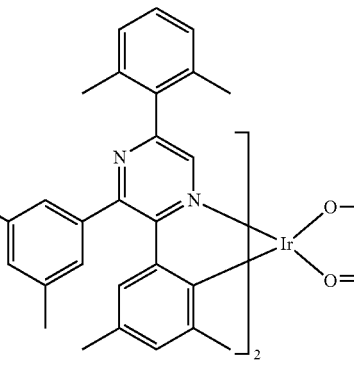
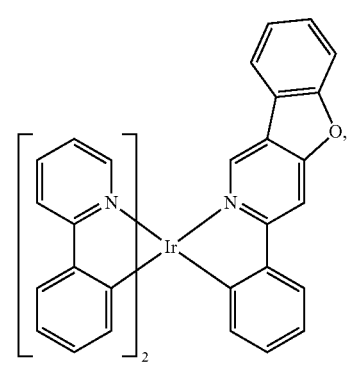

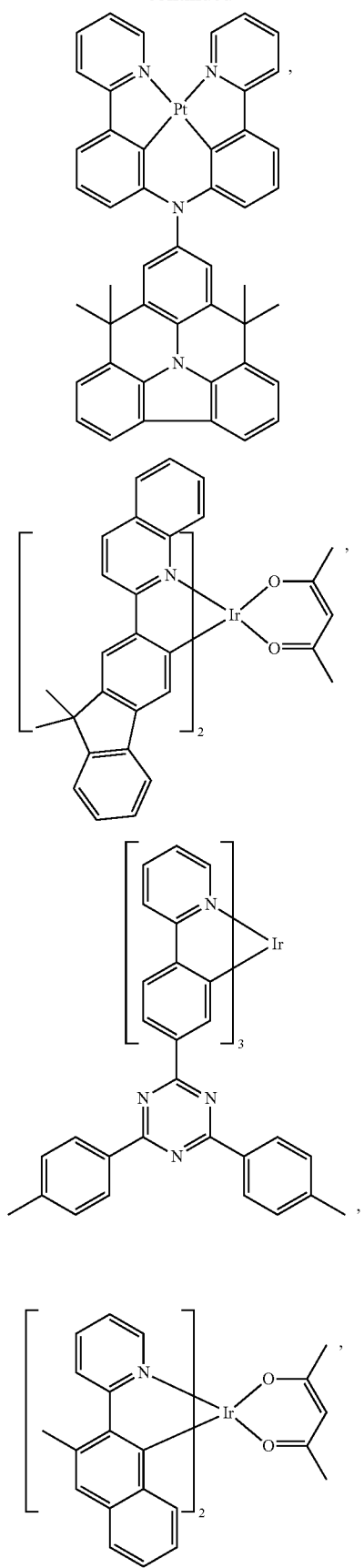
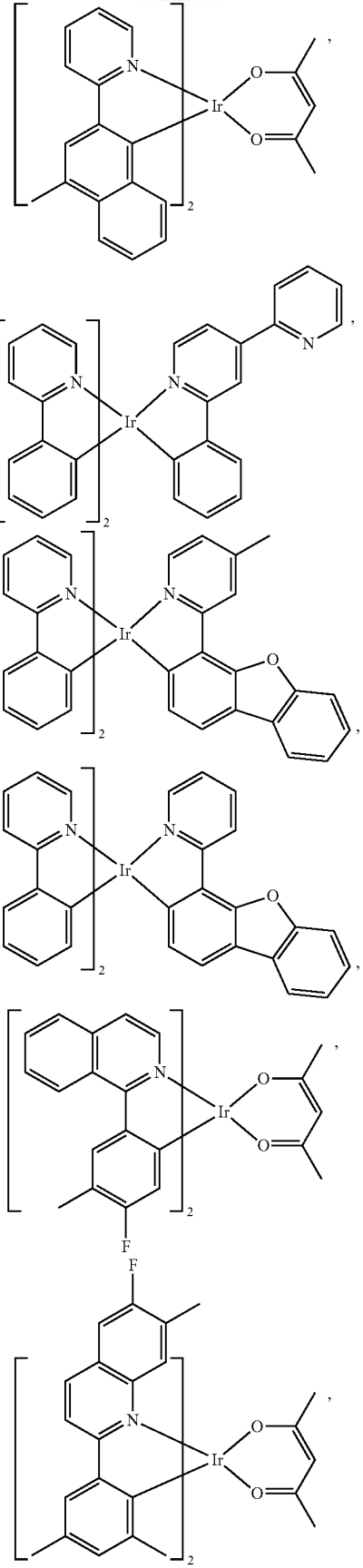

131
-continued
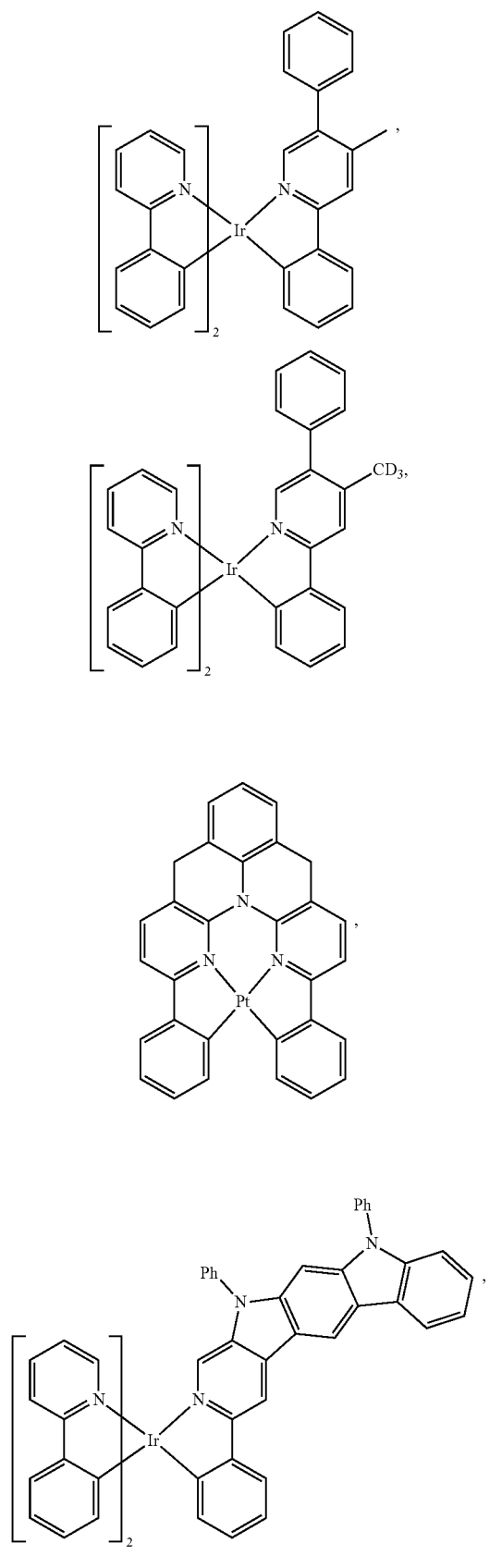
132
-continued
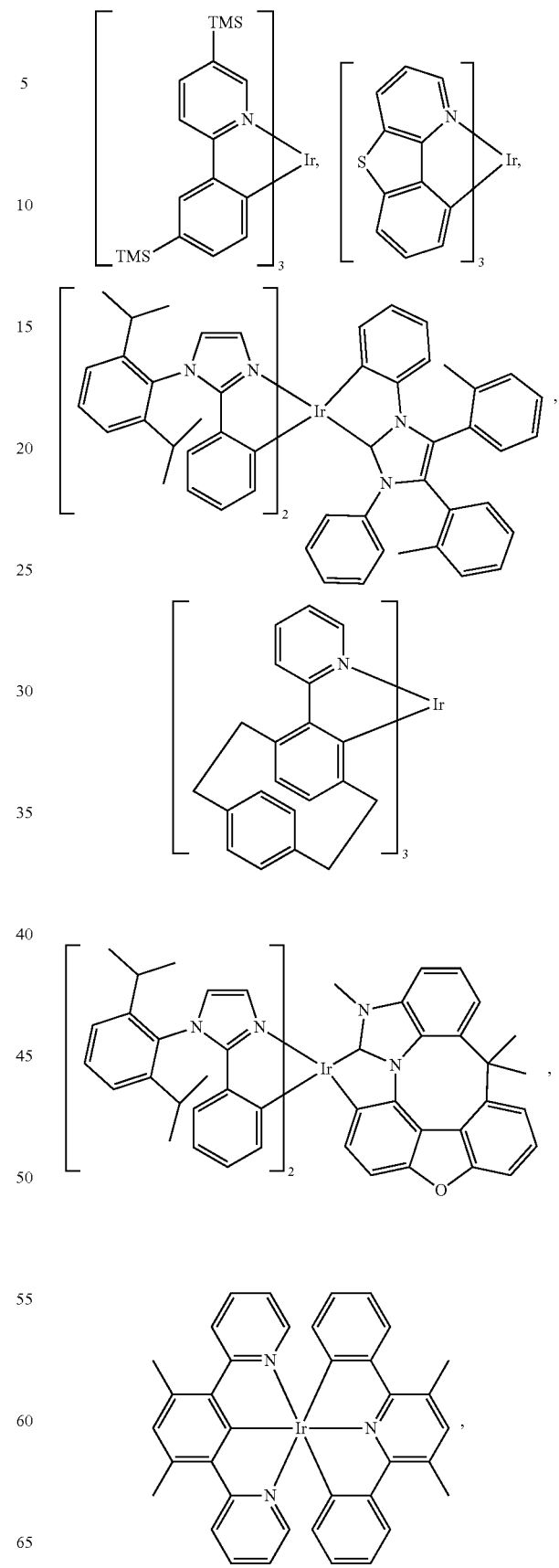

-continued
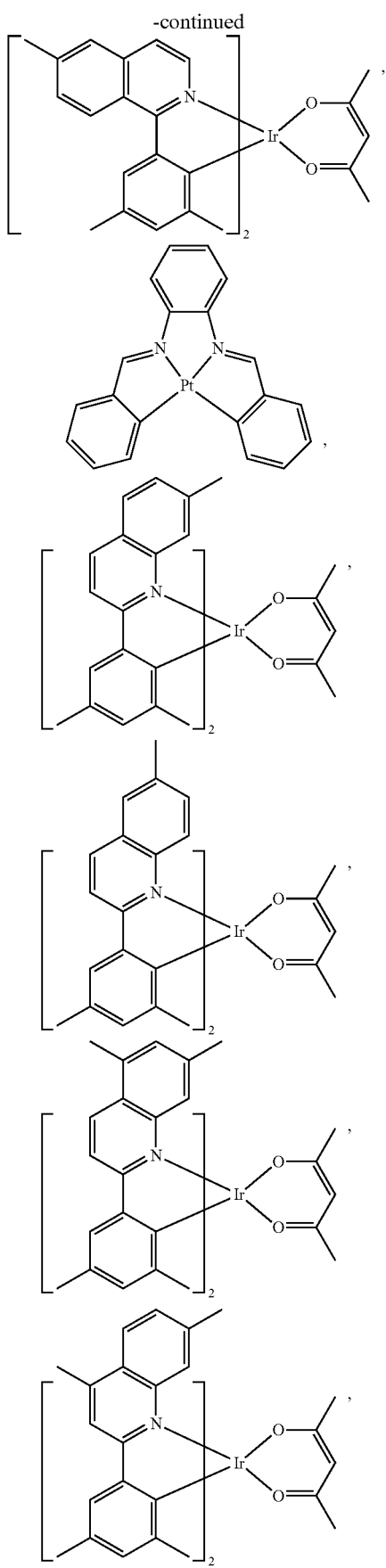
-continued
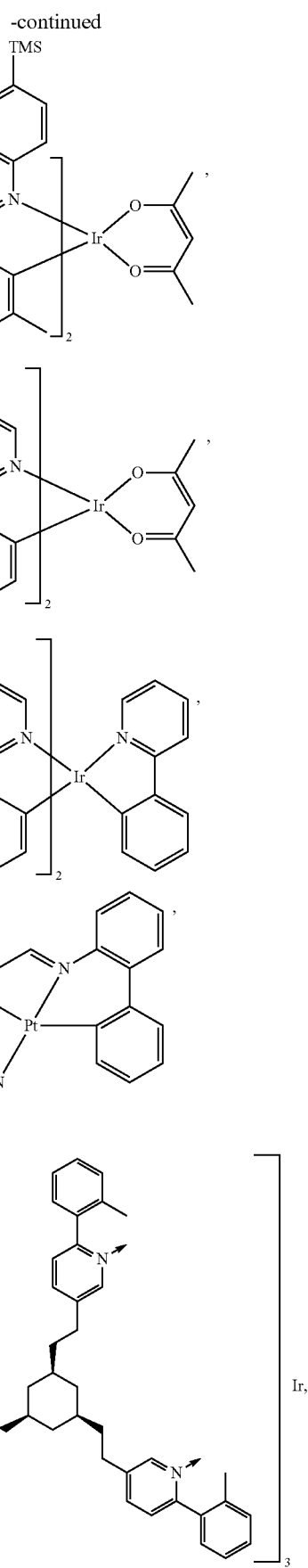

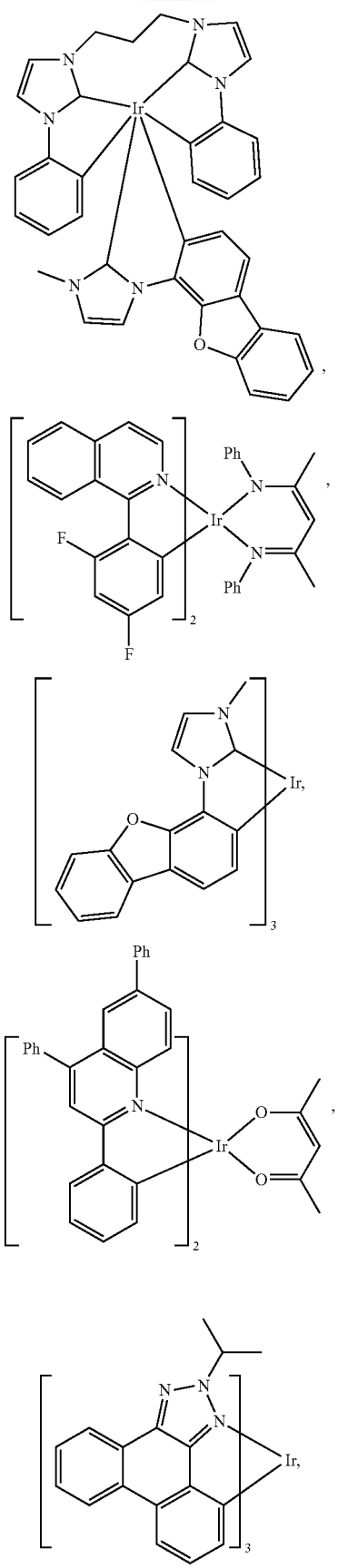
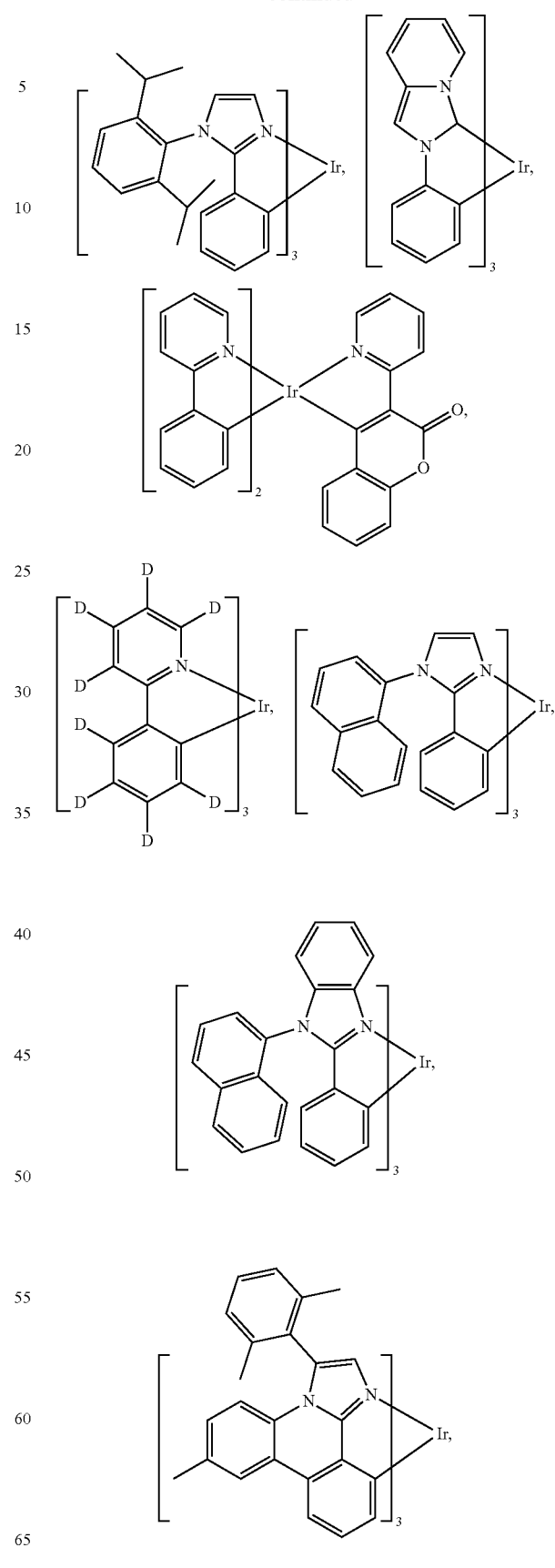

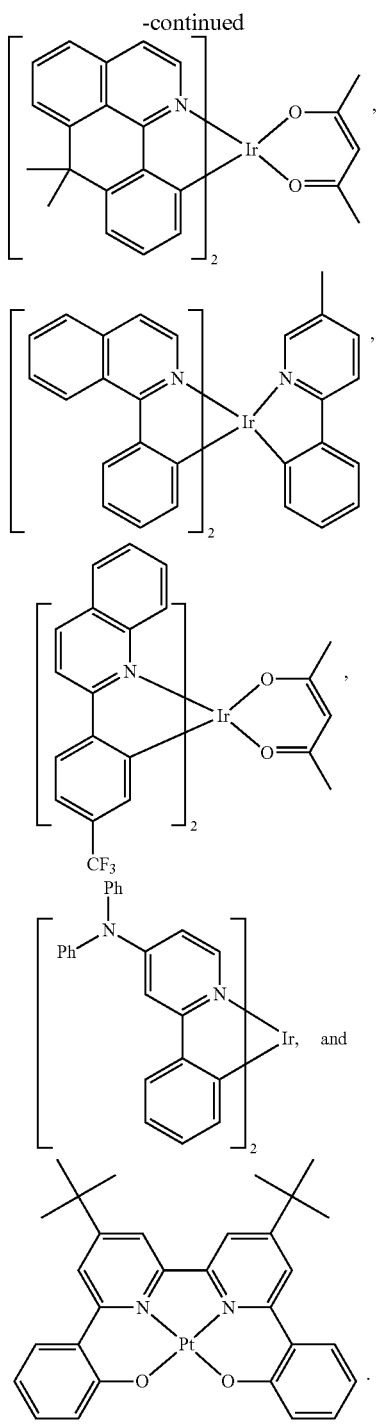

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

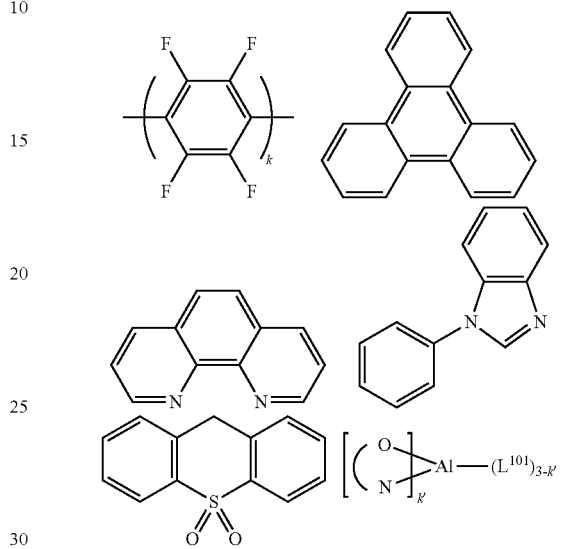

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

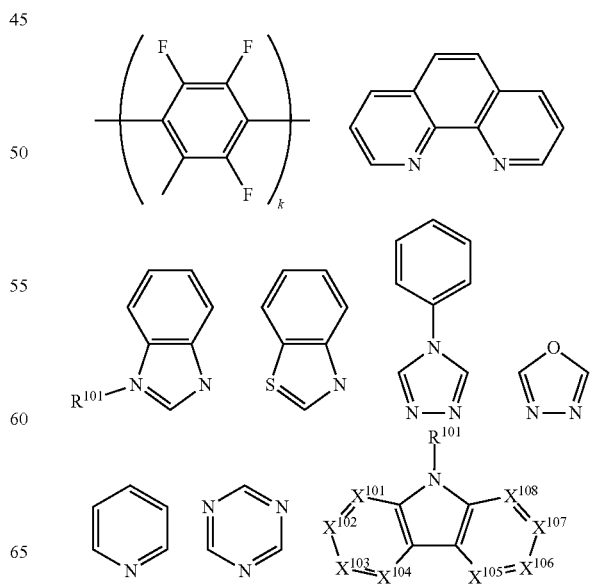

-continued

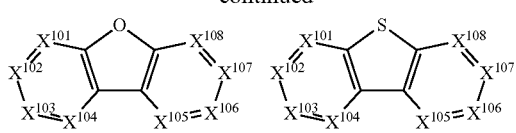

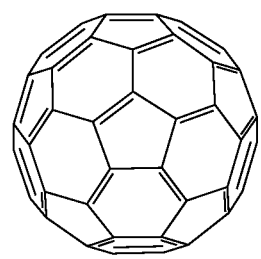

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

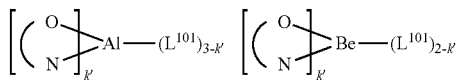

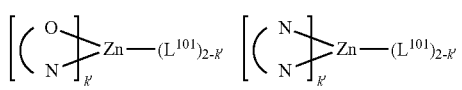

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

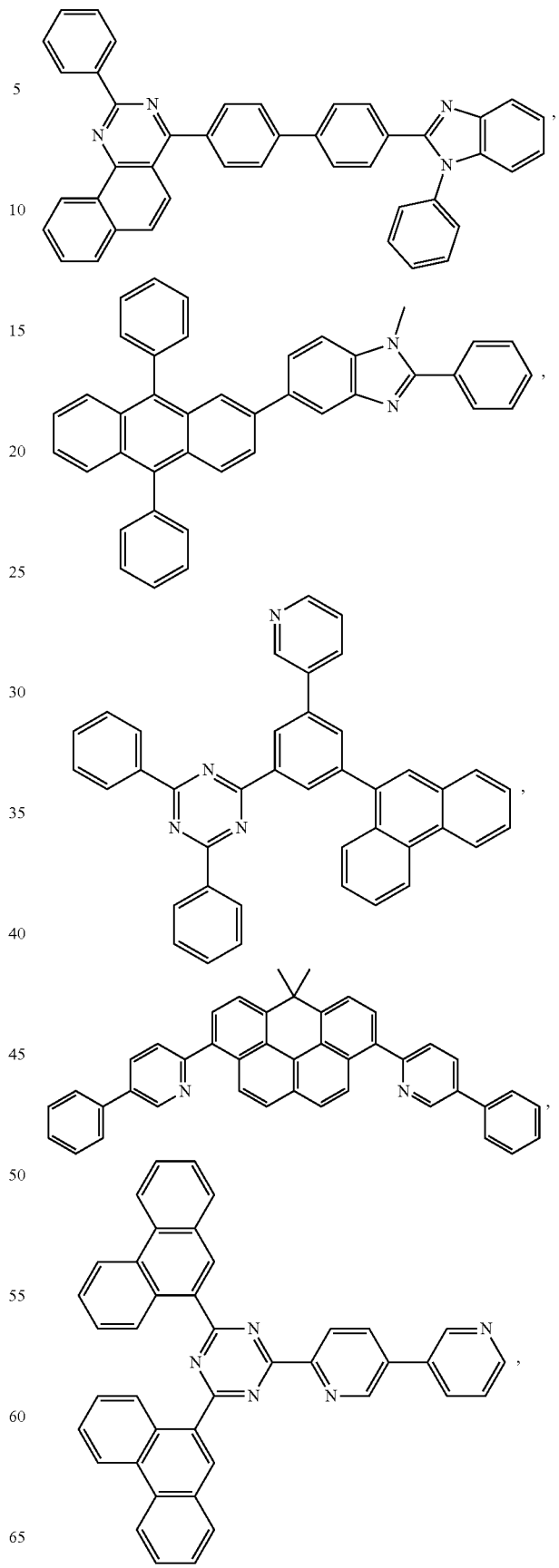

141
-continued
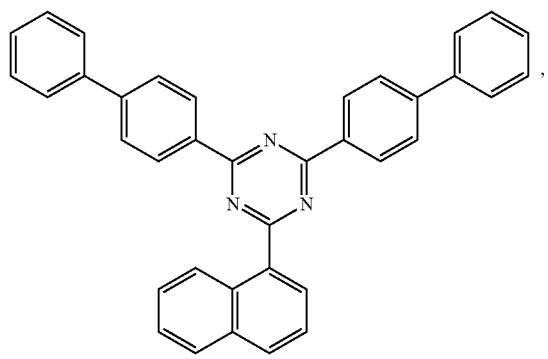
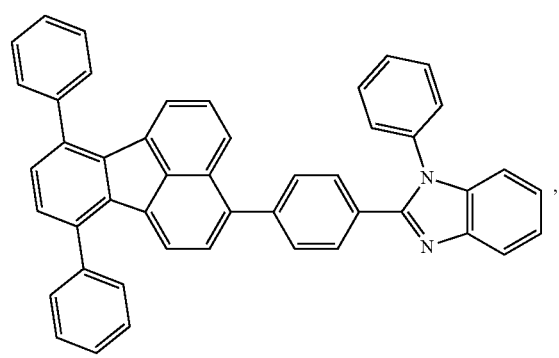
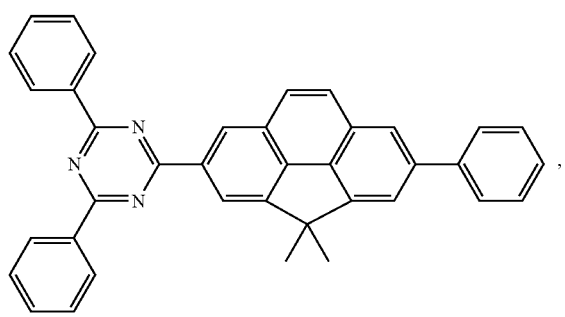
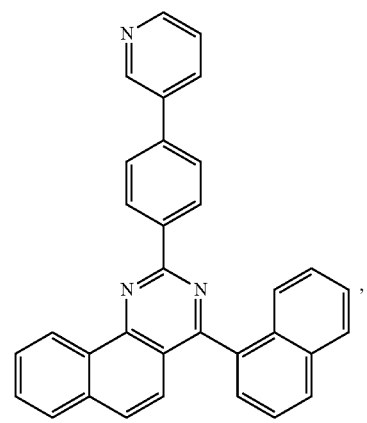
142
-continued
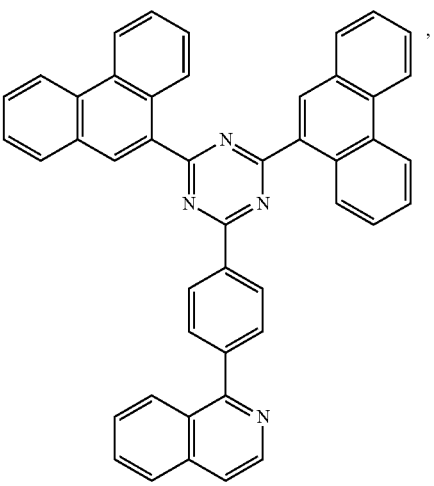
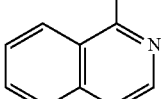
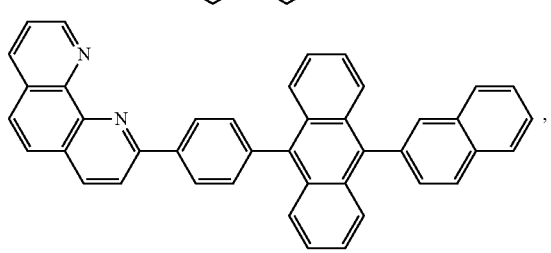
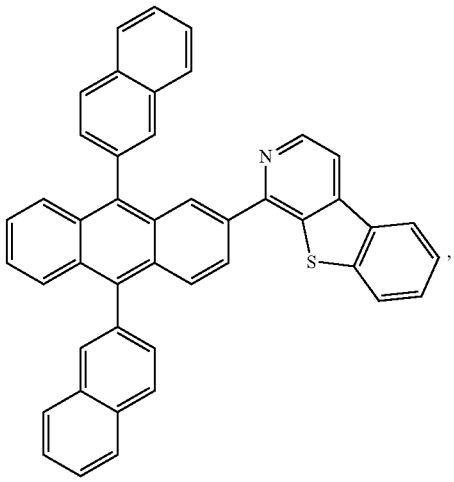
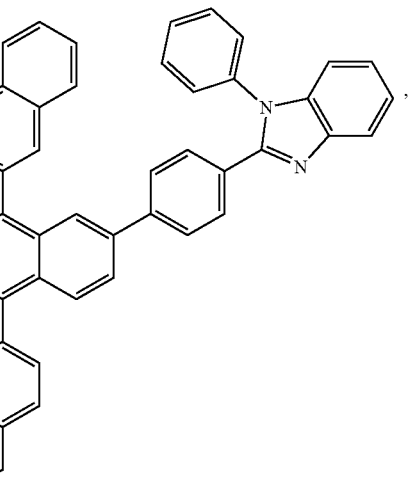

143
-continued
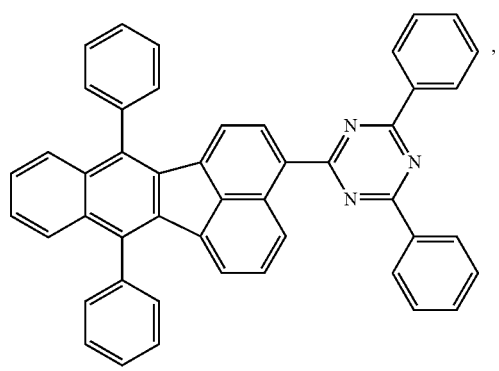
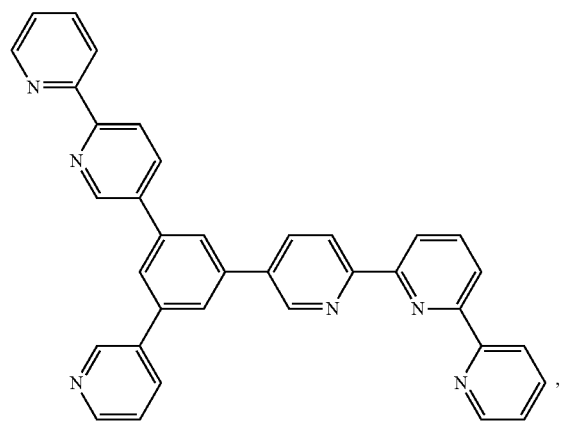
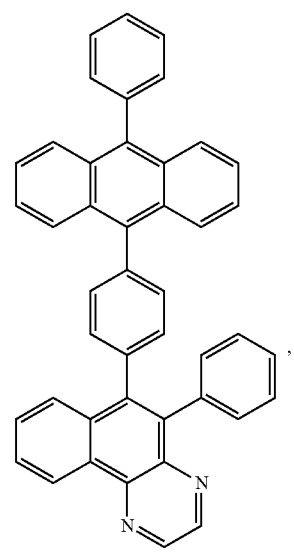
144
-continued
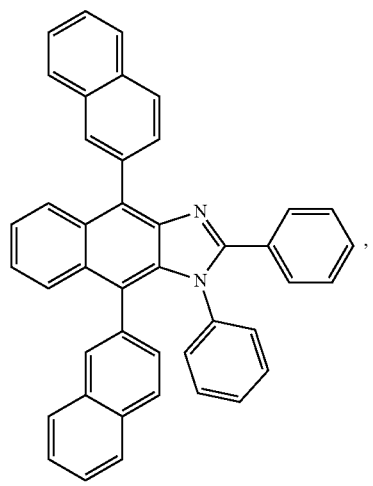
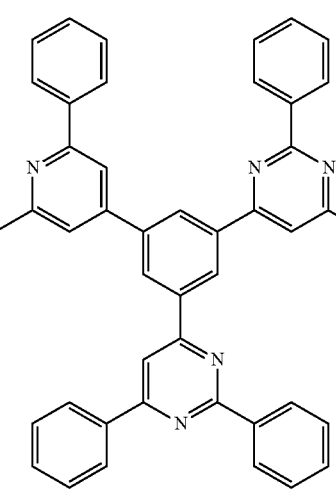
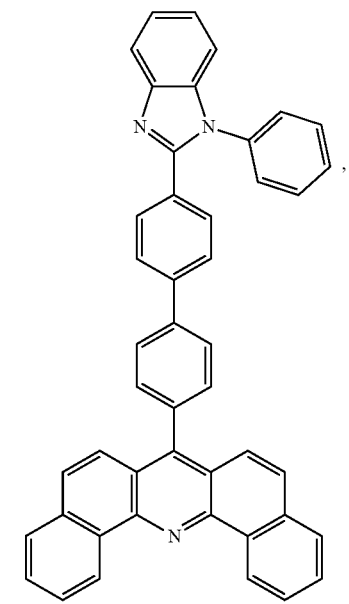

145
-continued
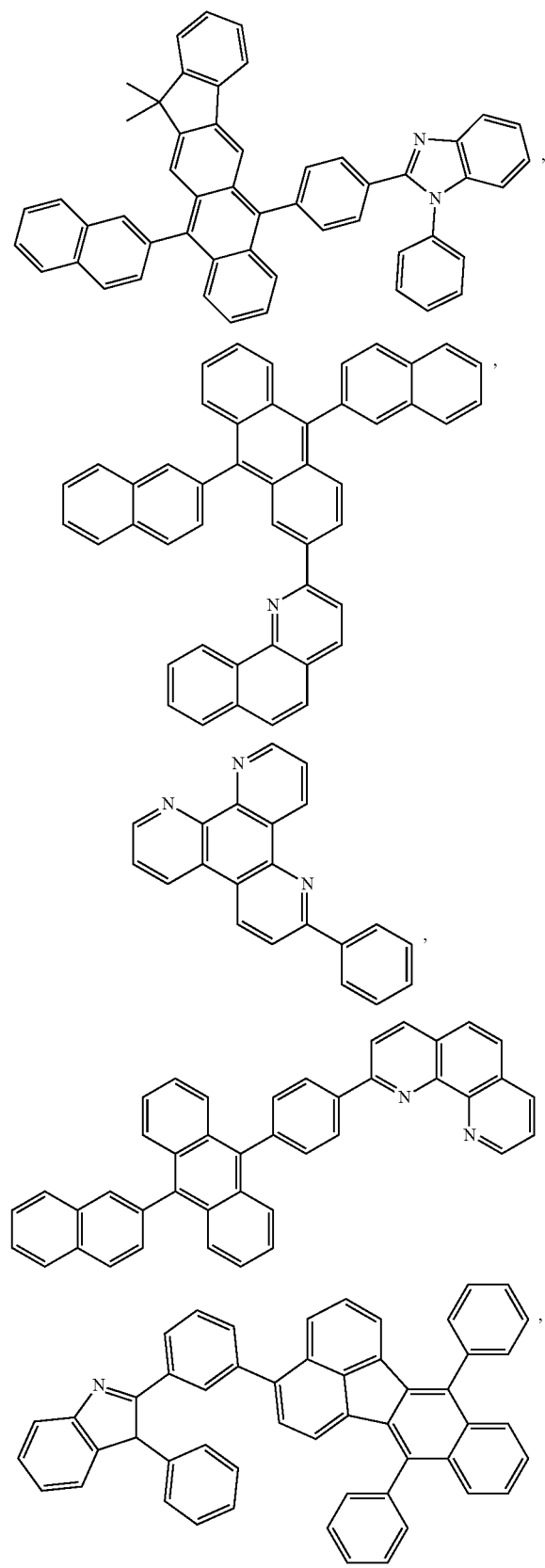
146
-continued
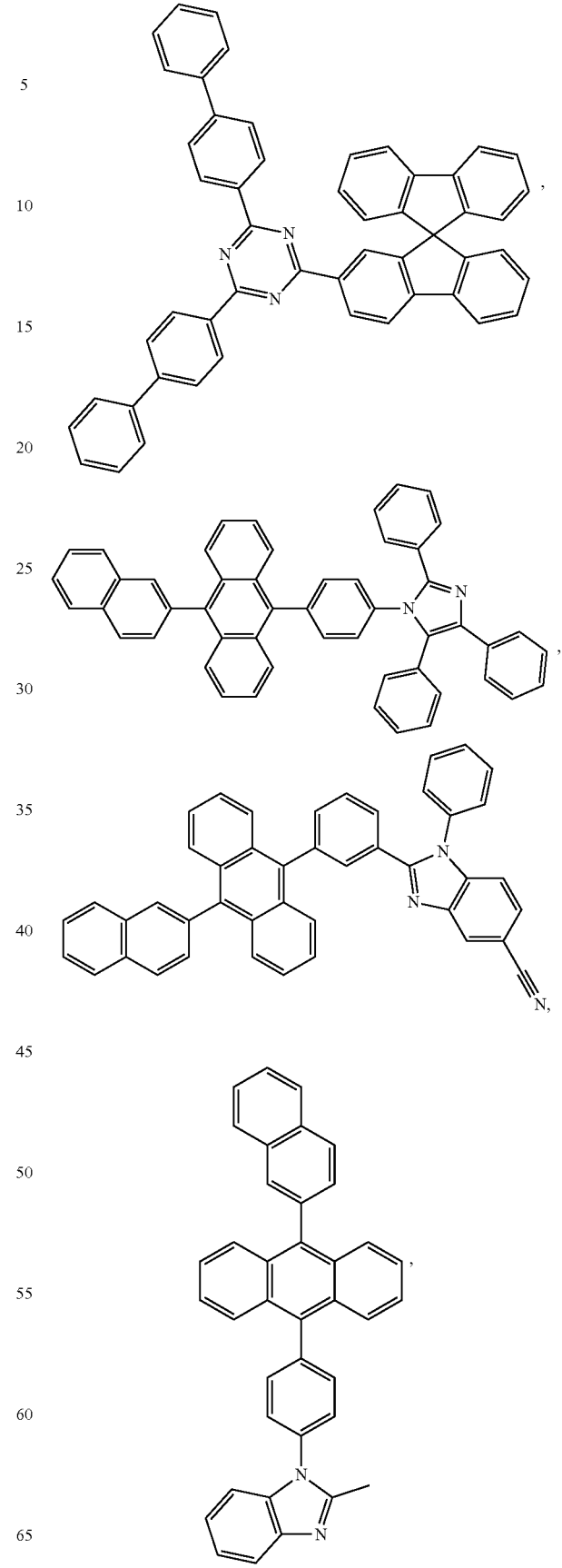

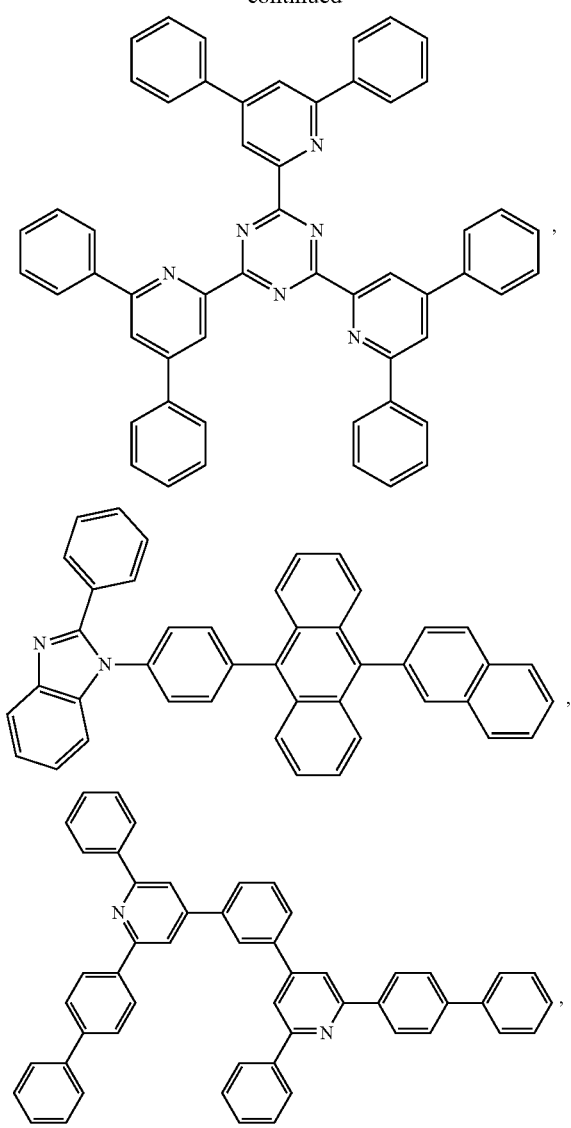

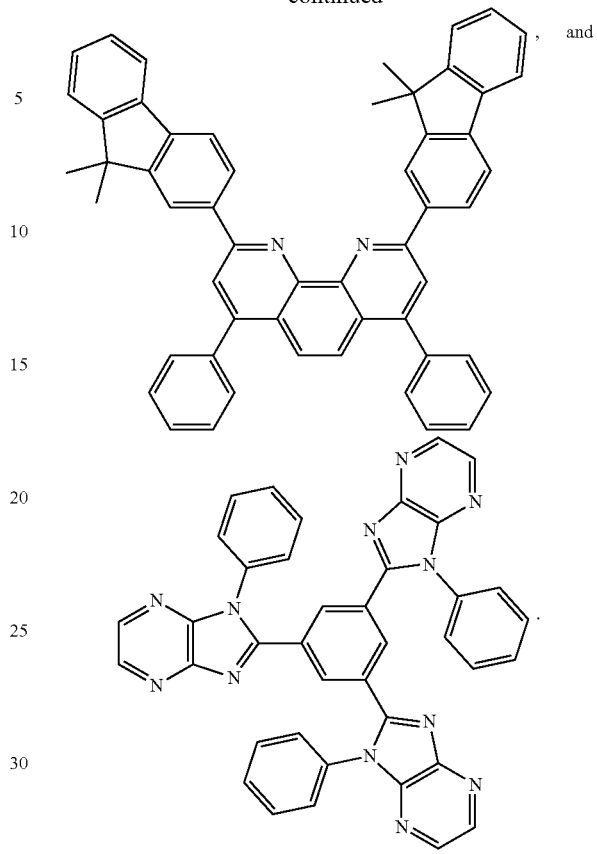

h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

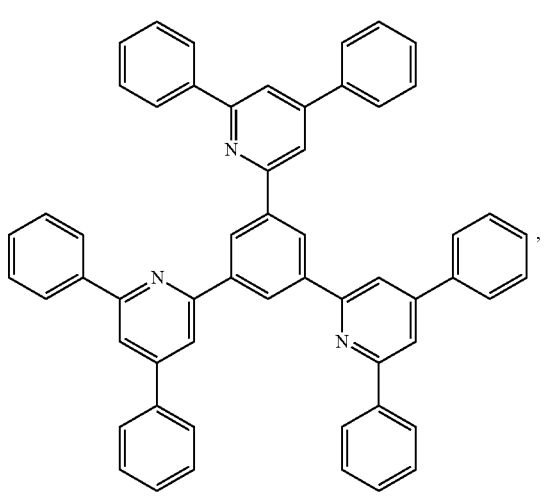

E. Experimental Data

Synthesis of 9-(2'-(9H-carbazol-9-yl)-[1,1'-biphenyl]-2-yl)-9H-3,9'-bicarbazole (Compound A)

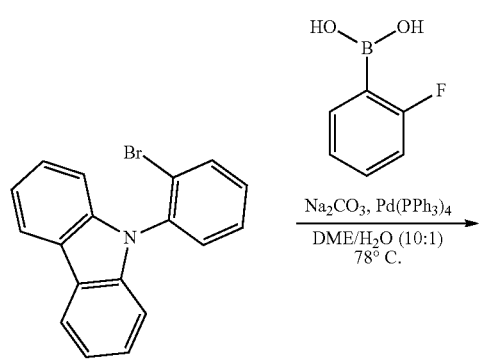

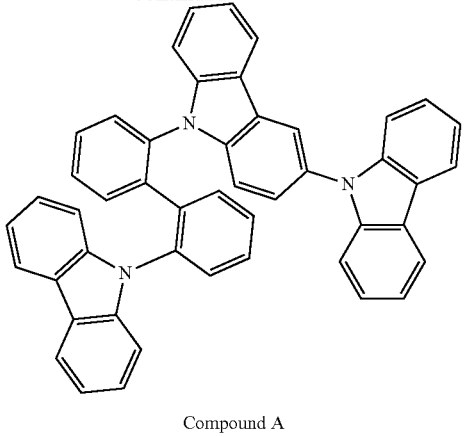

Compound A

Step 1: A 5 L flask equipped with a magnetic stirrer, condenser and thermowell was charged with 9-(2-bromophenyl)-9H-carbazole (80 g, 243 mmol), (2-fluorophenyl)boronic acid (42.1 g, 292 mmol), sodium carbonate (59.3 g, 560 mmol), 1,2-Dimethoxyethane (1569 ml) and water (157 ml). The resultant mixture was degassed with nitrogen gas for 20 minutes. Pd(PPh$_3$)$_4$ (14.06 g, 12.17 mmol) was added and degassed with nitrogen gas for 20 minutes. The reaction mixture was heated to 78° C. and stirred for 24 hours. The mixture was cooled to room temperature, two layers were separated, and aqueous layer was extracted with dichloromethane (DCM). Combined organic layer was concentrated, resulting crude residue was dissolved in 2 L Toluene and filtered through a pad of silica. Fractions containing the compound were combined and concentrated. The gummy material obtained was triturated in heptane to provide a suspension which upon filtration afforded 9-(2'-fluoro-[1,1'-biphenyl]-2-yl)-9H-carbazole (54.4 g; 66.3% yield) as a white solid.

Step 2: A 2 L flask equipped with a mechanical stirrer, condenser and thermowell was charged with 9-(2'-fluoro-[1,1'-biphenyl]-2-yl)-9H-carbazole (53 g, 157 mmol), 9H-3,9'-bicarbazole (94 g, 283 mmol), potassium phosphate (167 g, 785 mmol), NMP (262 ml) and stirred at 203° C. for 24 hours. The reaction mixture was cooled to room temperature and added to water (3 L) at 10° C. The resulting solid was filtered, washed with water and dried. The solid was then triturated in methanol, refluxing methanol, and DCM/Methanol to obtain 9-(2'-(9H-carbazol-9-yl)-[1,1'-biphenyl]-2-yl)-9H-3,9'-bicarbazole (Compound A) as a white solid (93 g, 91% yield).

Synthesis of 2,2'-di(9H-[3,9'-bicarbazol]-9-yl)-1,1'-biphenyl (Compound B)

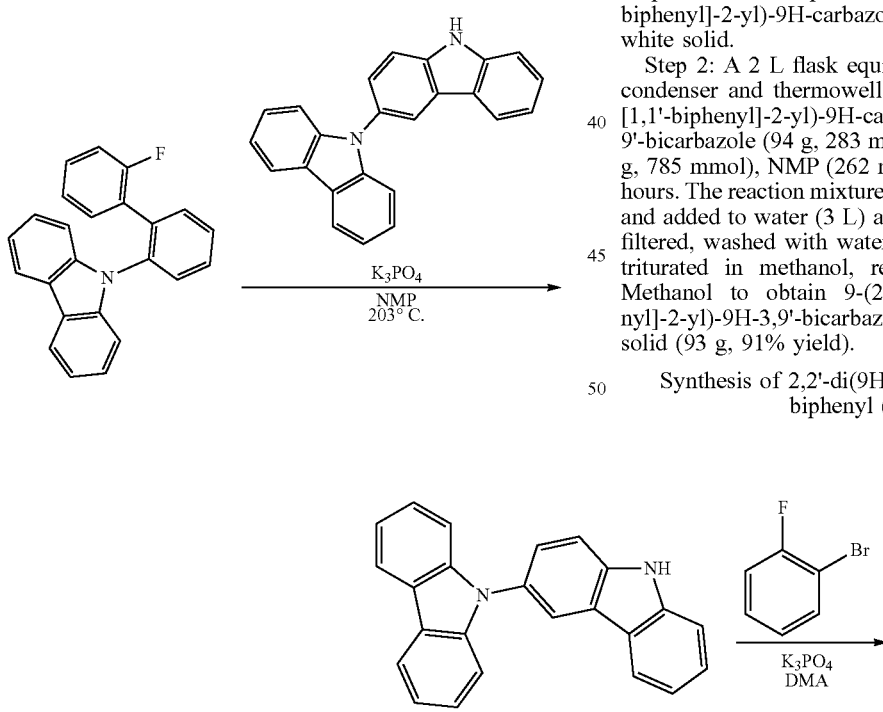

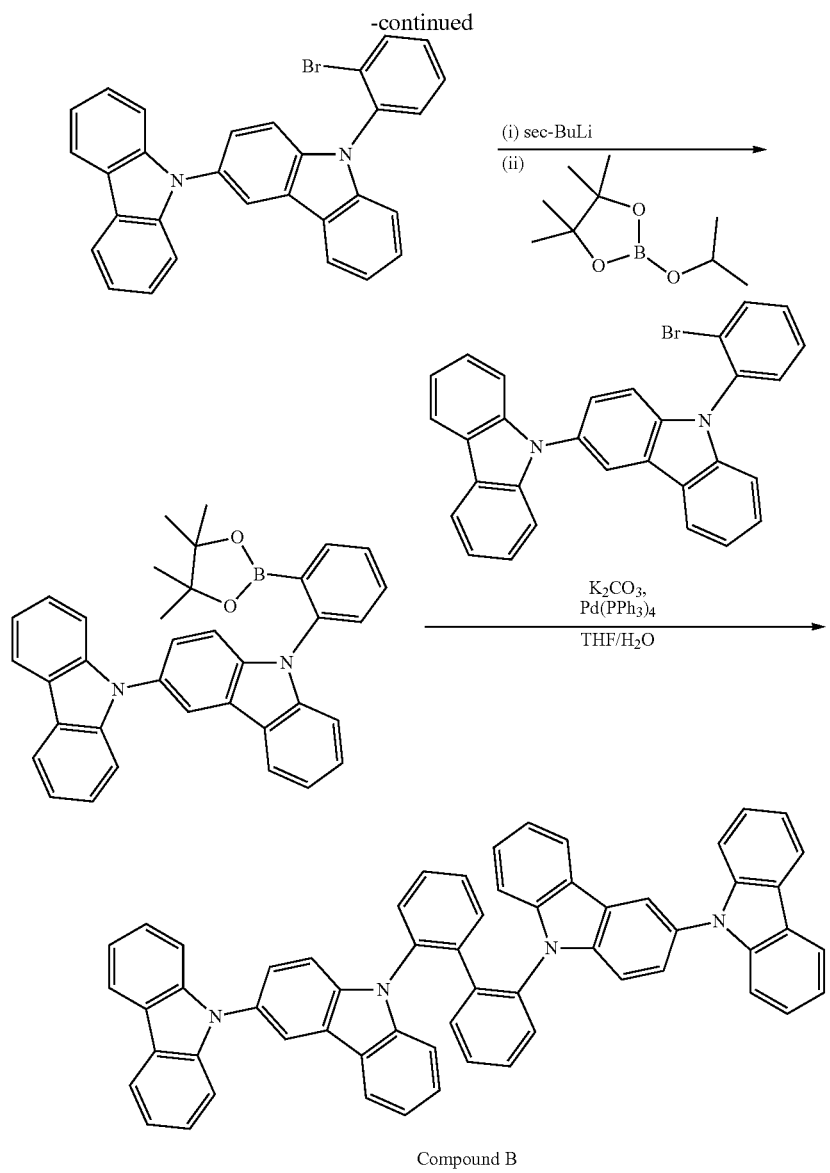

Compound B

Step 1: To a dry 500 mL thick walled reaction flask equipped with a magnetic stirrer, 9H-3,9'-bicarbazole (30 g, 90 mmol), potassium phosphate (38.3 g, 181 mmol), 1-bromo-2-fluorobenzene (14.80 ml, 135 mmol) and N,N-Dimethylacetamide (150 ml) were added under nitrogen and the flask was sealed with a threaded cap and heated to 160° C. in an oil bath. After 24 hours, thin-layer chromatography (TLC) indicated appearance of a new spot and the presence of unreacted 9H-3,9'-bicarbazole. The reaction was continued for 17 hours and cooled to room temperature. TLC indicated complete consumption of 9H-3,9'-bicarbazole. The reaction mixture was added to 2 L of ice-cold water. The brown gummy solid precipitate was filtered and washed with water and air dried. The solid was suspended in heptane and stirred for 2 hours, sonicated for 90 min and stirred for 1 hour. The suspension was filtered to provide 9-(2-bromophenyl)-9H-3,9'-bicarbazole (22.5 g, 46.2 mmol) as an off-white powder (24.2 g, 98% yield).

Step 2: To a dry 1 L 3-neck flask under nitrogen, equipped with a magnetic stirrer and thermowell, 9-(2-bromophenyl)-9H-3,9'-bicarbazole (22.5 g, 46.2 mmol) was added. Anhydrous THF (231 ml), was added via cannulation and the solution was cooled to −72° C. sec-Butyllithium (57.7 ml, 81 mmol) was added dropwise using an addition funnel over 40 minutes. The mixture was allowed to warm to −40° C. over 90 minutes. TLC indicated complete disappearance of the Bromide. The mixture was cooled down to −68° C. and 2-isopropoxy-4,4,5,5-tetramethyl-1,3,2-dioxaborolane (16.48 ml, 81 mmol) was added dropwise. The reaction mixture was slowly warmed to room temperature overnight (approx. 16 hours). The mixture was cooled in an ice bath and saturated aqueous ammonium chloride solution (100 mL) was cautiously added and stirred for 10 minutes. Water (100 mL) was added, and the organic layer was separated. The aqueous layer was extracted with DCM, dried over sodium sulfate, filtered and the filtrate was evaporated to dryness to afford a gummy off-white solid. The material was triturated in Heptane and filtered to afford 9-(2-(4,4,5,5-tetramethyl-1,3,2-dioxaborolan-2-yl)phenyl)-9H-3,9'-bicarbazole as an off-white powder (18.25 g, 86% yield).

Step 3: 9-(2-bromophenyl)-9H-3,9'-bicarbazole (12.5 g, 25.6 mmol), 9-(2-(4,4,5,5-tetramethyl-1,3,2-dioxaborolan-2-yl)phenyl)-9H-3,9'-bicarbazole (18.85 g, 28.2 mmol), potassium carbonate (10.63 g, 77 mmol), THF (55 mL) and water (21 mL) were stirred in a thick walled reaction flask equipped with a magnetic stirrer and the reaction mixture was degassed for 10 minutes. To this mixture was added Pd(PPh$_3$)$_4$ (1.482 g, 1.282 mmol) and was degassed for 5 minutes. The flask was sealed and heated to 90° C. for 3.5 days. The reaction mixture was cooled to room temperature, the organic layer was separated, and the aqueous layer was extracted with DCM. Combined organic layer was dried over sodium sulphate and filtered. The filtrate was concentrated to dryness, the resulting residue dissolved in hot toluene and passed through a silica bed. Fractions containing the product were combined and concentrated. The resulting solid was triturated in methanol for 3 hours and filtered. The solid was further triturated in acetone to obtain 2,2'-di(9H [3,9'-bicarbazol]-9-yl)-1,1'-biphenyl (Compound B) (18.25 g, 86% yield).

OLED devices were fabricated using Compound A and Compound B as either single hosts for a sky blue Ir emitter (Emitter 1) or as a cohost for a deep blue Pt emitter (Emitter 2). The device performance results are shown in Table 1 and Table 2, respectively, where the EQE and Voltage are taken at 10 mA/cm$^2$ and the lifetime (LT90) is the time to reduction of brightness to 90% of the initial luminance at a constant current density of 20 mA/cm$^2$. The following compounds were used in the devices.

Compound 1

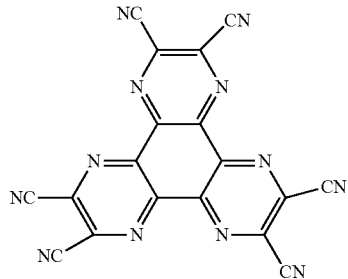

Compound 2

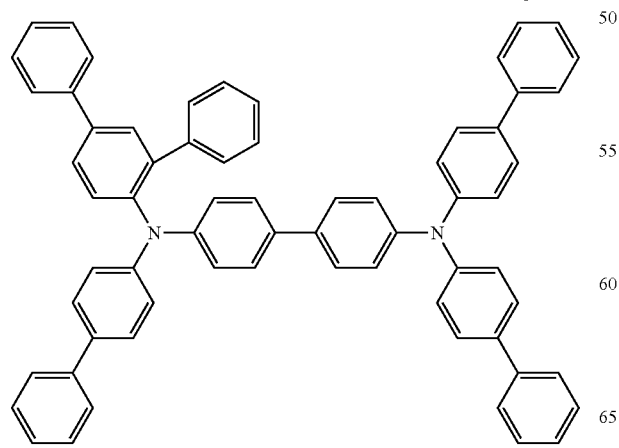

Compound 3

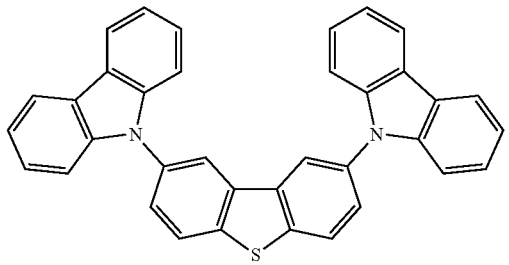

Compound 4

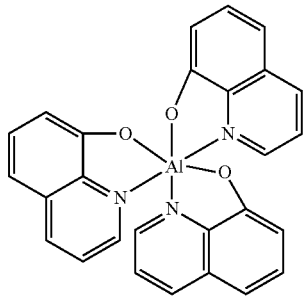

Compound 5

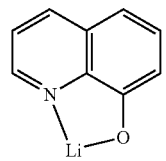

Compound 6

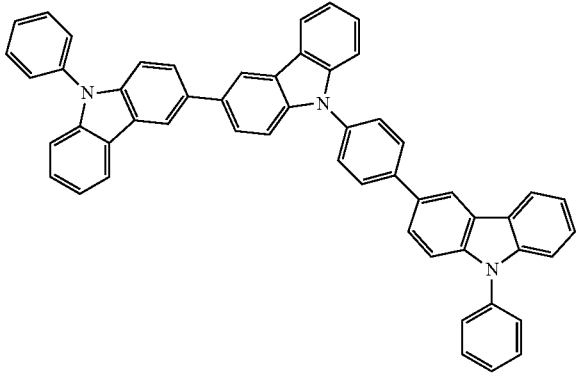

Compound 7

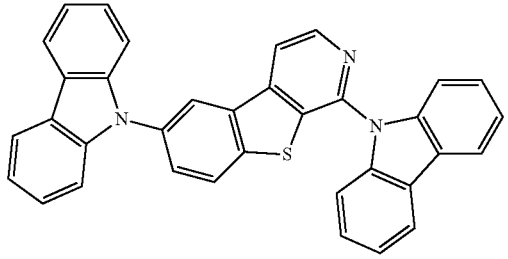

Compound 8

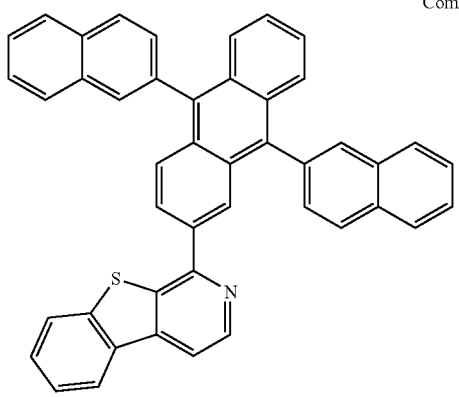

Emitter 1

Emitter 2

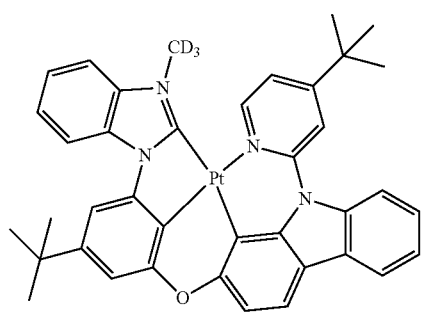

Compound A

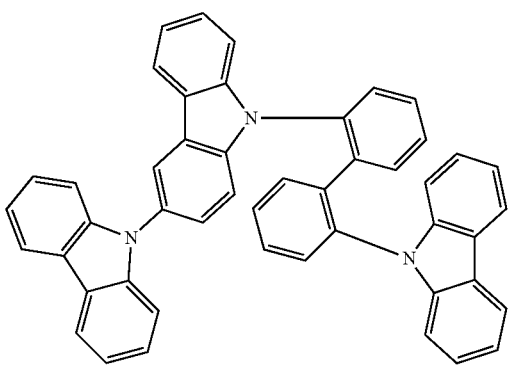

Compound B

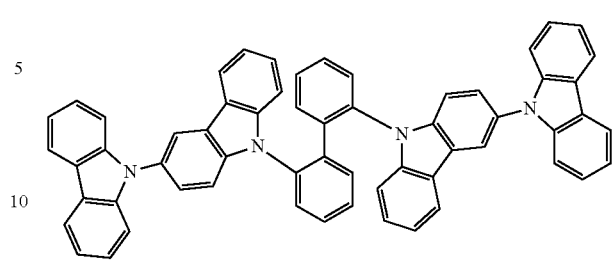

Comparison A

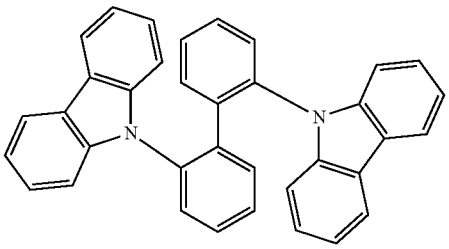

OLED structures were grown on a glass substrate precoated with an indium-tin-oxide (ITO) layer having a sheet resistance of 15-Ω/sq. Prior to any organic layer deposition or coating, the substrate was degreased with solvents and then treated with an oxygen plasma for 1.5 minutes with 50 W at 100 mTorr and with UV ozone for 5 minutes. The devices in Table 1 and Table 2 were fabricated in high vacuum ($<10^{-6}$ Torr) by thermal evaporation. The anode electrode was 750 Å of ITO. All devices were encapsulated with a glass lid sealed with an epoxy resin in a nitrogen glove box (<1 ppm of $H_2O$ and $O_2$) immediately after fabrication with a moisture getter incorporated inside the package. Doping percentages are in volume percent. The devices were grown in two different device structures.

The first set of devices had organic layers consisting of, sequentially, from the ITO surface, 100 Å of Compound 1 (HIL), 250 Å of Compound 2 (HTL), 300 Å of Host doped with 20% of Emitter 1 (EML), 50 Å of Compound 3 (BL), 300 Å of Compound 4 (ETL), 10 Å of Compound 5 (EIL) followed by 1,000 Å of Al (Cathode). The device performance for the devices with Emitter 1 and using the Host Compound A, Compound B, and Comparison A are shown in Table 1. The voltage, EQE and LT90 for the devices Example 1 and Example 2 are reported relative to the values for Comparison 1.

The second set of devices shown in Table 2 had organic layers consisting of, sequentially, from the ITO surface, 100 Å of Compound 1 (HIL), 250 Å of Compound 2 (HTL), 50 Å of Host which is used in the EML (EBL), 300 Å of Host doped with 40% of Compound 7 and doped with 12% of Emitter 2 (EML), 50 Å of Compound 7 (BL), 300 Å of Compound 5 doped with 35% of Compound 8 (ETL), 10 Å of Compound 5 (EIL) followed by 1,000 Å of Al (Cathode). The device performance for the devices with Emitter 2 and using the Host Compound A, Compound B, and Comparison A are shown in Table 2. The voltage, EQE and LT90 for the devices Example 3 and Example 4 are reported relative to the values for Comparison 2.

TABLE 1

| | | | at 10 mA/cm² | | | | at 20 mA/cm² |
|---|---|---|---|---|---|---|---|
| Device | Host | Emitter | λmax [nm] | 1931 CIE | Voltage [norm] | EQE [norm] | LT90 [norm] |
| Example 1 | Compound A | Emitter 1 | 475 | (0.175, 0.386) | 0.96 | 1.02 | 1.36 |
| Example 2 | Compound B | Emitter 1 | 476 | (0.177, 0.398) | 0.94 | 0.96 | 1.14 |
| Comparison 1 | Comparison A | Emitter 1 | 474 | (0.172, 0.376) | 1.00 | 1.00 | 1.00 |

TABLE 2

| | | | at 10 mA/cm² | | | | at 20 mA/cm² |
|---|---|---|---|---|---|---|---|
| Device | Host | Emitter | λmax [nm] | 1931 CIE | Voltage [norm] | EQE [norm] | LT90 [norm] |
| Example 3 | Compound A | Emitter 2 | 462 | (0.134, 0.157) | 1.01 | 1.01 | 1.74 |
| Example 4 | Compound B | Emitter 2 | 463 | (0.134, 0.169) | 1.00 | 0.91 | 1.50 |
| Comparison 2 | Comparison A | Emitter 2 | 461 | (0.135, 0.155) | 1.00 | 1.00 | 1.00 |

The above data shows that both of the inventive compounds, Compound A and Compound B exhibited a longer lifetime (LT90) than the comparative compound, Comparison A, as the host. The 14% to 75% longer lifetimes for Compound A and Compound B is beyond any value that could be attributed to experimental error and the observed improvement is significant. Based on the fact that Compound A and Compound B have a similar structure as Comparison A with the only difference being additional carbazole substitutions, the significant performance improvement observed in the above data was unexpected. Without being bound by any theories, this improvement may be attributed to the improved hole transporting capabilities for the biscarbazole moieties compared to the single carbazole.

What is claimed is:

1. A compound comprising a structure of Formula I

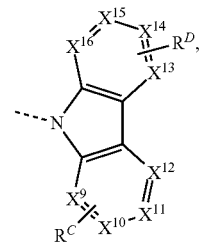

wherein $Y_i$ is

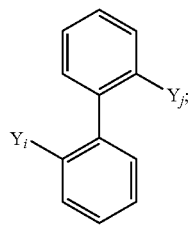

and $Y_j$ is

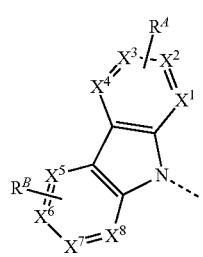

wherein:
$R^A$, $R^B$, $R^C$, and $R^D$ each independently represents zero, mono, di-substitution or the maximum allowable substitution;

each $R^A$, $R^B$, $R^C$, and $R^D$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

at least one of $R^A$, $R^B$, $R^C$, and $R^D$ comprises a carbazole moiety;

each of $X^1$-$X^{16}$ is independently C or N;

any two of $R^A$, $R^B$, $R^C$, and $R^D$ can be joined or fused together to form a ring; and wherein $Y_i$ is selected from the group consisting of:

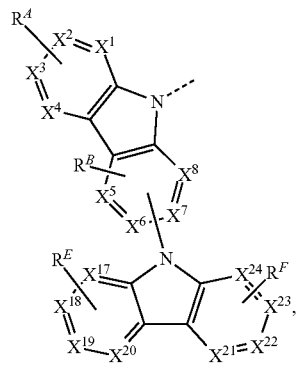

-continued

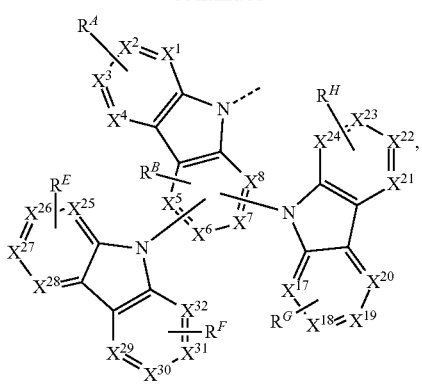

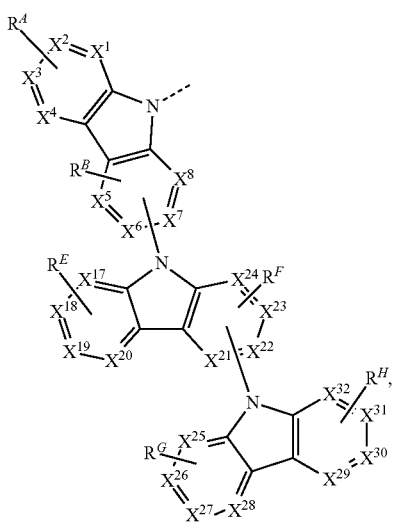

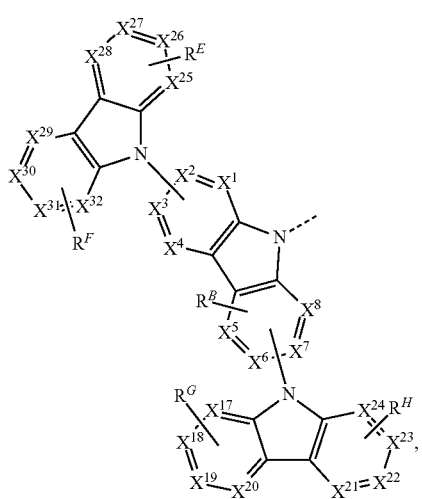

-continued

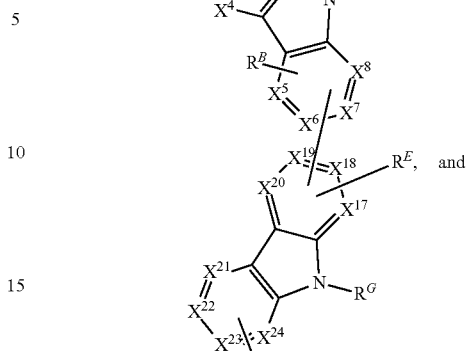

wherein $X^{17}$-$X^{32}$ are each independently C or N;

$R^E$, $R^F$, $R^G$, and $R^H$ each independently represents zero, mono, di-substitution or the maximum allowable substitution;

each $R^E$, $R^F$, $R^G$, and $R^H$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and any two of $R^E$, $R^F$, $R^G$, and $R^H$ can be joined or fused together to form a ring.

2. The compound of claim 1, wherein each $R^A$, $R^B$, $R^C$, and $R^D$ is independently a hydrogen or a substituent selected from the group consisting of deuterium, fluorine, alkyl, cycloalkyl, heteroalkyl, boryl, alkoxy, aryloxy, amino, silyl, alkenyl, cycloalkenyl, heteroalkenyl, aryl, heteroaryl, nitrile, isonitrile, sulfanyl, and combinations thereof.

3. The compound of claim 1, wherein two of $R^A$, $R^B$, $R^C$, and $R^D$ are joined together to form a fused 5-membered or 6-membered carbocyclic or heterocyclic ring.

4. The compound of claim 1, wherein at least one of $X^1$-$X^{16}$ is N.

5. The compound of claim 1, wherein $X^1$-$X^{16}$ are C.

6. The compound of claim 1, wherein $Y_i$ is selected from the group consisting of $Y_1$-$Y_{36}$, and $Y_j$ is selected from the group consisting of $Y_1$-$Y_{43}$, wherein $Y_1$-$Y_{43}$ have the following structures:

161
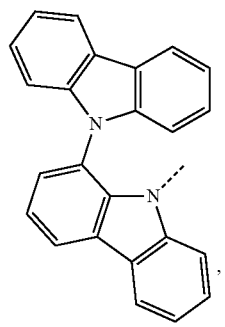
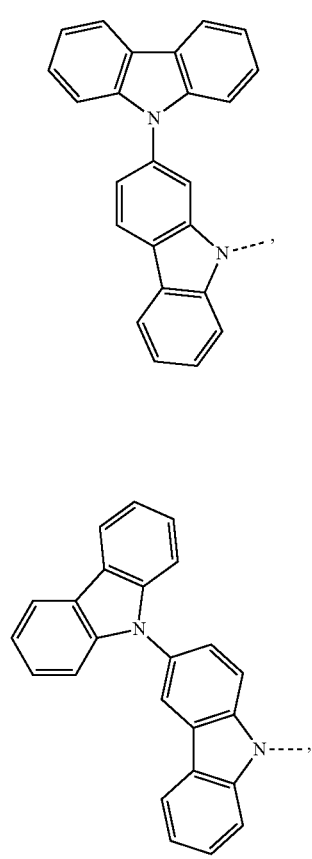
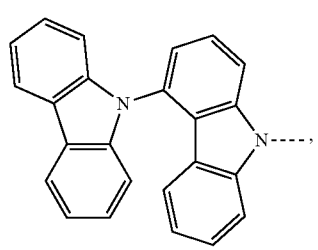
162
-continued
Y1
Y2
Y3
Y4
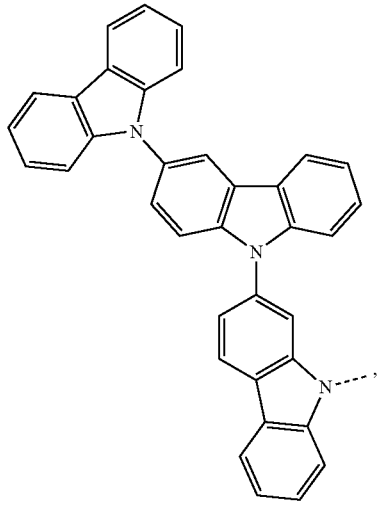
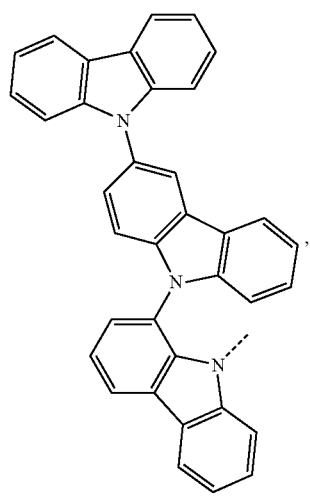
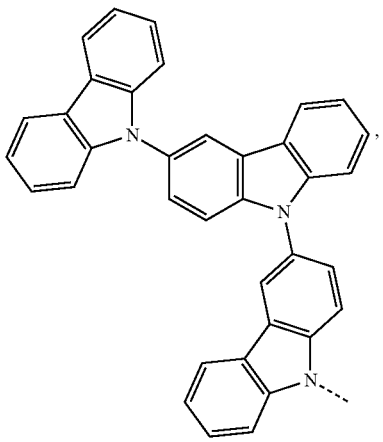
Y5
Y6
Y7

Y8
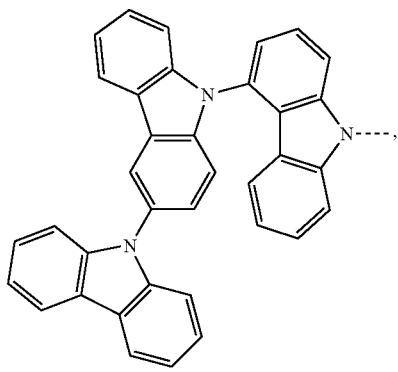
Y9
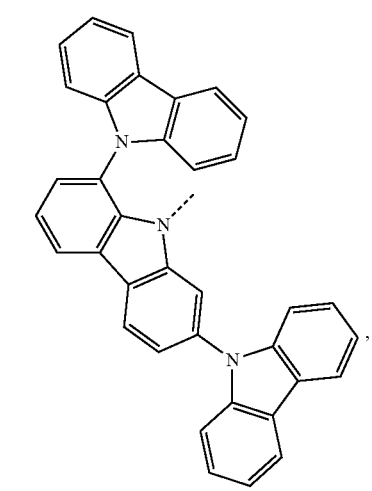
Y10
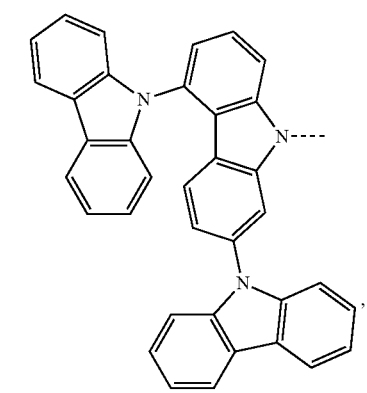
Y11
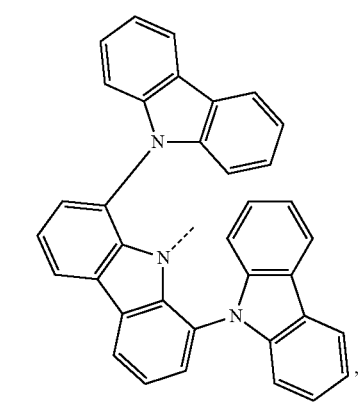
Y12
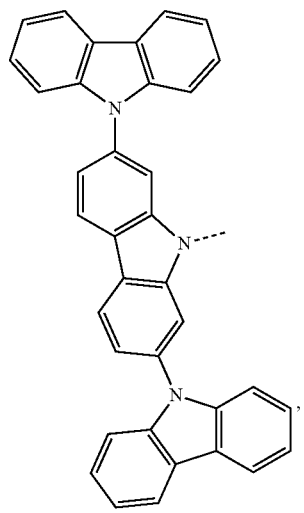
Y13
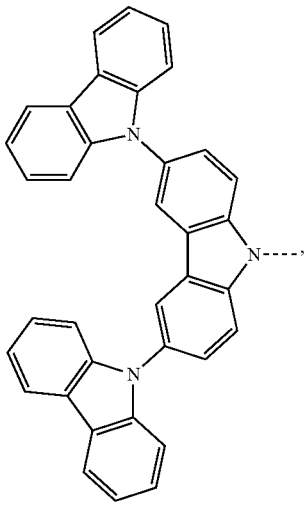
Y14
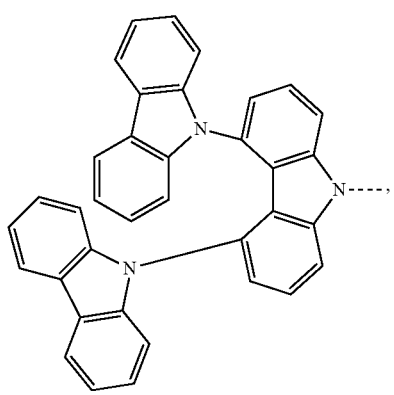

-continued
Y15
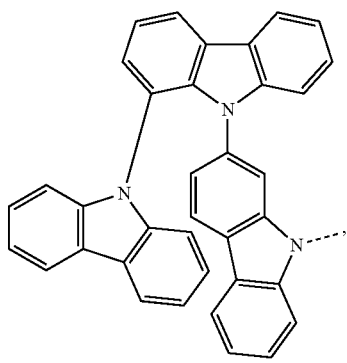
Y16
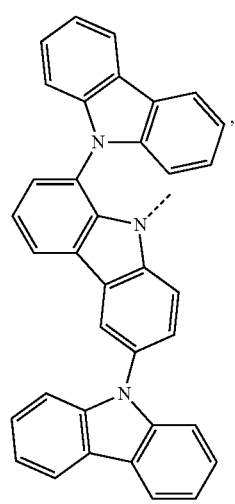
Y17
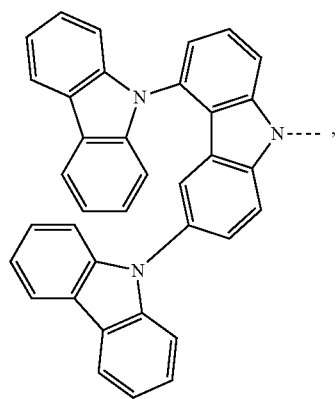
-continued
Y18
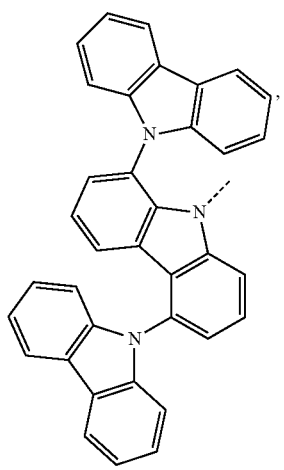
Y19
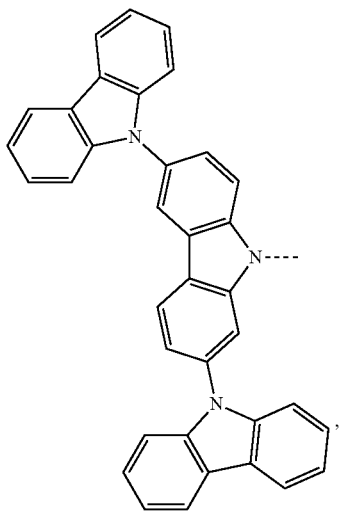
Y20
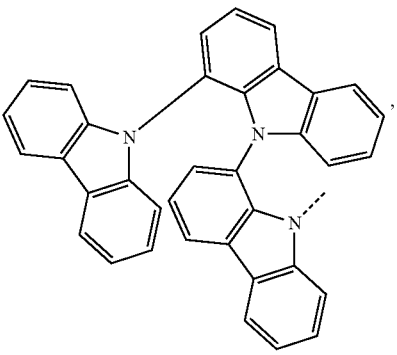

| | |
|---|---|
| Y21 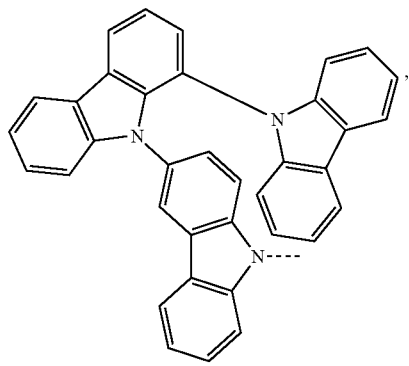 | Y25 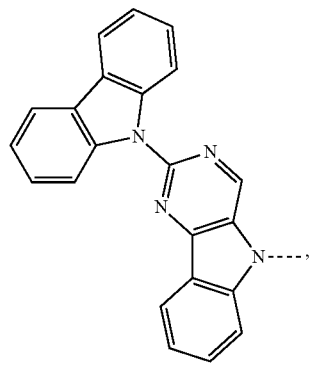 |
| Y22 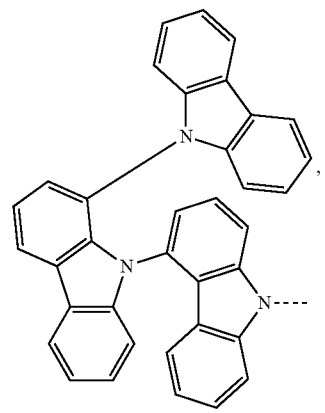 | Y26 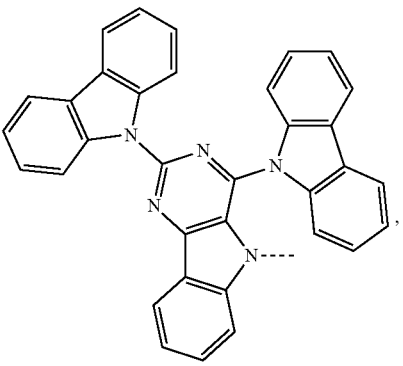 |
| Y23 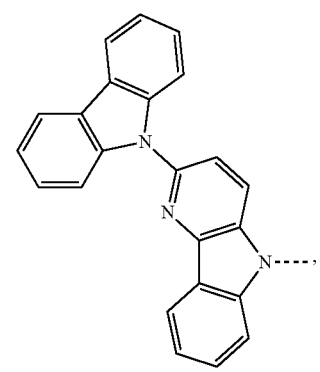 | Y27 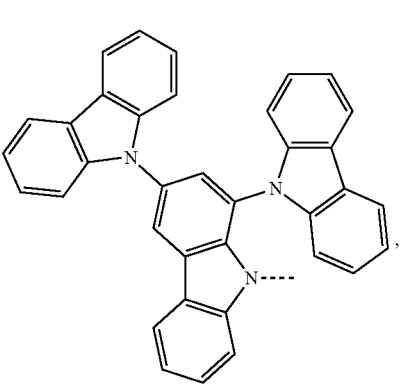 |
| Y24 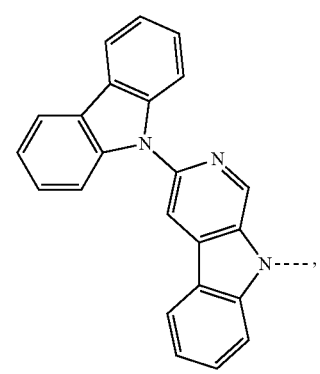 | Y28 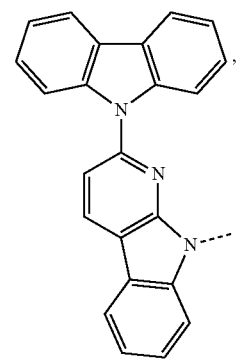 |

169
-continued
Y29 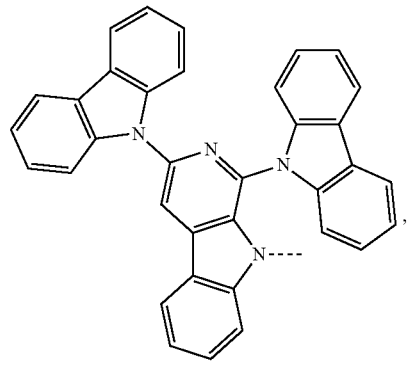
Y30 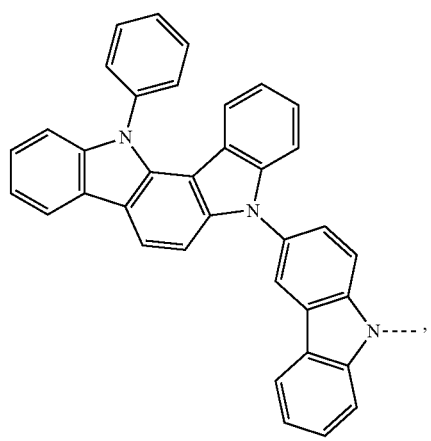
Y31 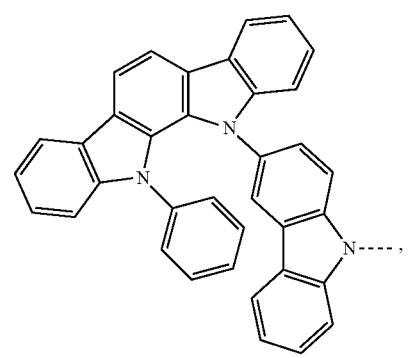
Y32 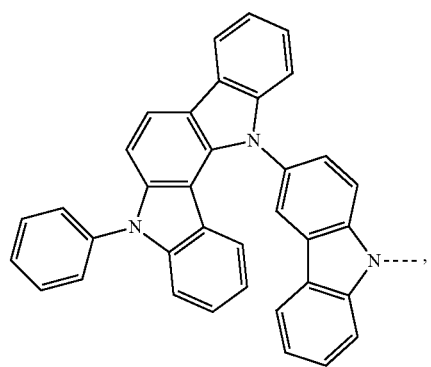
170
-continued
Y33 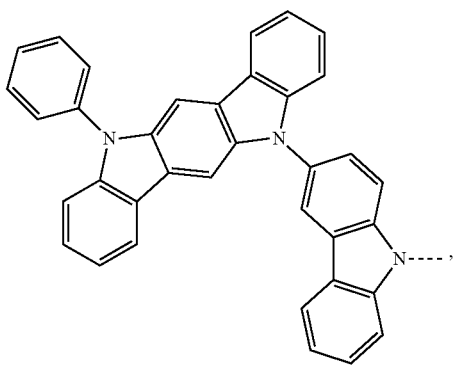
Y34 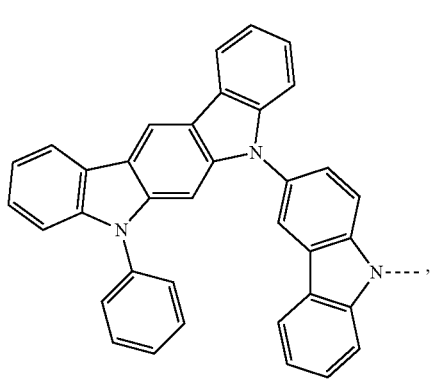
Y35 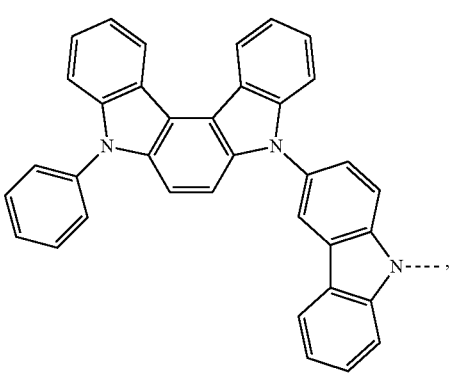
Y36 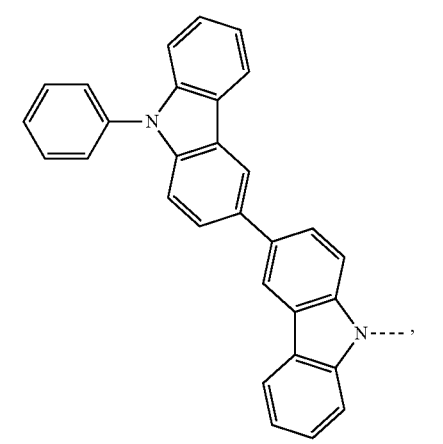

-continued
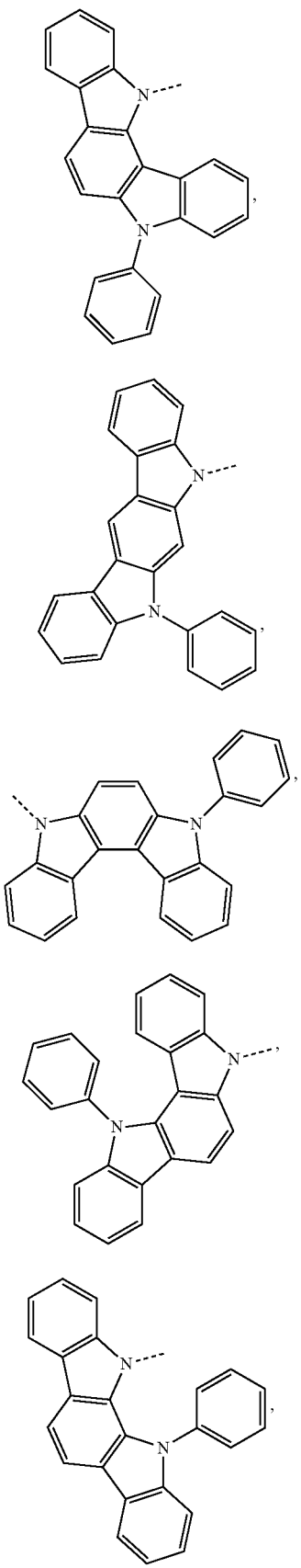
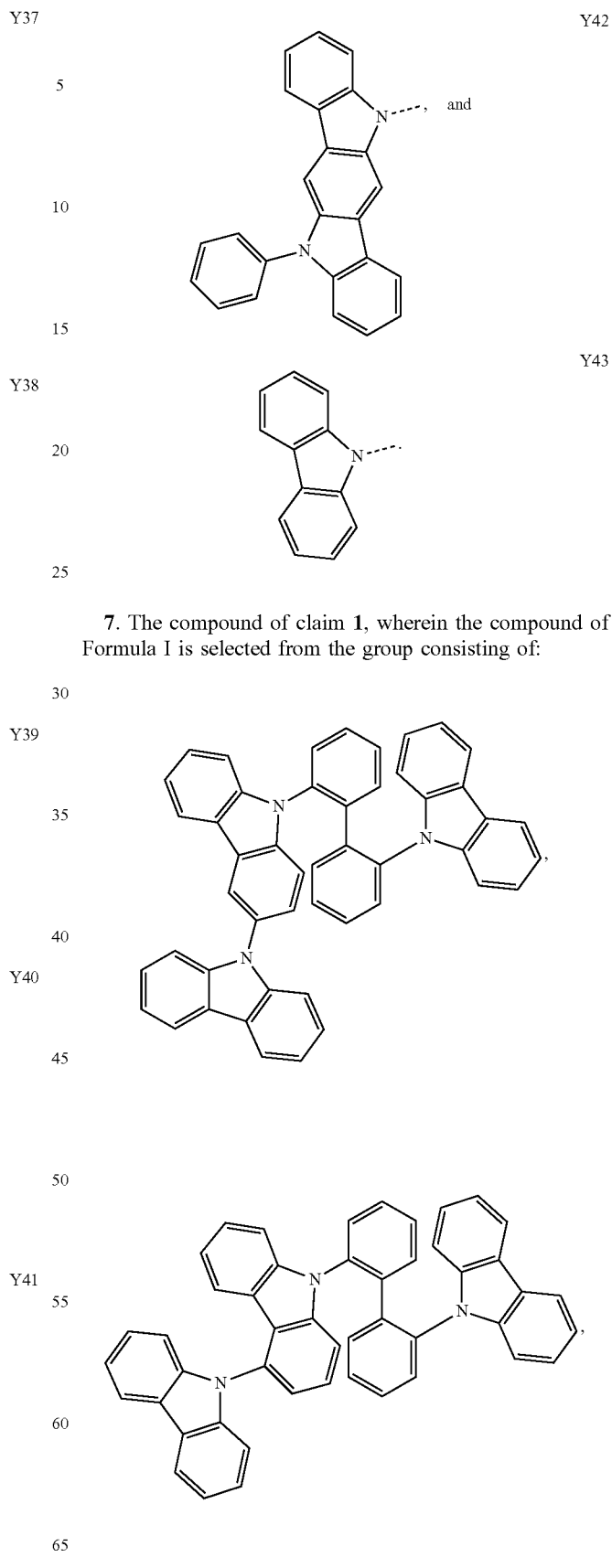
7. The compound of claim 1, wherein the compound of Formula I is selected from the group consisting of:

173
-continued
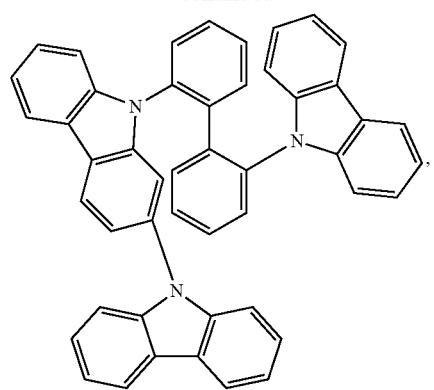
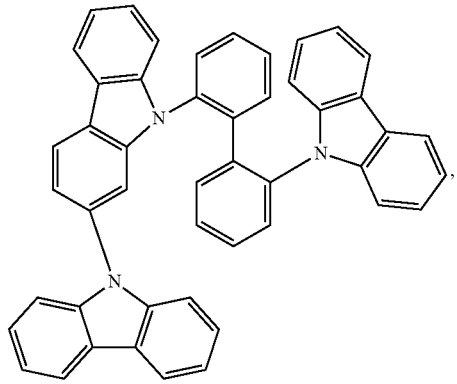
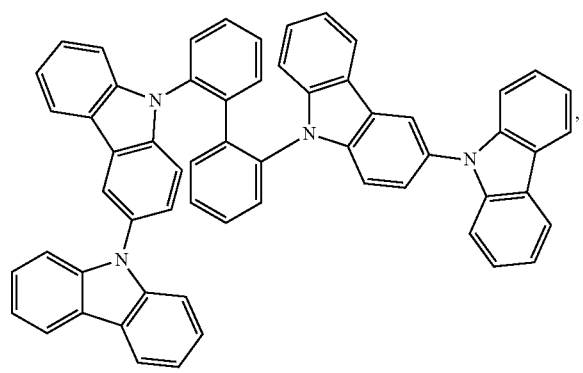
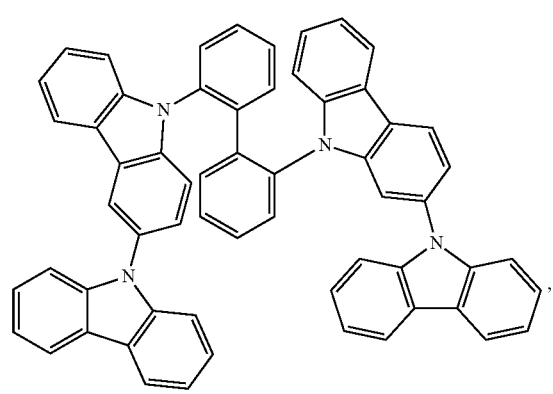
174
-continued
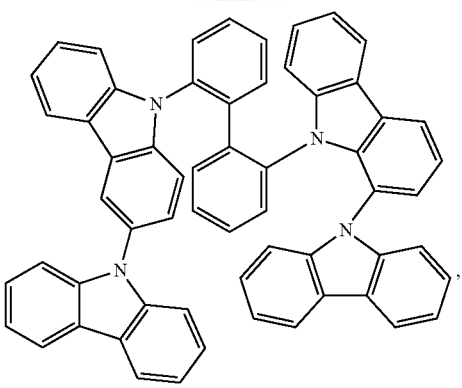
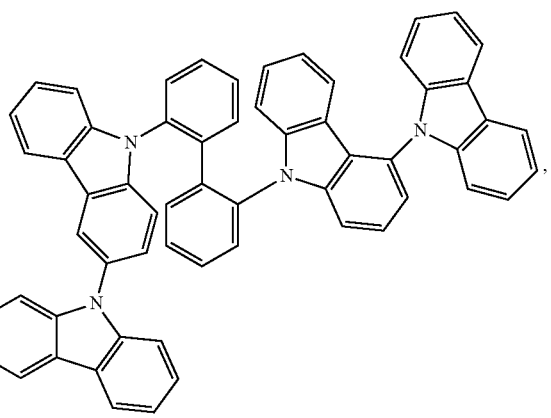
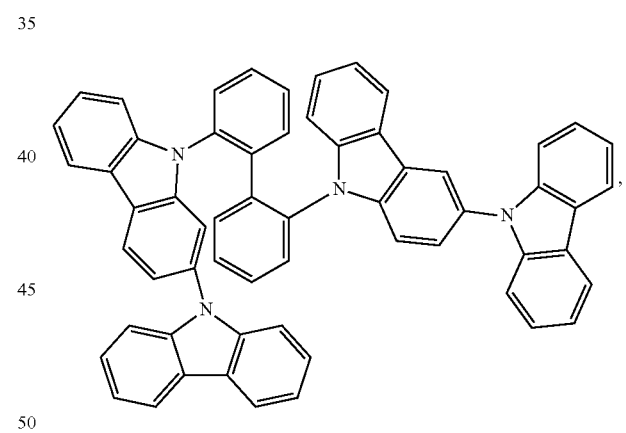
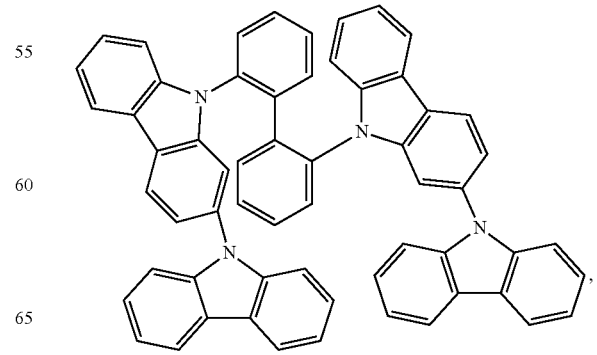

-continued
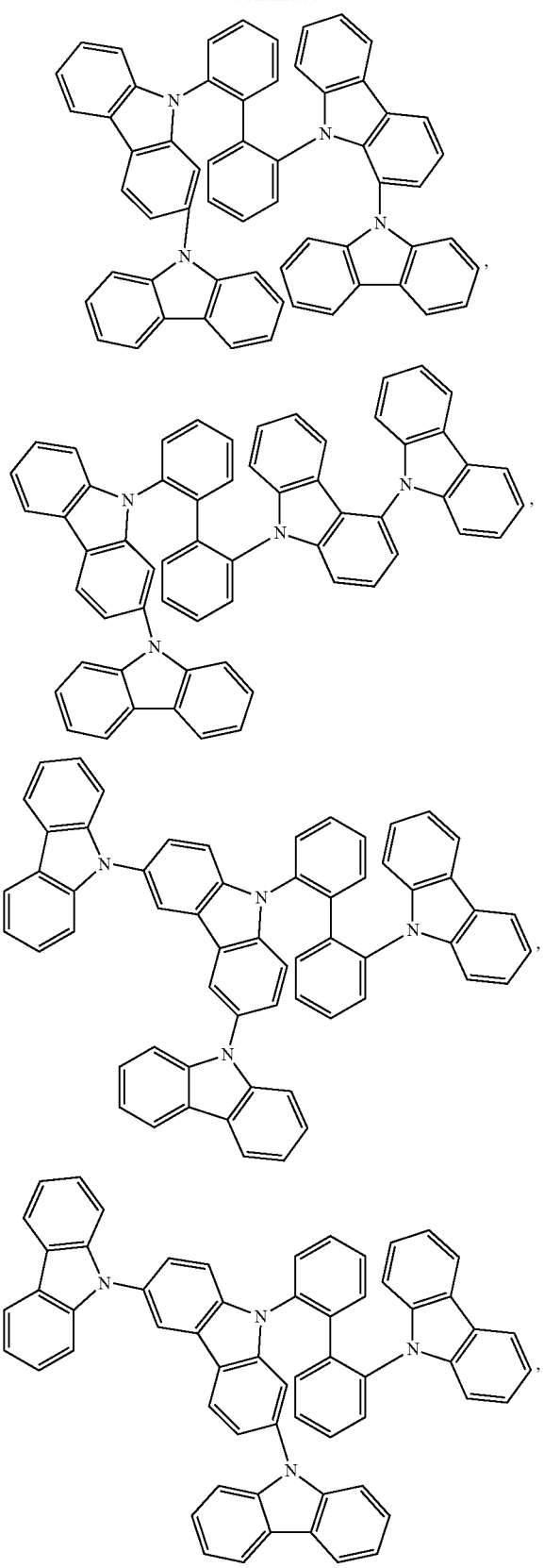
-continued
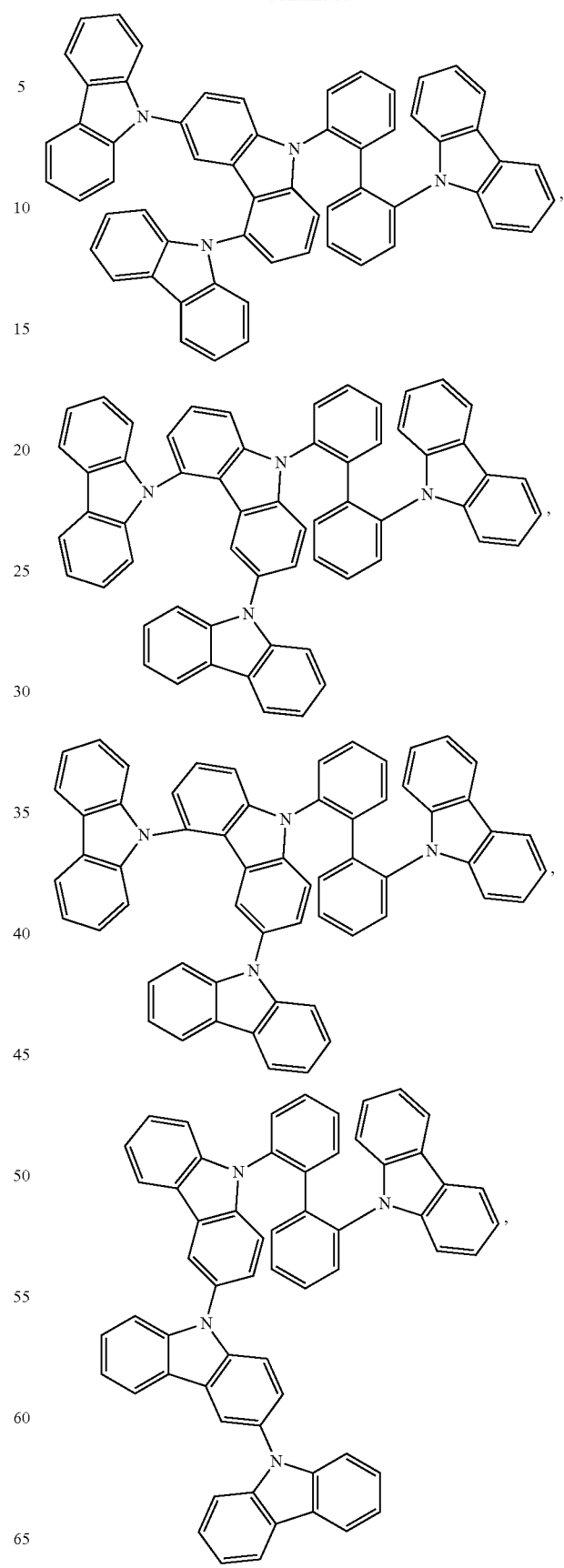

177
-continued
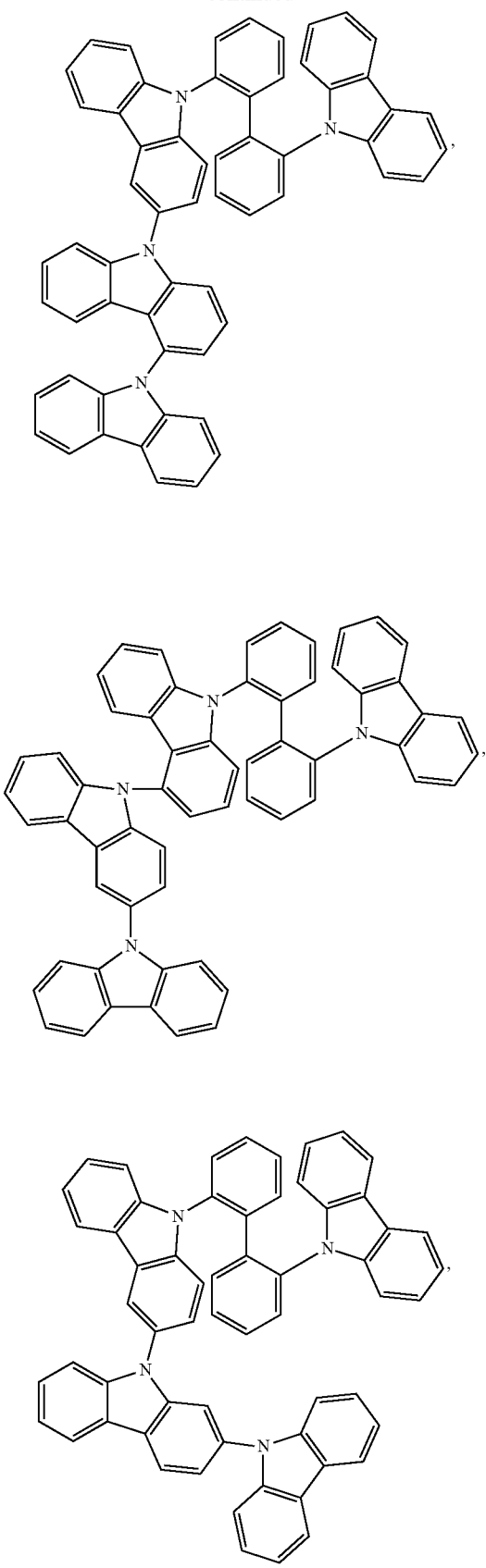
178
-continued
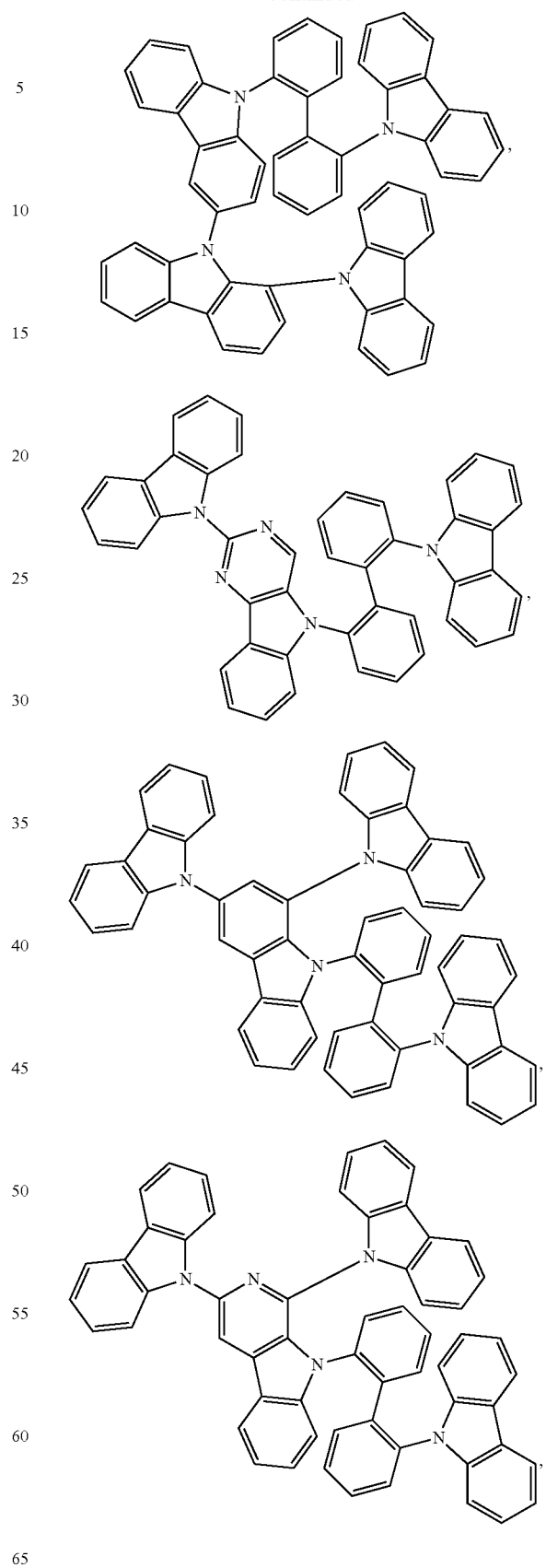

179
-continued
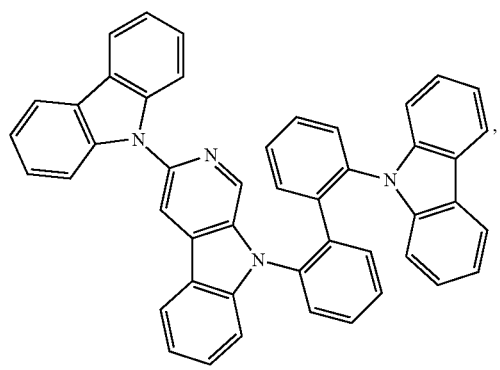
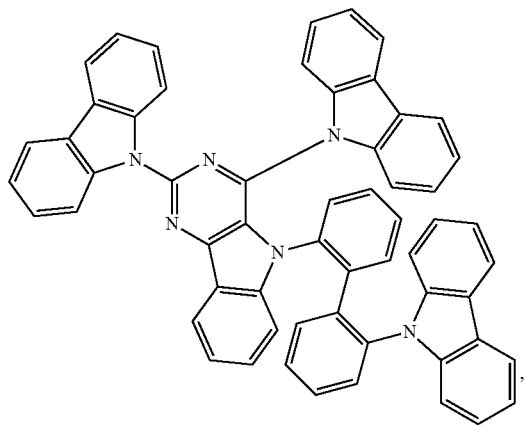
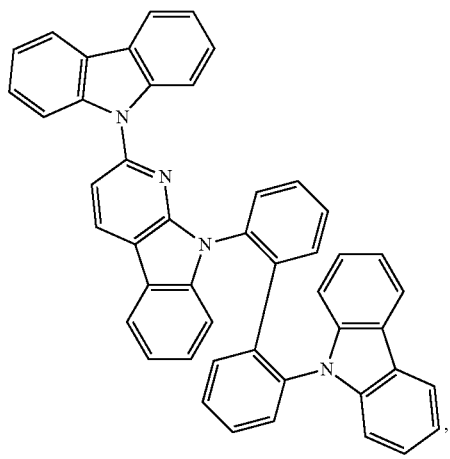
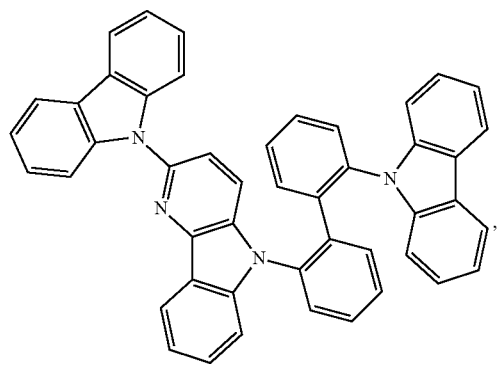
180
-continued
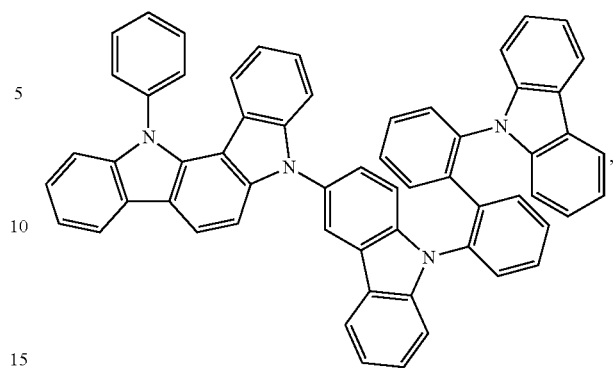
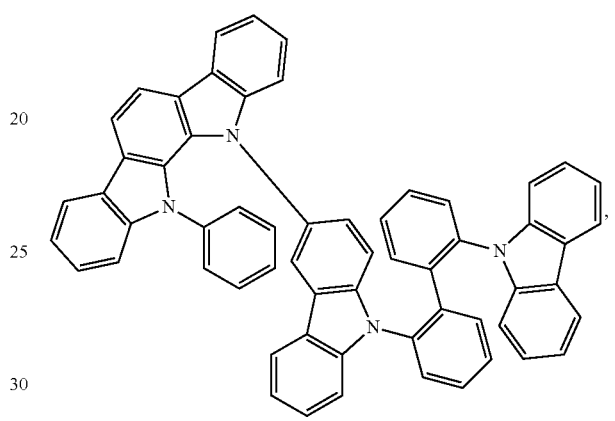
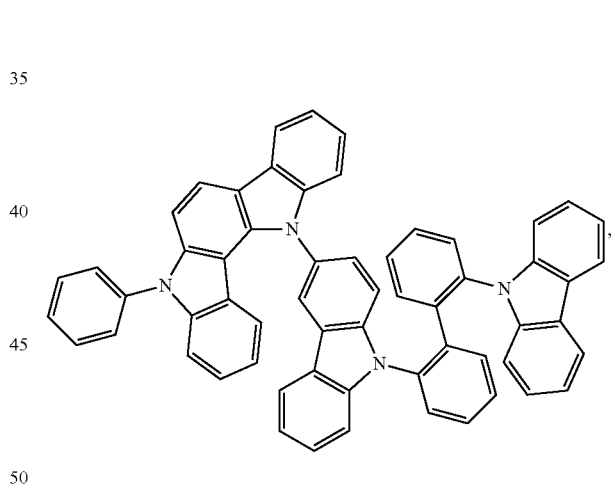
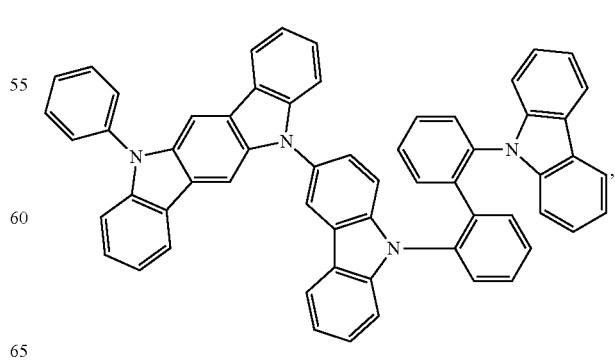

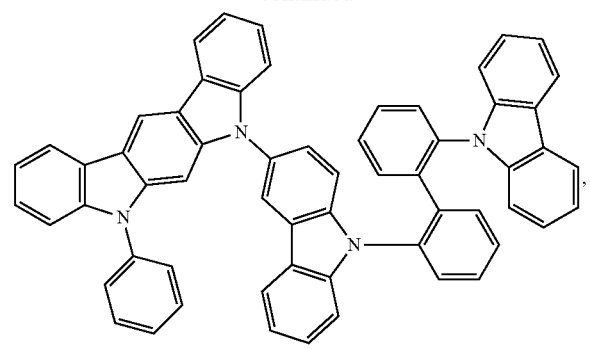
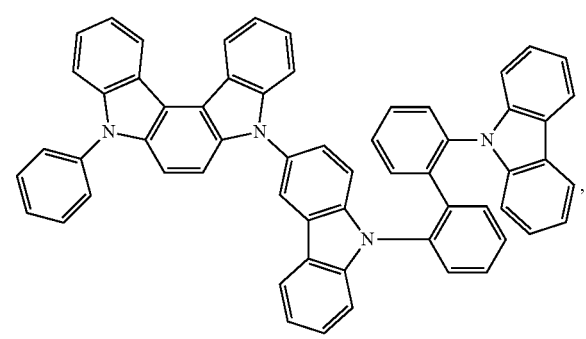
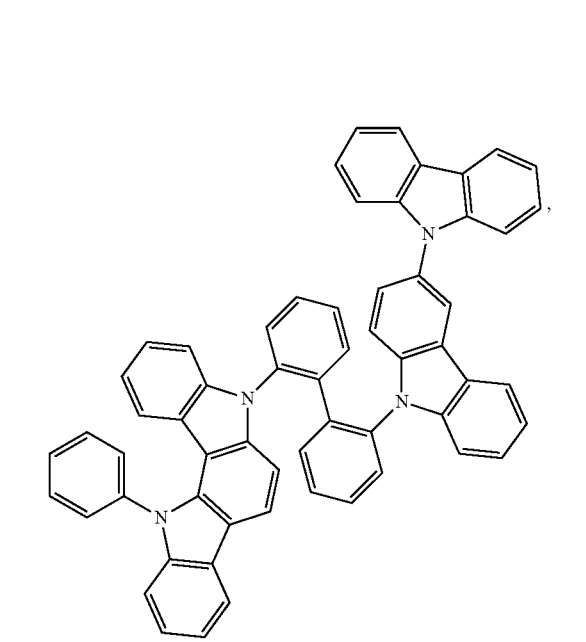
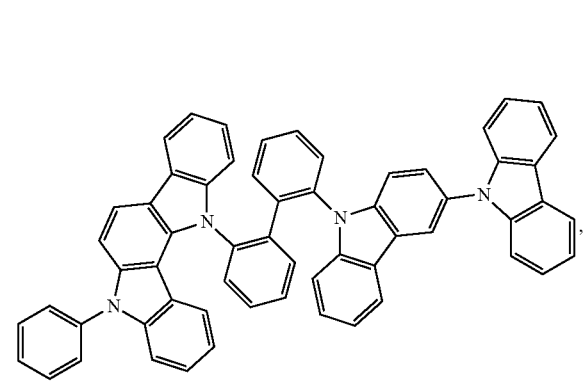
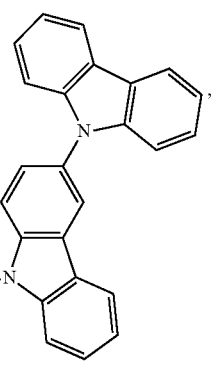
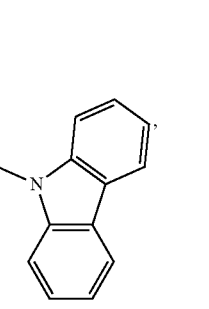
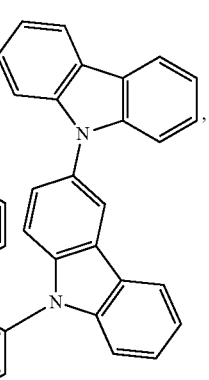

-continued
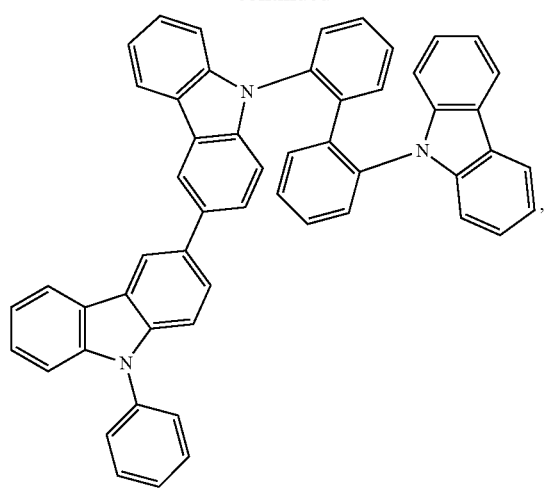
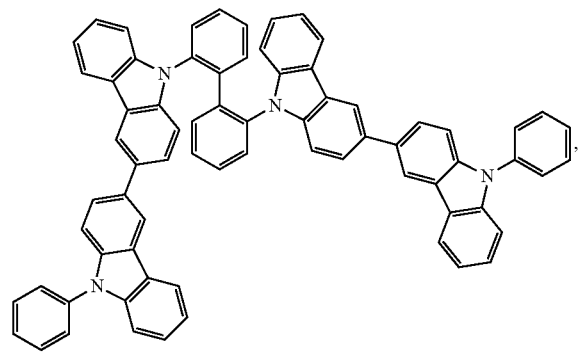
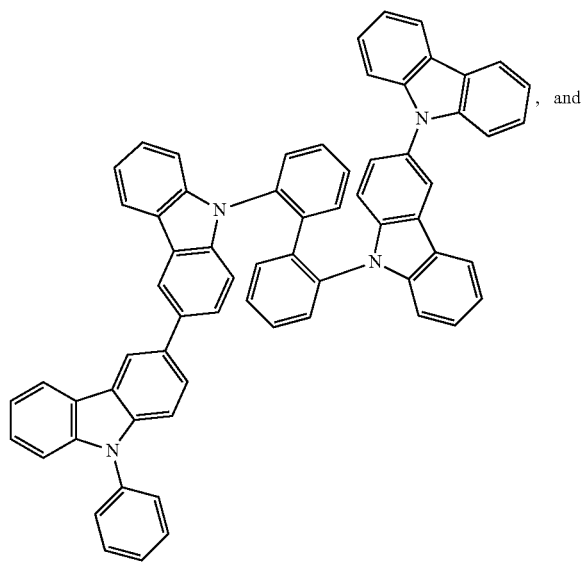
-continued
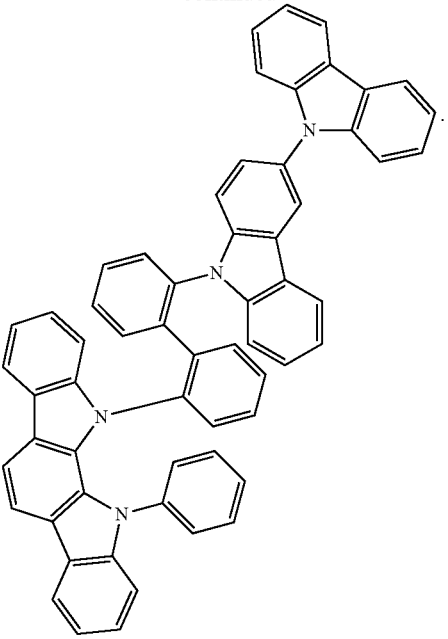
8. An organic light emitting device (OLED) comprising:
   an anode;
   a cathode; and
   an organic layer disposed between the anode and the cathode, wherein the organic layer comprises a compound of Formula I
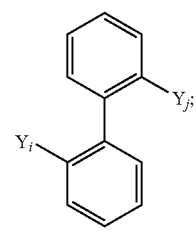
wherein $Y_i$ is
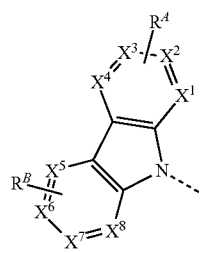
and $Y_j$ is
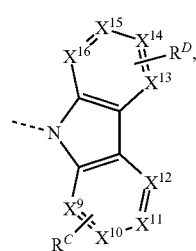

wherein:
R_A, R^B, R^C, and R^D each independently represents zero, mono, di-substitution or the maximum allowable substitution;
each R^A, R^B, R^C, and R^D is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
at least one of R^A, R^B, R^C, and R^D comprises a carbazole moiety;
each of $X^1$-$X^{16}$ is independently C or N;
any two substituents can be joined or fused together to form a ring; and
wherein $Y_i$ is selected from the group consisting of:

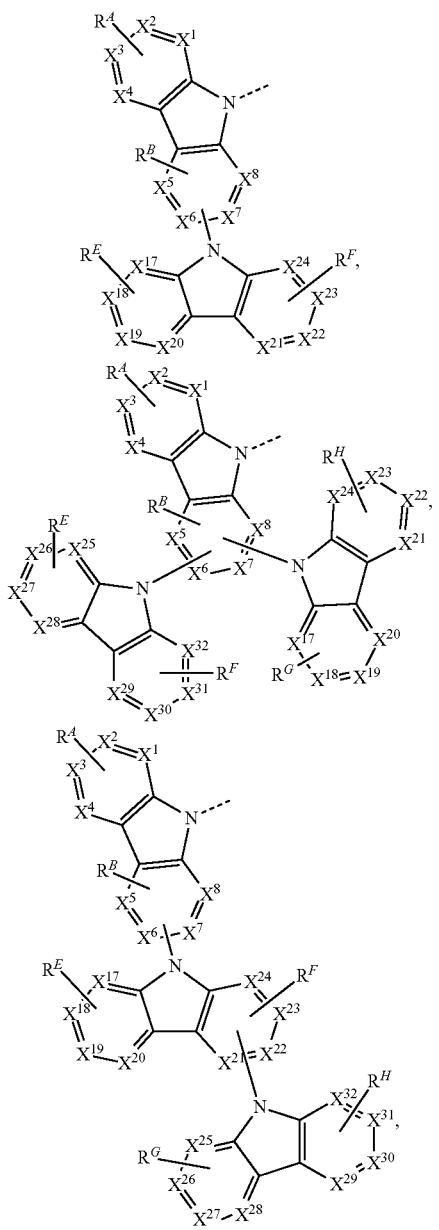

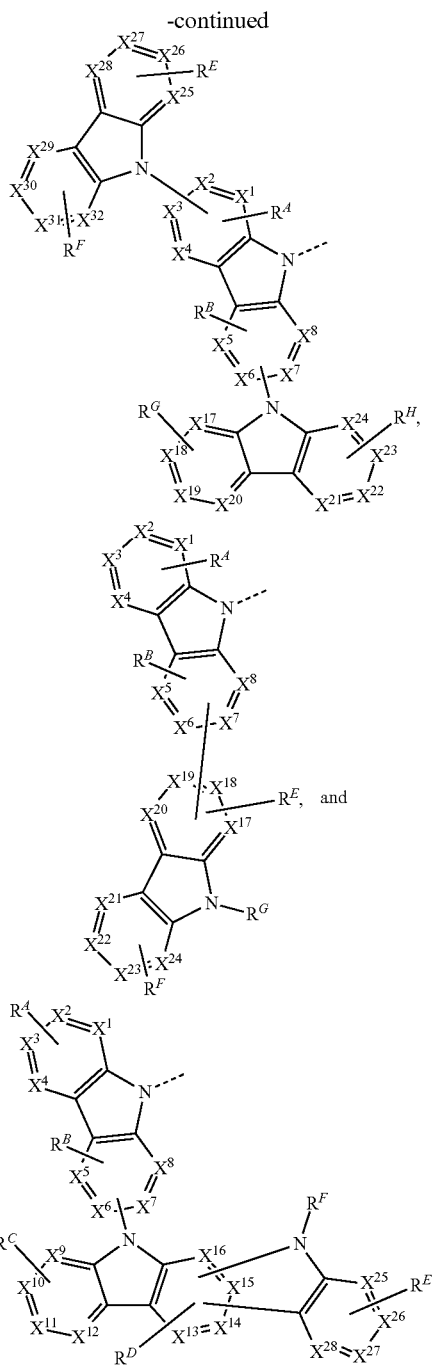

wherein $X^{17}$-$X^{32}$ are each independently C or N;
R^E, R^F, R^G, and R^H each independently represents zero, mono, di-substitution or the maximum allowable substitution;
each R^E, R^F, R^G, and R^H is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and
any two of R^E, R^F, R^G, and R^H can be joined or fused together to form a ring.

9. The OLED of claim 8, wherein the organic layer further comprises a second compound comprising a chemical structure selected from the group consisting of triazine, pyrimidine, pyridines, 9-dioxa-13b-boranaphtho[3,2,1-de]anthracene, aza-naphthalene, aza-fluorene, aza-triphenylene, aza-carbazole, aza-indolocarbazole, aza-dibenzothiophene, aza-dibenzofuran, and aza-dibenzoselenophene, and aza-(5,9-dioxa-13b-boranaphtho[3,2,1-de]anthracene).

10. The OLED of claim 9, wherein the second compound is selected from the group consisting of:

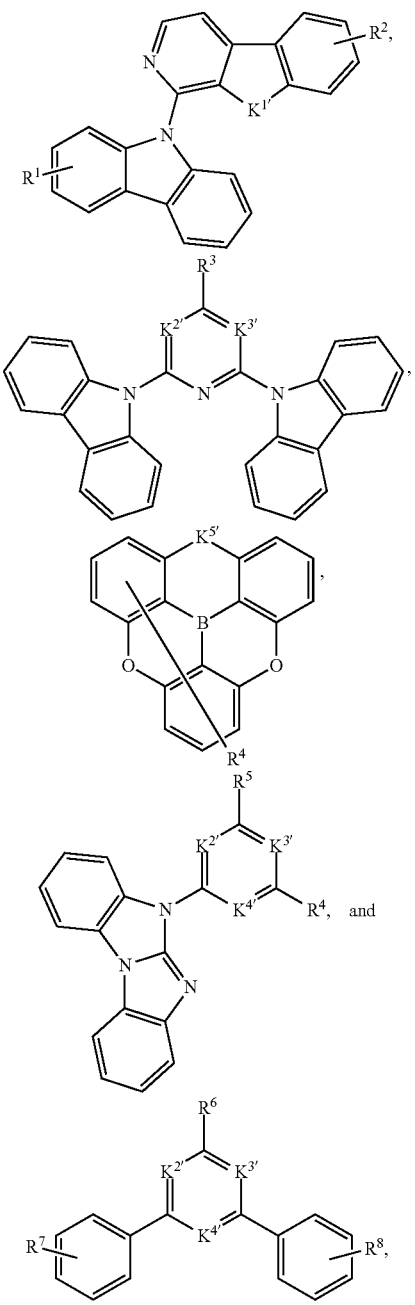

wherein:
K$^{1'}$ is O or S;
K$^{2'}$, K$^{3'}$, and K$^{4'}$ are N or CR$^9$;
K$^{5'}$ is selected from the group consisting of O, S and NR$^{10}$; and R$^1$, R$^2$, R$^3$, R$^4$, R$^5$, R$^6$, R$^7$, R$^8$, R$^9$ and R$^{10}$ are independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

11. The OLED of claim 9, wherein the second compound is selected from the group consisting of:

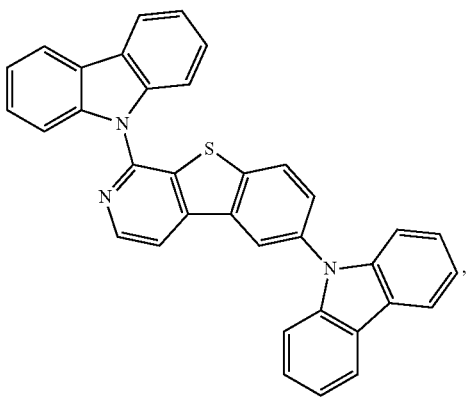

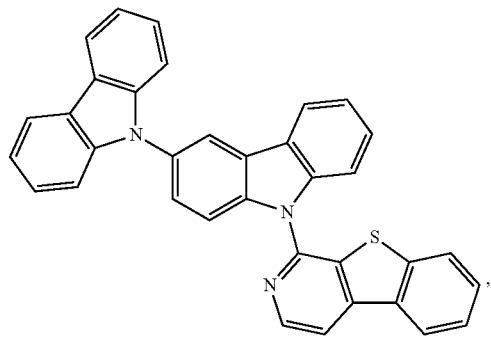

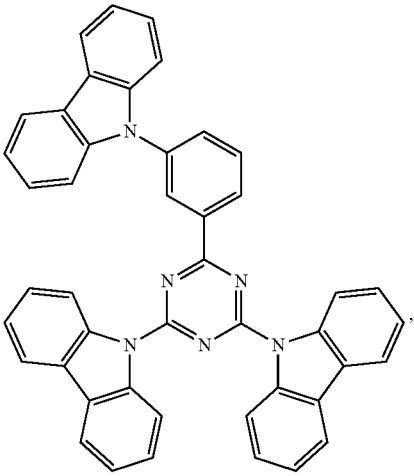

189
-continued
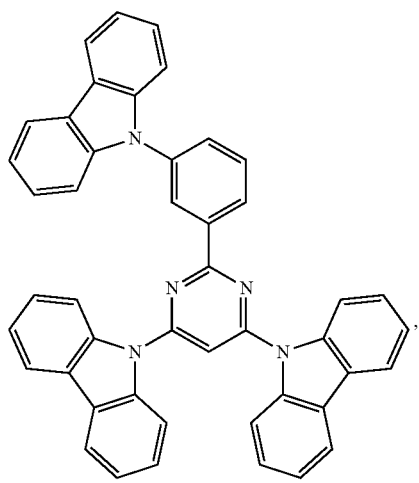
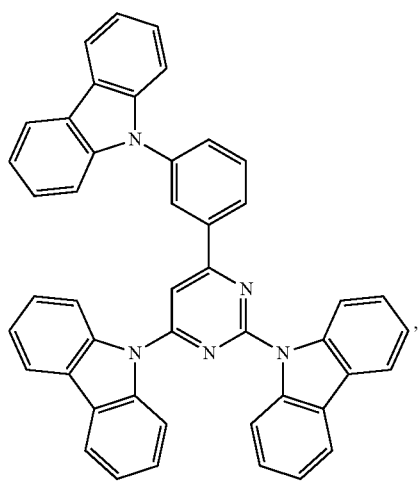
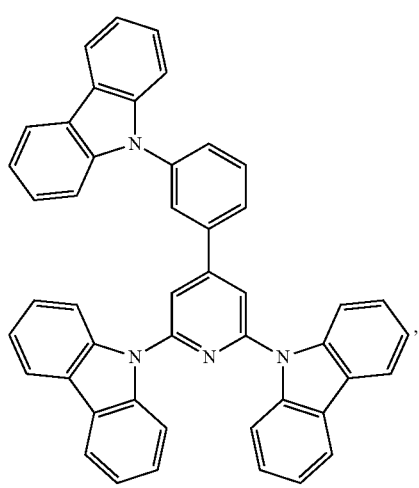
190
-continued
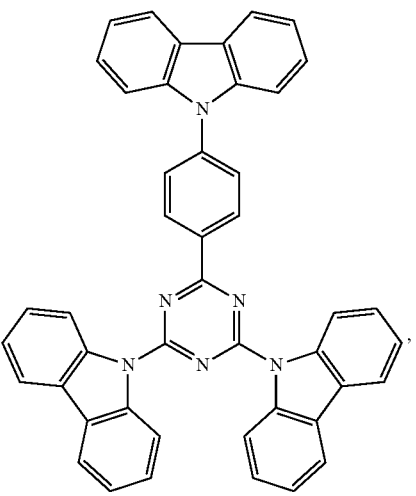
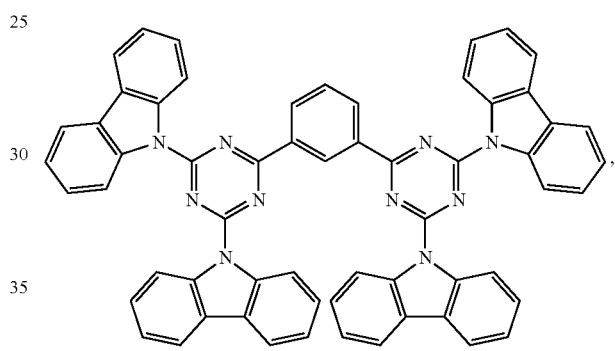
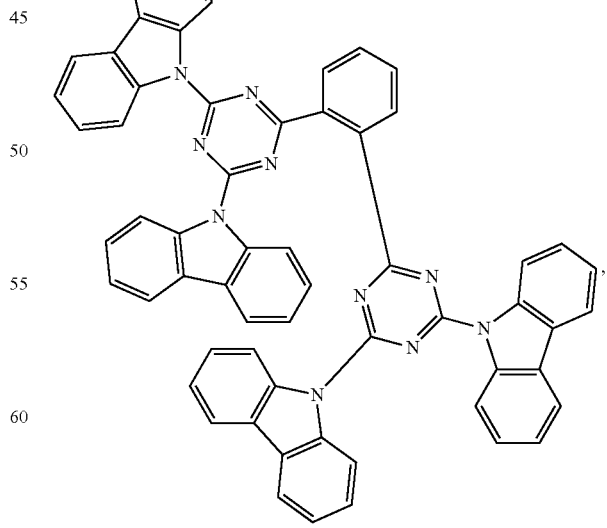

191
-continued
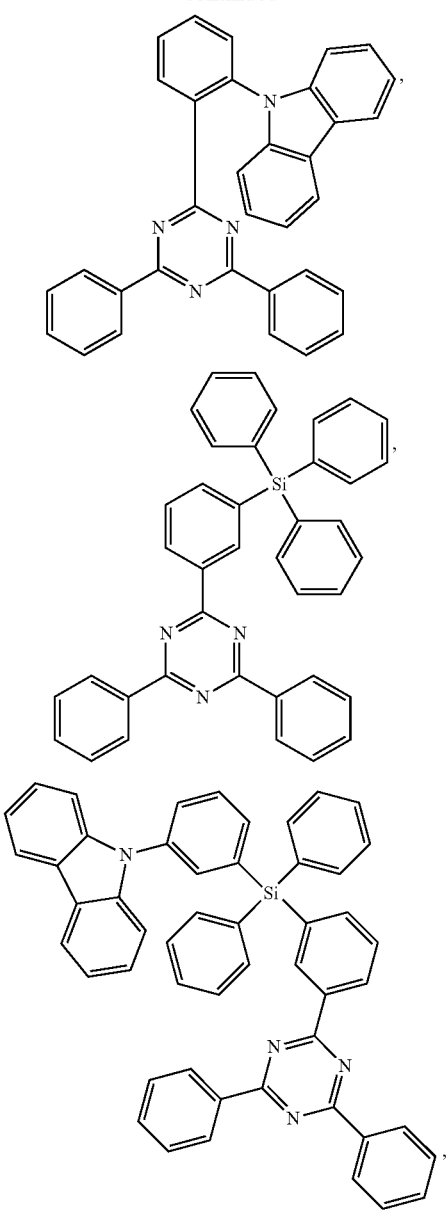
192
-continued
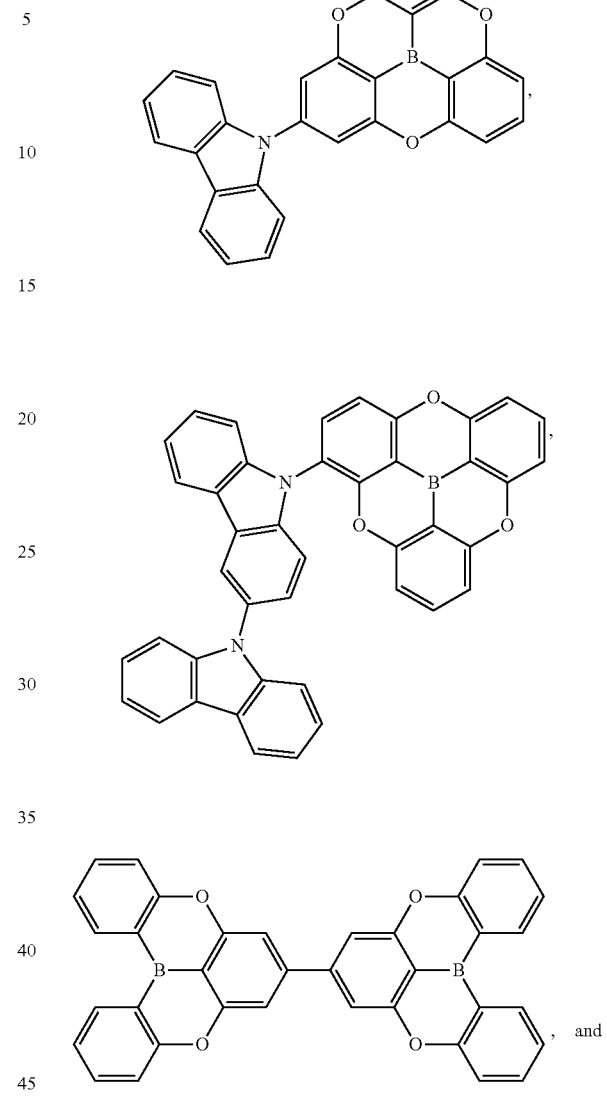
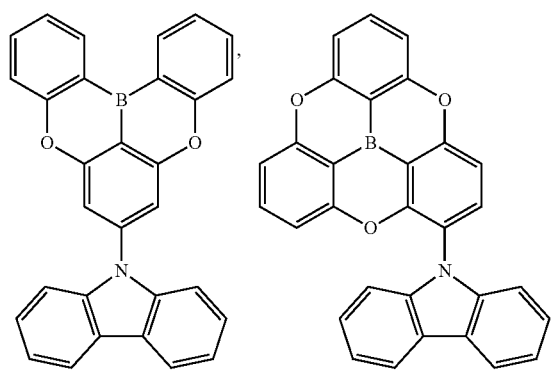
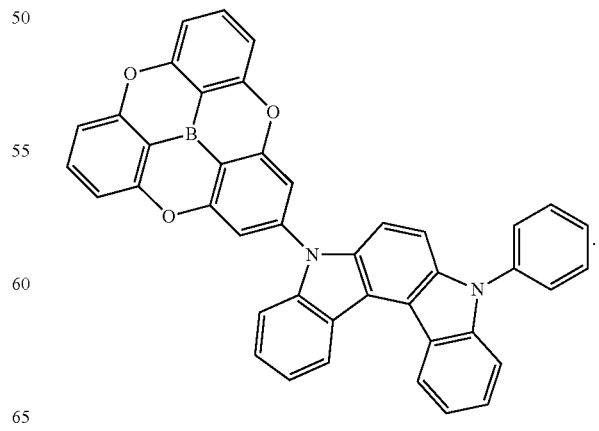

12. The OLED of claim 8, wherein the organic layer further comprises a compound of Formula II

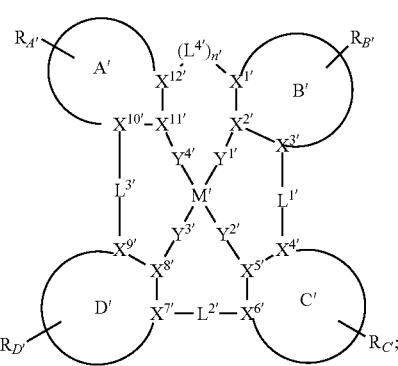

wherein:
M' is Pt or Pd;
rings A', B', C', and D' each independently represents a 5-membered or 6-membered carbocyclic or heterocyclic ring;
$X^{1'}$-$X^{12'}$ are each independently selected from the group consisting of carbon and nitrogen;
$R_{A'}$, $R_{B'}$, $R_{C'}$, and $R^{D'}$ each independently represents mono to the maximum allowed number of substitutions, or no substitution;
each $R_{A'}$, $R_{B'}$, $R_{C'}$, and $R_{D'}$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
n' is 0 or 1;
$L^{1'}$, $L^{2'}$, and $L^{3'}$ are each independently selected from the group consisting of a direct bond, BRR', NR, PR, O, S, Se, C=O, S=O, $SO_2$, CRR', GeRR', and combinations thereof;
when n' is 1, $L^{4'}$ is selected from the group consisting of a direct bond, BRR', NR, PR, O, S, Se, C=O, S=O, $SO_2$, CRR', GeRR', and combinations thereof;
when n' is 0, $L^{4'}$ is not present;
each $Y^{1'}$, $Y^{2'}$, $Y^{3'}$, and $Y^{4'}$ is selected from the group consisting of a direct bond, O, and S;
wherein at least two of $Y^{1'}$, $Y^{2'}$, $Y^{3'}$, and $Y^{4'}$ is a direct bond.

13. The OLED of claim 12, wherein the compound of Formula II is a tetradentate Pt complex that has at least one part of the ligand selected from the group consisting of:

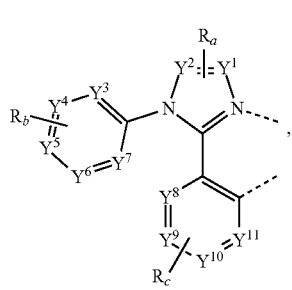

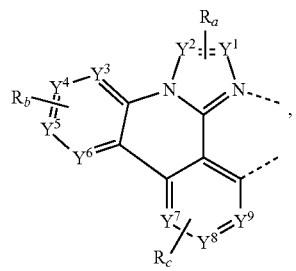

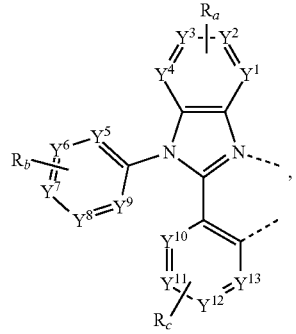

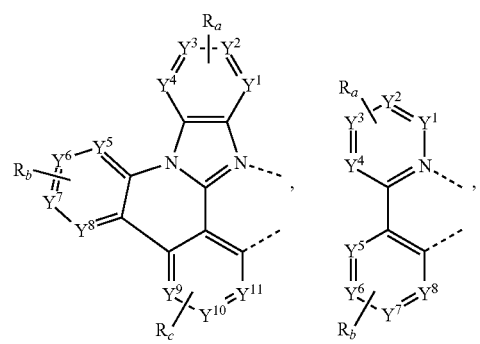

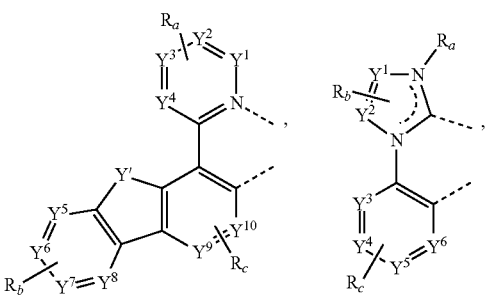

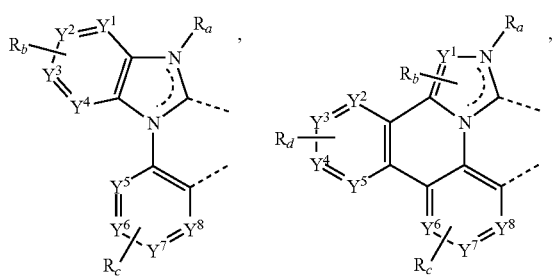

-continued

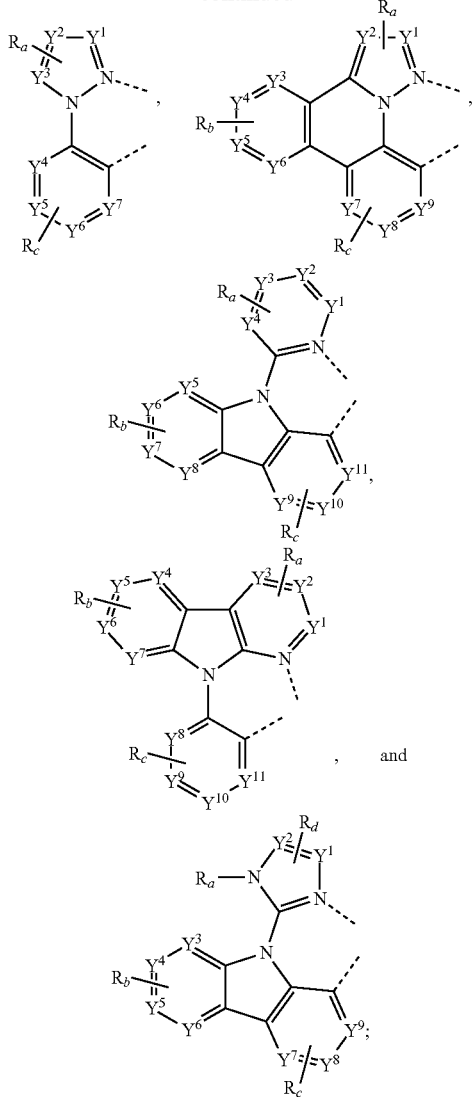

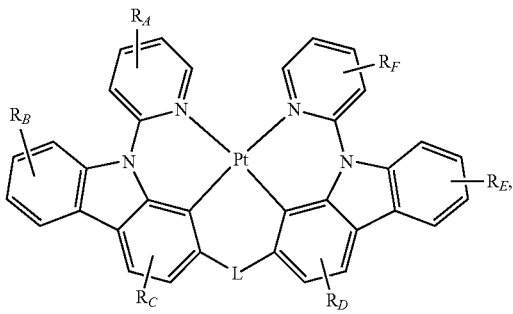

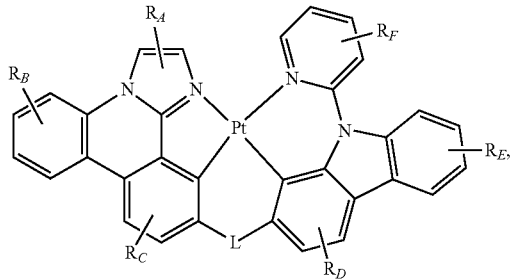

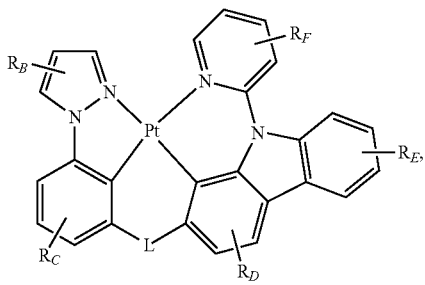

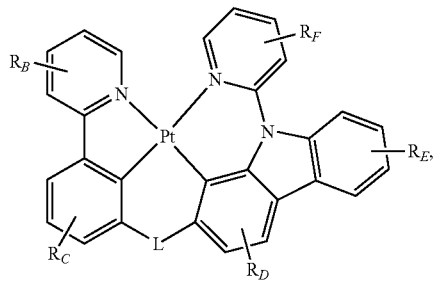

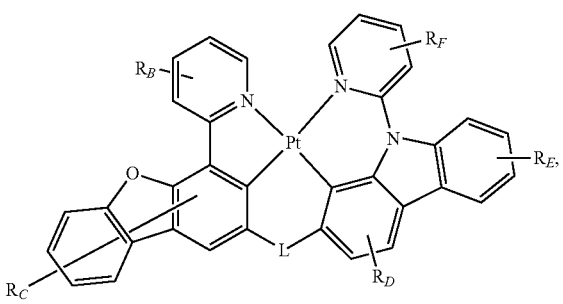

wherein:
  each $Y^1$ to $Y^{13}$ are independently selected from the group consisting of carbon and nitrogen;
  Y' is selected from the group consisting of B $R_e$, N $R_e$, P $R_e$, O, S, Se, C=O, S=O, $SO_2$, $CR_eR_f$, $SiR_eR_f$, and $GeR_eR_f$;
  $R_e$ and $R_f$ are optionally fused or joined to form a ring;
  Each $R_a$, $R_b$, $R_c$, and $R_d$ may independently represent from mono substitution to the maximum possible number of substitution, or no substitution;
  each $R_a$, $R_b$, $R_c$, $R_d$, $R_e$ and $R_f$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and
  any two adjacent substituents of $R_a$, $R_b$, $R_c$, and $R_d$ are optionally fused or joined to form a ring.

14. The OLED of claim 12, wherein the compound of Formula II is selected from the group consisting of:

197
-continued

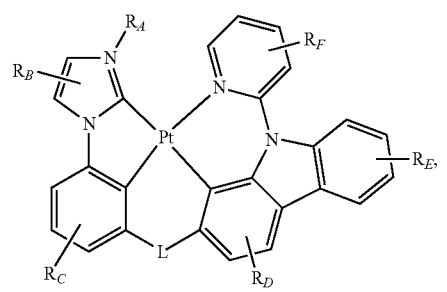

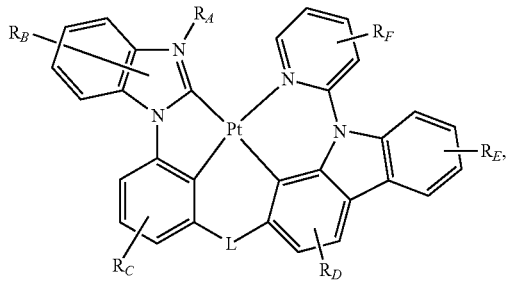

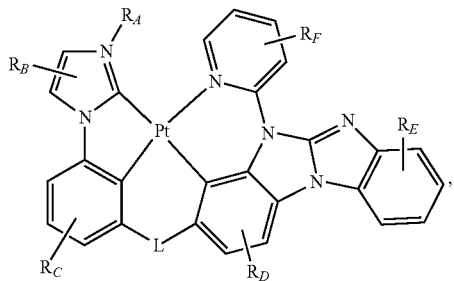

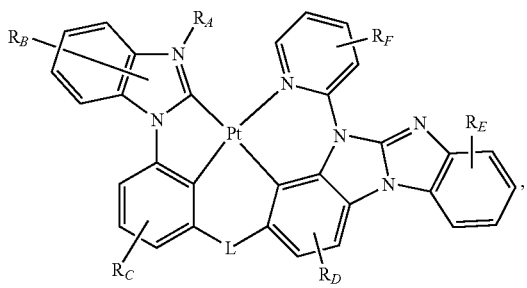

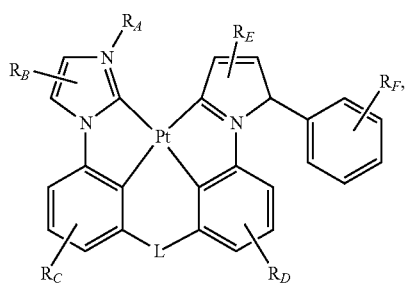

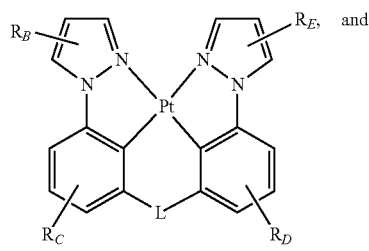

and

198
-continued

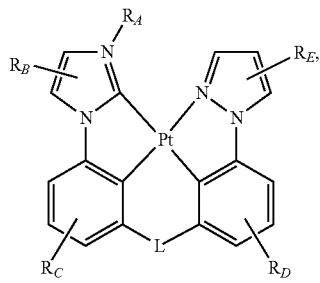

wherein:

L is selected form the group consisting of O, S, Se, NR, BR, BRR', C=O, S=O, CRR', SiRR', and combinations thereof; and each $R_A$, $R_B$, $R_C$, $R_D$, $R_E$, and $R_F$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

15. The OLED of claim 8, wherein the compound is a host, and the organic layer is an emissive layer that comprises a phosphorescent emitter.

16. The OLED of any one of claim 15, wherein the phosphorescent emitter is a transition metal complex having at least one ligand or part of the ligand if the ligand is more than bidentate selected from the group consisting of:

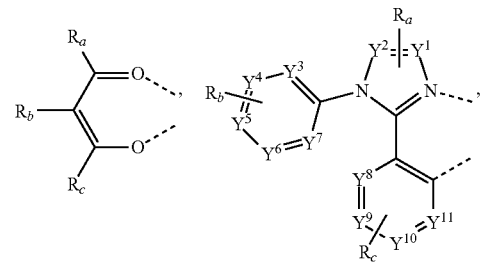

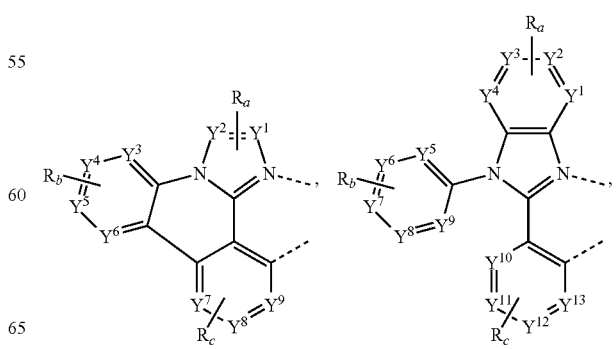

-continued

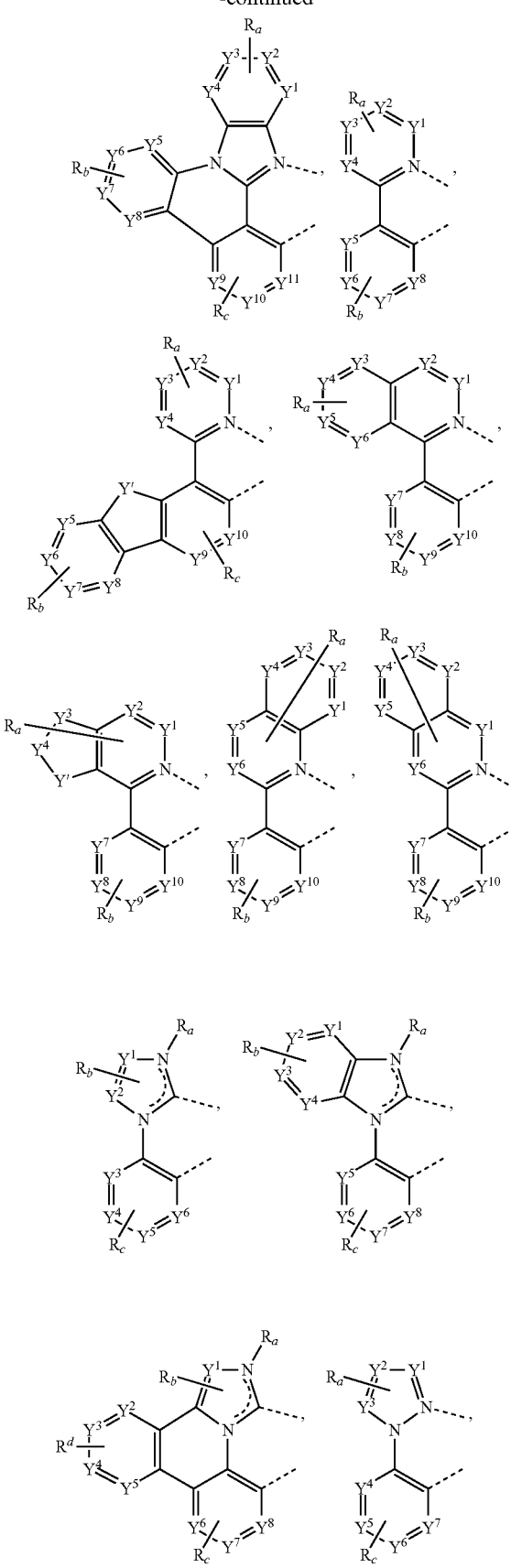
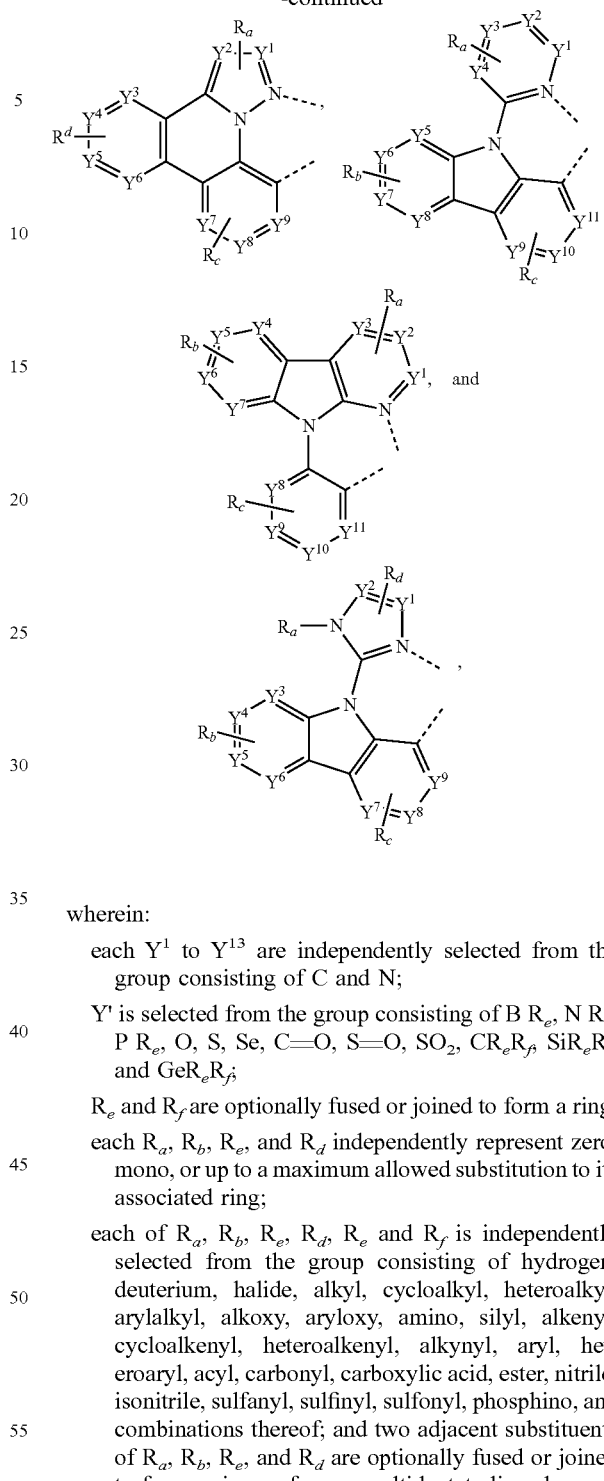

wherein:
each $Y^1$ to $Y^{13}$ are independently selected from the group consisting of C and N;

Y' is selected from the group consisting of B $R_e$, N $R_e$, P $R_e$, O, S, Se, C=O, S=O, $SO_2$, $CR_eR_f$, $SiR_eR_f$, and $GeR_eR_f$;

$R_e$ and $R_f$ are optionally fused or joined to form a ring;

each $R_a$, $R_b$, $R_c$, and $R_d$ independently represent zero, mono, or up to a maximum allowed substitution to its associated ring;

each of $R_a$, $R_b$, $R_c$, $R_d$, $R_e$ and $R_f$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and two adjacent substituents of $R_a$, $R_b$, $R_c$, and $R_d$ are optionally fused or joined to form a ring or form a multidentate ligand.

17. A consumer product comprising an organic light-emitting device comprising:
an anode;
a cathode; and
an organic layer disposed between the anode and the cathode,
wherein the organic layer comprises a compound of Formula I

201

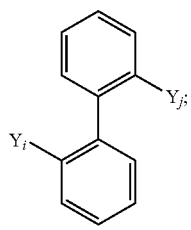

wherein $Y_i$ is

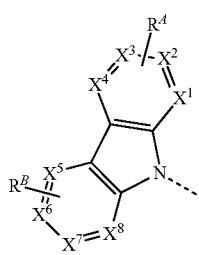

and $Y_j$ is

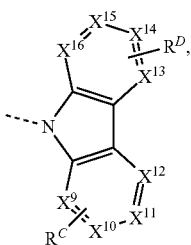

wherein:
  $R^A$, $R^B$, $R^C$, and $R^D$ each independently represents zero, mono, di-substitution or the maximum allowable substitution;
  each $R^A$, $R^B$, $R^C$, and $R^D$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
  at least one of $R^A$, $R^B$, $R^C$, and $R^D$ comprises a carbazole moiety;
  each of $X^1$-$X^{16}$ is independently C or N;
  any two substituents can be joined or fused together to form a ring; and

202 wherein $Y_i$ is selected from the group consisting of:

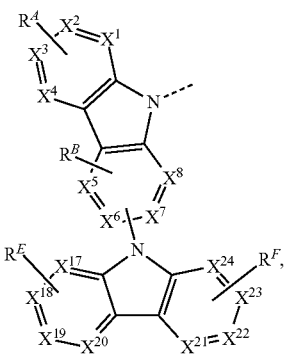

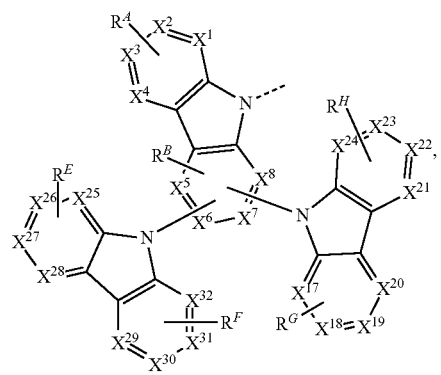

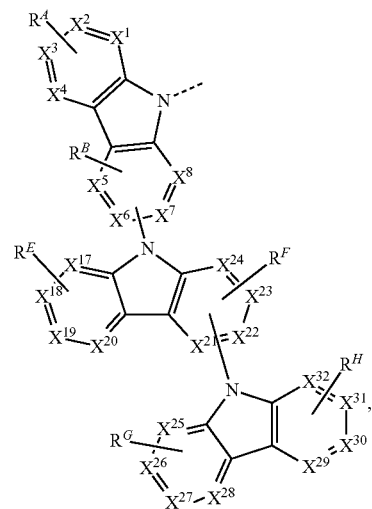

-continued

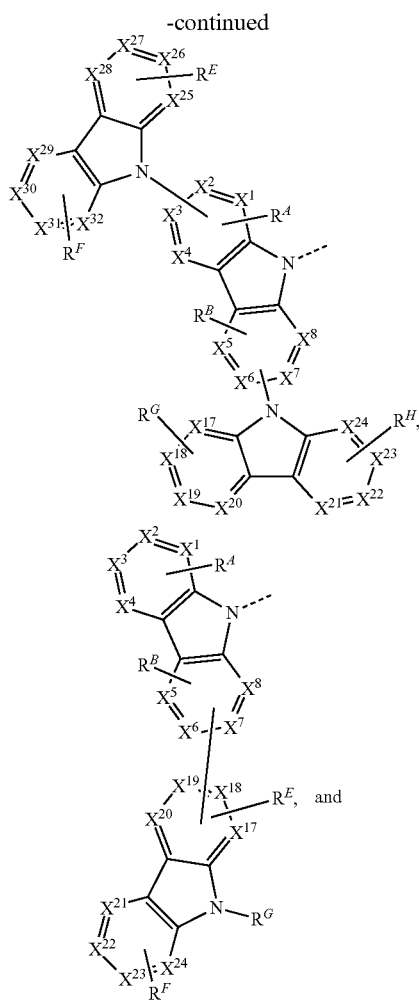

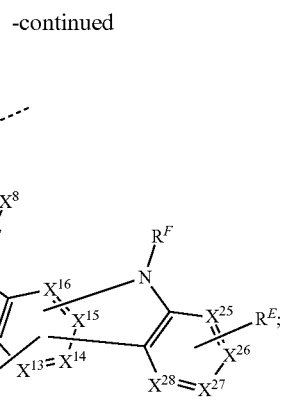

wherein $X^{17}$-$X^{32}$ are each independently C or N;

$R^E$, $R^F$, $R^G$, and $R^H$ each independently represents zero, mono, di-substitution or the maximum allowable substitution;

each $R^E$, $R^F$, $R^G$, and $R^H$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and any two of $R^E$, $R^F$, $R^G$, and $R^H$ can be joined or fused together to form a ring.

18. A formulation comprising a compound of Formula I according to claim 1.

* * * * *